US012778971B2

(12) United States Patent
Falk

(10) Patent No.: US 12,778,971 B2
(45) Date of Patent: Nov. 3, 2026

(54) COMPOSITIONS AND METHODS FOR TREATMENT OF MITOCHONDRIAL RESPIRATORY CHAIN DYSFUNCTION AND OTHER MITOCHONDRIAL DISORDERS

(71) Applicant: THE CHILDREN'S HOSPITAL OF PHILADELPHIA, Philadelphia, PA (US)

(72) Inventor: Marni J. Falk, Voorhees, NJ (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 18/512,636

(22) Filed: Nov. 17, 2023

(65) Prior Publication Data

US 2024/0180938 A1 Jun. 6, 2024

Related U.S. Application Data

(63) Continuation of application No. 17/256,406, filed as application No. PCT/US2019/039631 on Jun. 27, 2019, now Pat. No. 12,011,452.

(60) Provisional application No. 62/830,850, filed on Apr. 8, 2019, provisional application No. 62/690,718, filed on Jun. 27, 2018.

(51) Int. Cl.

| | |
|---|---|
| ***A61K 31/7004*** | (2006.01) |
| ***A61K 31/095*** | (2006.01) |
| ***A61K 31/194*** | (2006.01) |
| ***A61K 31/197*** | (2006.01) |
| ***A61K 31/455*** | (2006.01) |
| ***A61P 43/00*** | (2006.01) |
| ***G01N 33/50*** | (2006.01) |
| ***G01N 33/68*** | (2006.01) |

(52) U.S. Cl.

CPC ........ *A61K 31/7004* (2013.01); *A61K 31/095* (2013.01); *A61K 31/194* (2013.01); *A61K 31/197* (2013.01); *A61K 31/455* (2013.01); *A61P 43/00* (2018.01); *G01N 33/5008* (2013.01); *G01N 33/68* (2013.01); *G01N 2800/52* (2013.01)

(58) Field of Classification Search

CPC .............. A61K 31/7004; A61K 31/095; A61K 31/194; A61K 31/197; A61K 31/455; A61P 43/00; G01N 33/5008; G01N 2333/68; G01N 2800/52

USPC ............................................................ 514/23

See application file for complete search history.

(56) References Cited

U.S. PATENT DOCUMENTS

| | | | | |
|---|---|---|---|---|
| 6,746,678 B1 * | 6/2004 | Shapiro | A61K 31/63 514/567 |
| 2017/0290768 A1 * | 10/2017 | Barzilay | A61K 9/5063 |

FOREIGN PATENT DOCUMENTS

| | | | |
|---|---|---|---|
| WO | 2017/027810 A2 | | 2/2017 |
| ZA | 200109677 B | * | 6/2002 |

OTHER PUBLICATIONS

'Glossary of Medical Education Terms', Institute for International Medical Education (IIME), https://www.iime.org/glossary.htm#P (Revised on Feb. 2002; accessed on Apr. 20, 2024) (Year: 2002).*

Niacin, Fact sheet for health professionals, NIH, p. 1-22, Updated: Nov. 18, 2022, https://ods.od.nih.gov/factsheets/Niacin-HealthProfessional/ (Year: 2022).*

Falk et al. National Academies of Sciences, Engineering, and Medicine. 2018. Examining special nutritional requirements in disease states: Proceedings of a workshop. Washington, DC: The National Academies Press. doi: https://doi. org/10.17226/25164.(p. 1-150) (Year: 2018).*

International Search Report and Written Opinion, dated Nov. 13, 2019 issued in International Application No. PCT/US2019/039631, filed Jun. 27, 2019.

Zschocke, Johannes et al., "The diagnosis of mitochondrial HMG-CoA synthase deficiency," The Journal of Pediatrics, vol. 140, No. 6, 2002, pp. 778-780.

Dean, Olivia M. et al., "Design and rationale of a 16-week adjunctive randomized placebo-controlled trial of mitochondrial agents for the treatment of bipolar depression," Brazilian Journal of Psychiatry, vol. 37, No. 1, 2015, pp. 3-12.

Extended European Search Report, dated Feb. 17, 2022, issued in corresponding European Patent Application No. 19825237.1.

Guha, Sujay et al., "Pre-clinical evaluation of cysteamine bitartrate as a therapeutic agent for mitochondrial respiratory chain disease," Human Molecular Genetics, vol. 28, No. 11, 2019, pp. 1837-1852.

Maglioni, Silvia et al., "C. elegans as a model organism for human mitochondrial associated disorders," Mitochondrion, vol. 30, 2016, pp. 117-125.

Burns, Andrew R. et al., "High-throughput screening of small molecules for bioactivity and target identification in Caenorhabditis elegans," Nature Protocols, vol. 1, No. 4, 2006, pp. 1906-1914.

Pinho, Brigida R. et al., "How mitochondrial dysfunction affects zebrafish development and cardiovascular function: an in vivo model for testing mitochondria-targeted drugs," British Journal of Pharmacology, vol. 169, No. 5, 2013, pp. 1072-1090.

Parikh, Sumit et al., "A Modern Approach to the Treatment of Mitochondrial Disease," Current Treatment Options in Neurology, vol. 11, No. 6, 2009, pp. 414-430.

Byrnes, James et al., "Pharmacologic modeling of primary mitochondrial respiratory chain dysfunction in zebrafish," Neurochemistry International, vol. 117, 2018, pp. 23-34.

(Continued)

*Primary Examiner* — Yih-Horng Shiao

(74) *Attorney, Agent, or Firm* — Howson & Howson, LLP; Kathleen D. Rigaut; Richard F. Kane

(57) ABSTRACT

Compositions and methods for treatment of mitochondrial respiratory chain dysfunction and other mitochondrial disorders are provided. Also disclosed are a number of screening assays having utility for the identification of agents which modulate the phenotype associated with mitochondrial respiratory chain dysfunction.

4 Claims, 65 Drawing Sheets

(56) References Cited

OTHER PUBLICATIONS

Swalwell, Helen et al., "Respiratory chain complex I deficiency caused by mitochondrial DNA mutations," European Journal of Human Genetics, vol. 19, 2011, pp. 769-775.
Smeitink, Jan A. M. et al., "Cell biological consequences of mitochondrial NADH: ubiquinone oxidoreductase deficiency," Current Neurovascular Research, vol. 1, No. 1, 2004, pp. 29-40.
Bych, Katrine et al., "The iron-sulphur protein Ind1 is required for effective complex I assembly," The EMBO Journal, vol. 27, No. 12, 2008, pp. 1736-1746.
Sheftel, Alex D. et al., "Human Ind1, an Iron-Sulfur Cluster Assembly Factor for Respiratory Complex I," Molecular and Cellular Biology, vol. 29, No. 22, 2009, pp. 6059-6073.
Falk, Marni J. et al., "Probucol ameliorates renal and metabolic sequelae of primary CoQ deficiency in Pdss2 mutant mice," EMBO Molecular Medicine, vol. 3, No. 7, 2011, pp. 410-427.
McCormack, Shana et al., "Pharmacologic targeting of sirtuin and PPAR signaling improves longevity and mitochondrial physiology in respiratory chain complex I mutant Caenorhabditis elegans," Mitochondrion, vol. 22, 2015, pp. 45-59.
Peng, Min et al., "Inhibiting cytosolic translation andautophagyimproves health in mitochondrial disease," Human Molecular Genetics, vol. 24, No. 17, 2015, pp. 4829-4847.
Churgin, Matthew A. et al., "Longitudinal imaging of Caenorhabditis elegans in a microfabricated device reveals variation in behavioral decline during aging," vol. 6, e26652, 2017, pp. 1-25.
Guha, Sujay et al., "Combinatorial glucose, nicotinic acid and N-acetylcysteine therapy has synergystic effect in preclinical C. elegans and zebrafish models of mitochondrial complex I disease," Human Molecular Genetics, vol. 30, No. 7, 2021, pp. 536-551.
Peng Min et al., "Inhibiting cystolic translation and autophagy improves health in mitochondrial disease", Human Molecular Genetics, vol. 24, No. 17, Sep. 1, 2015, pp. 4829-4847, XP055894702.
Communication pursuant to Article 94(3) EPC, dated Jul. 19, 2023, issued in corresponding European Patent Application No. 19825237.1.

* cited by examiner

Fig. 1A N2
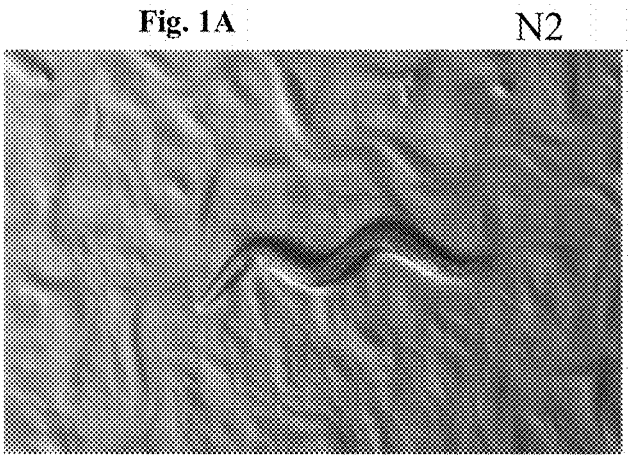
Fig. 1B *fbxl-*
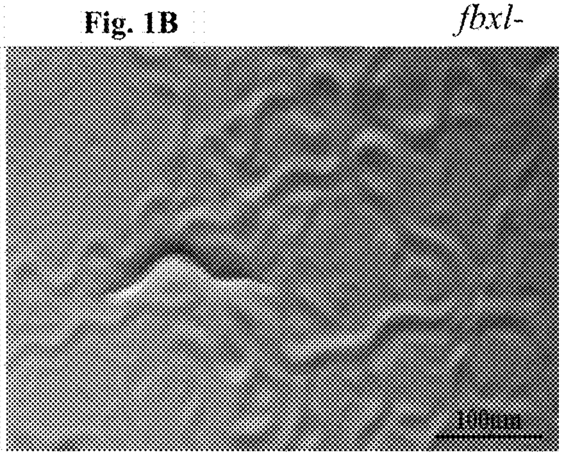
Fig. 1C Fig. 1D
N2 *fbxl-1*

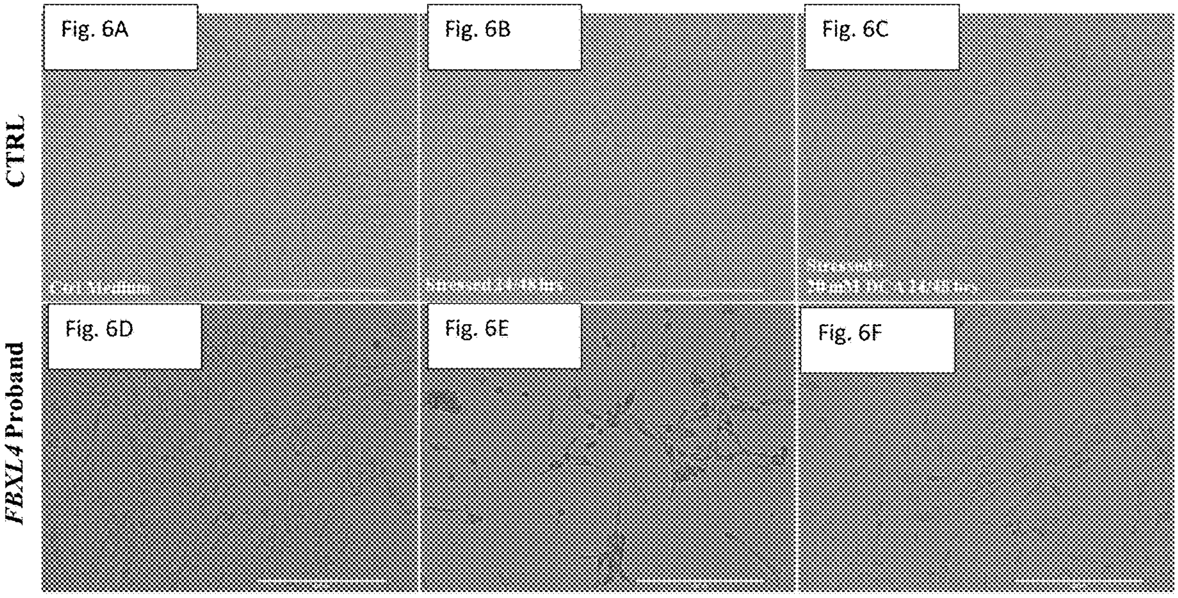
CTRL
*FBXL4* Proband
Fig. 6A
Fig. 6B
Fig. 6C
Fig. 6D
Fig. 6E
Fig. 6F
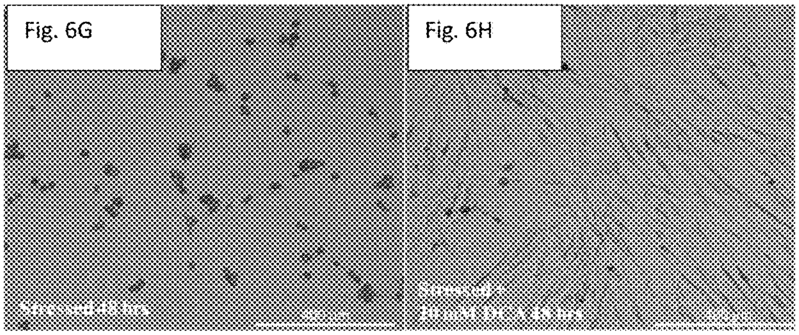
Fig. 6G
Fig. 6H

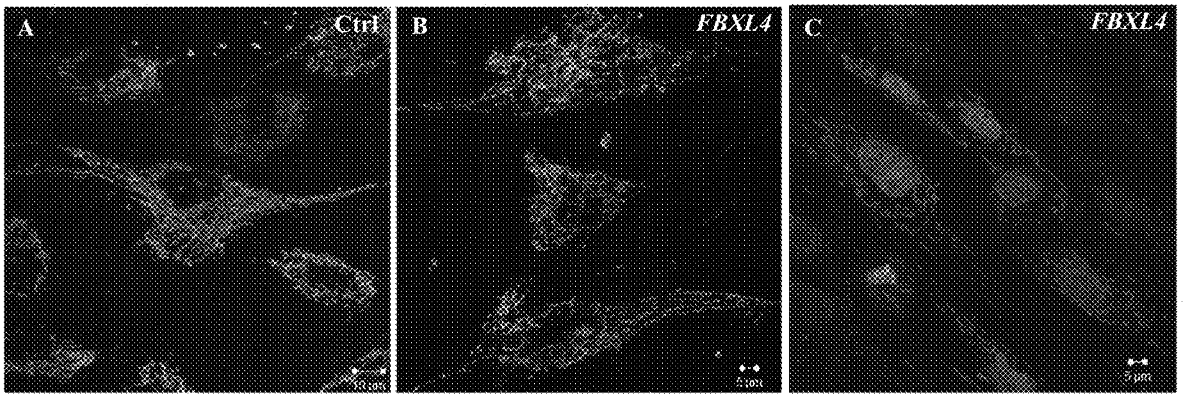
Fig. 7A Fig. 7B Fig. 7C
Fig. 8A Fig. 8B Fig. 8C
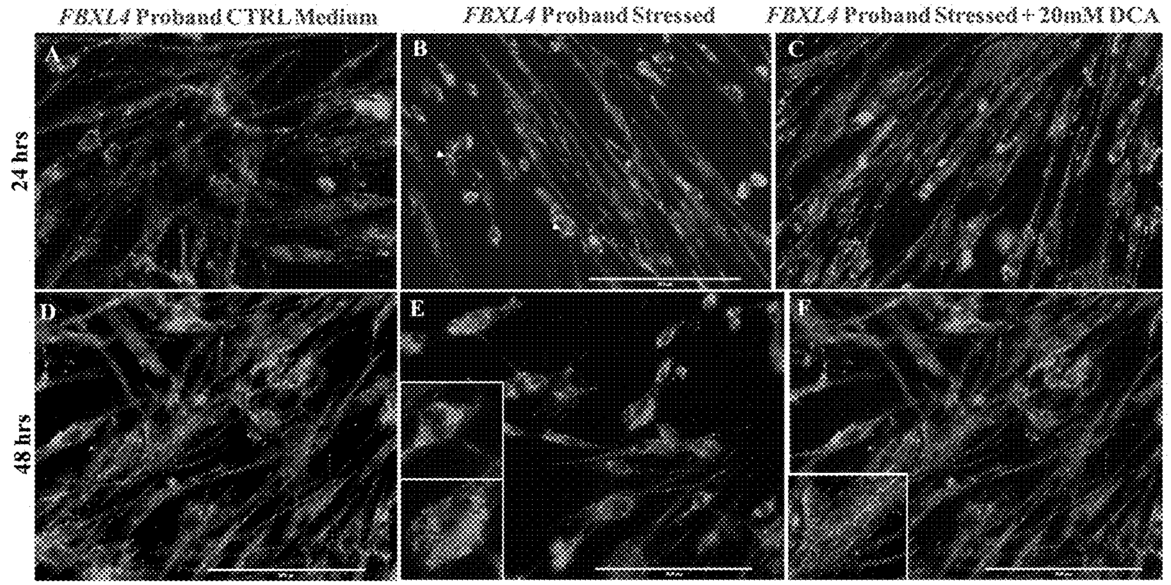
Fig. 8D Fig. 8E Fig. 8F Control *FBXL-1*

WT $fbxl4^{sa12470}$

Stressed WT

Stressed $fbxl4^{sa12470}$

Treated $fbxl4^{sa12470}$

ACTIVITY ANALYSIS

Fig. 14C
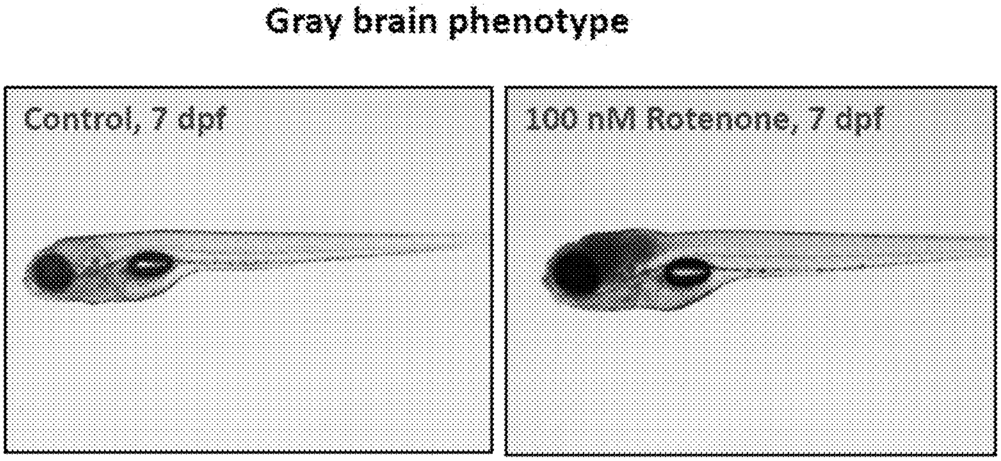
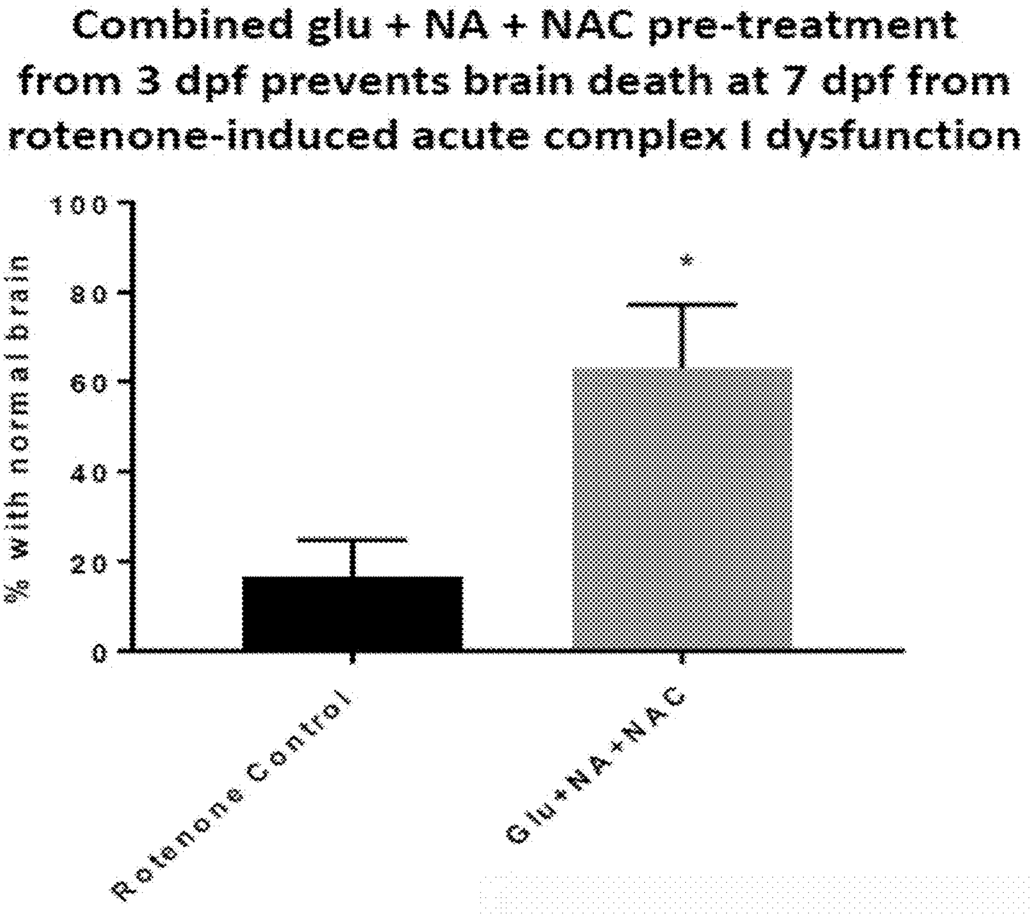
Fig. 14D

FIG. 17A
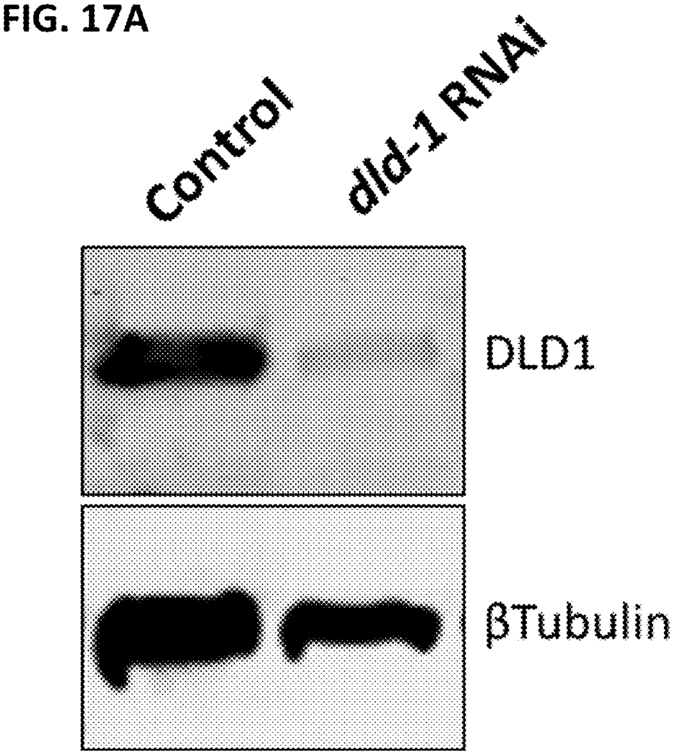
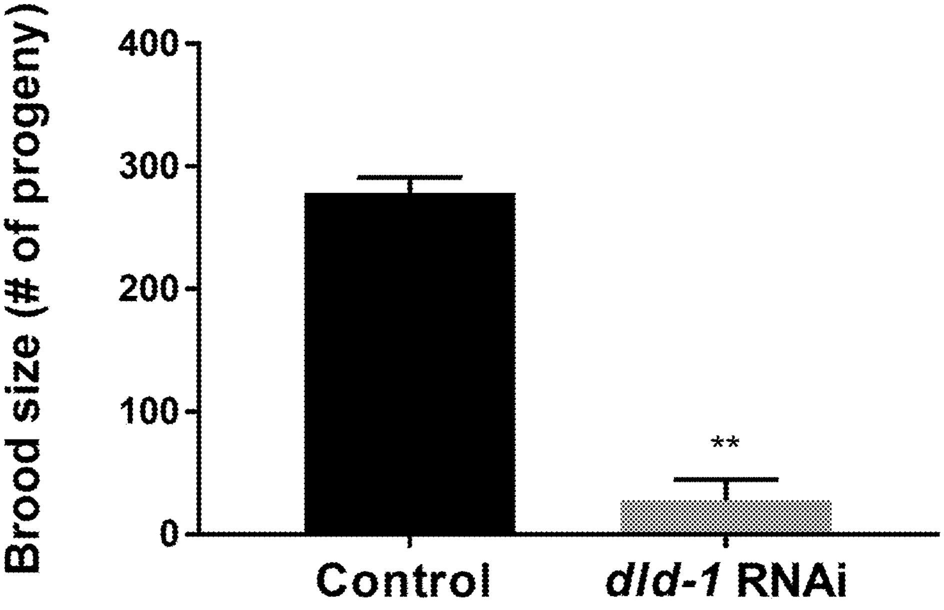
FIG. 17B

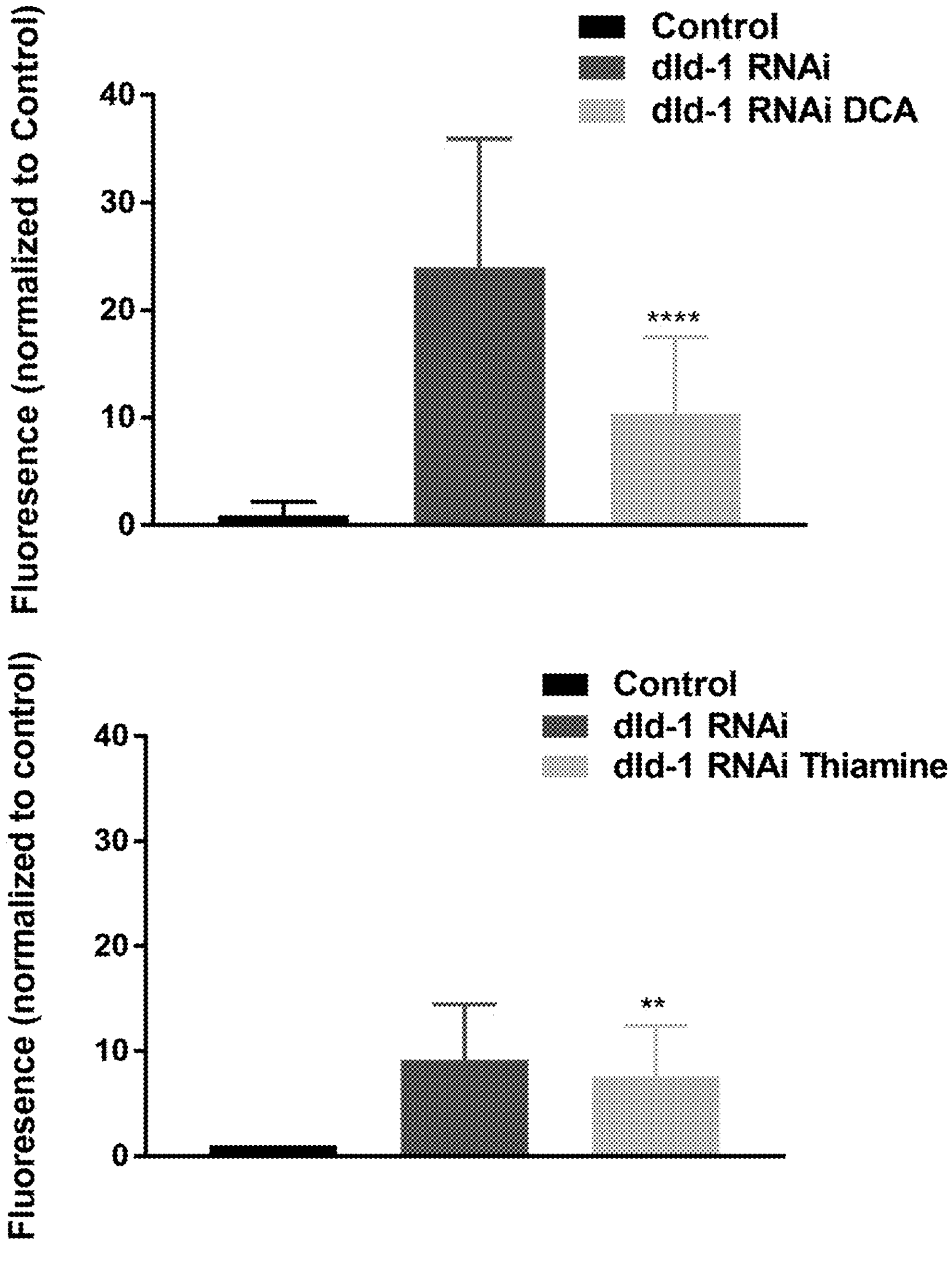
FIG. 19A MITOCHONDRIAL STRESS

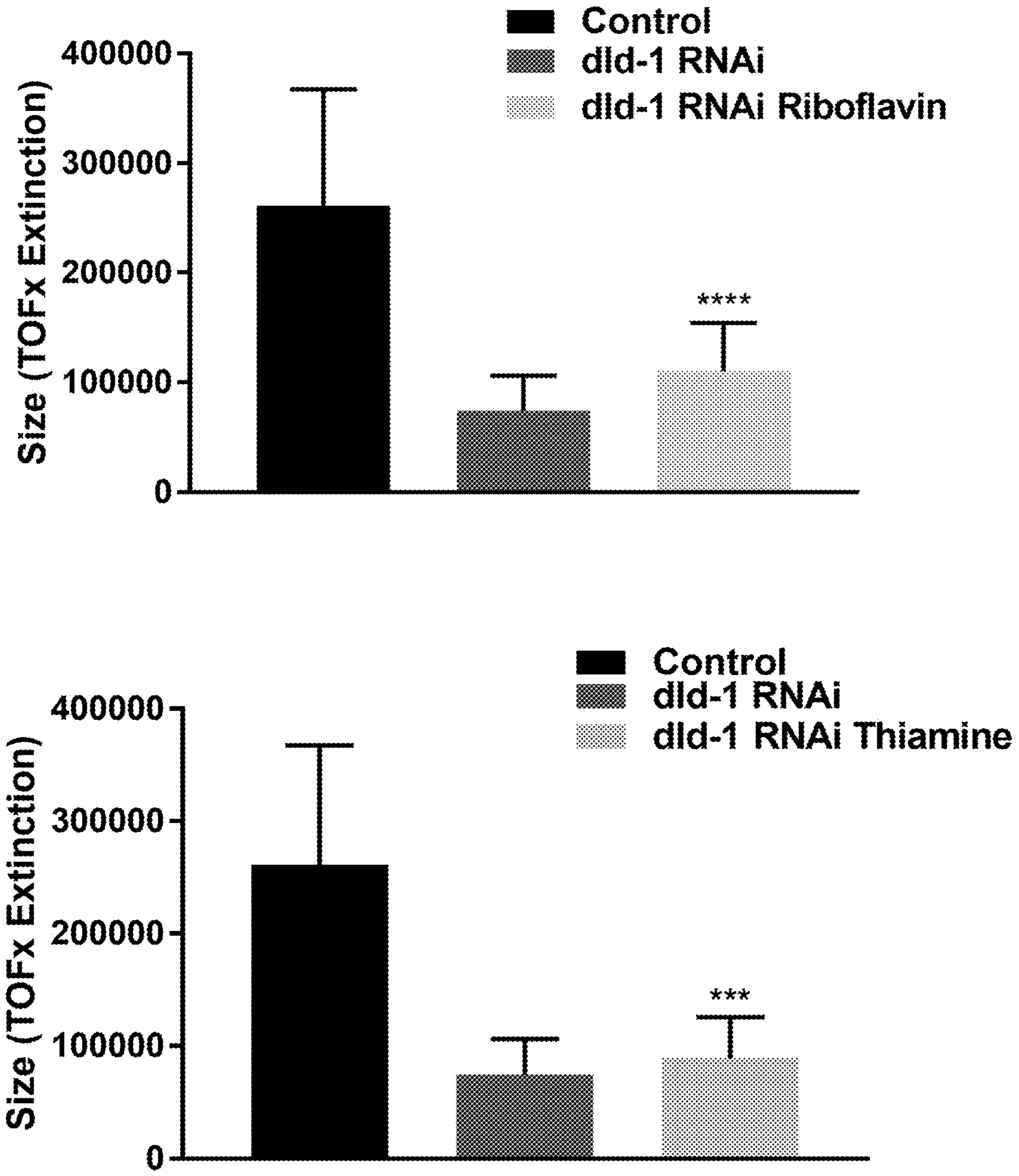
FIG. 19B ANIMAL SIZE

Fig. 23A
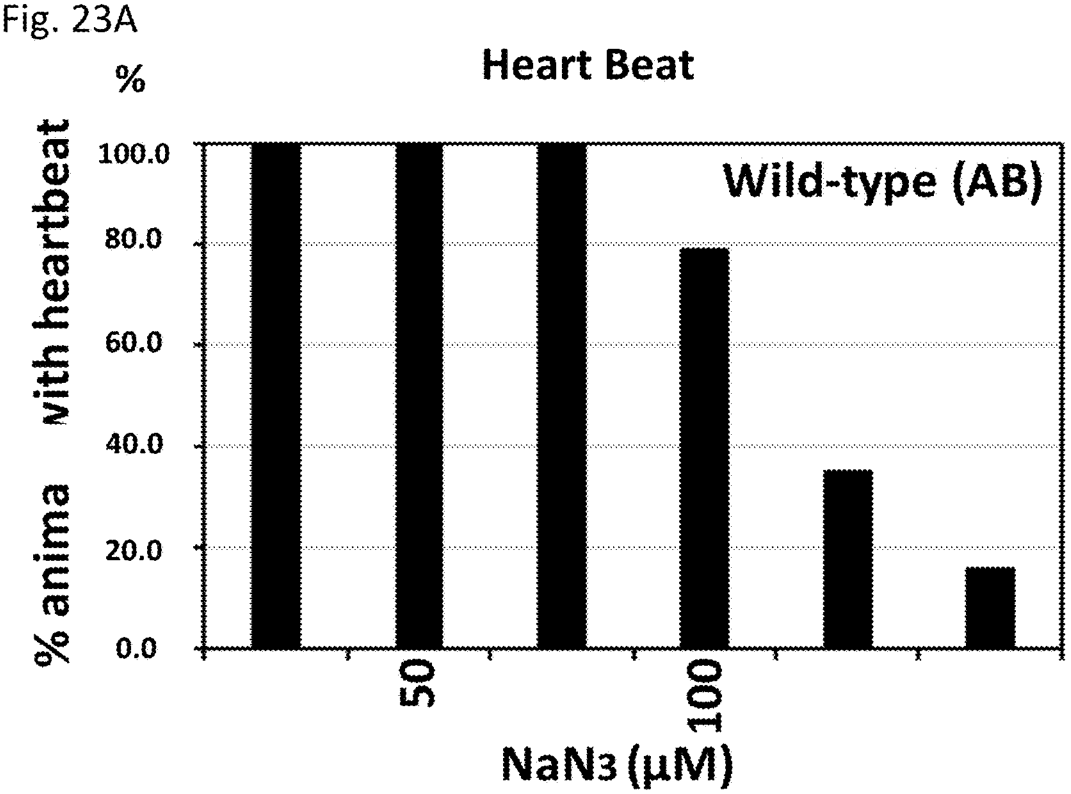
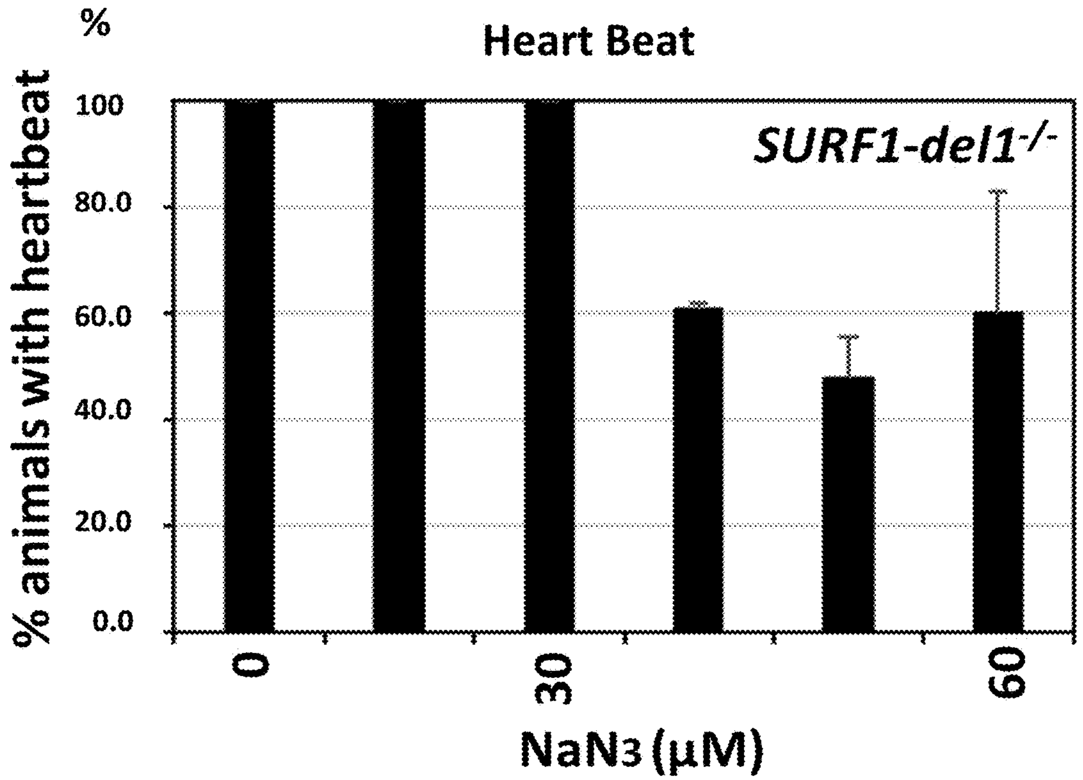
Fig. 23B

Fig. 24A
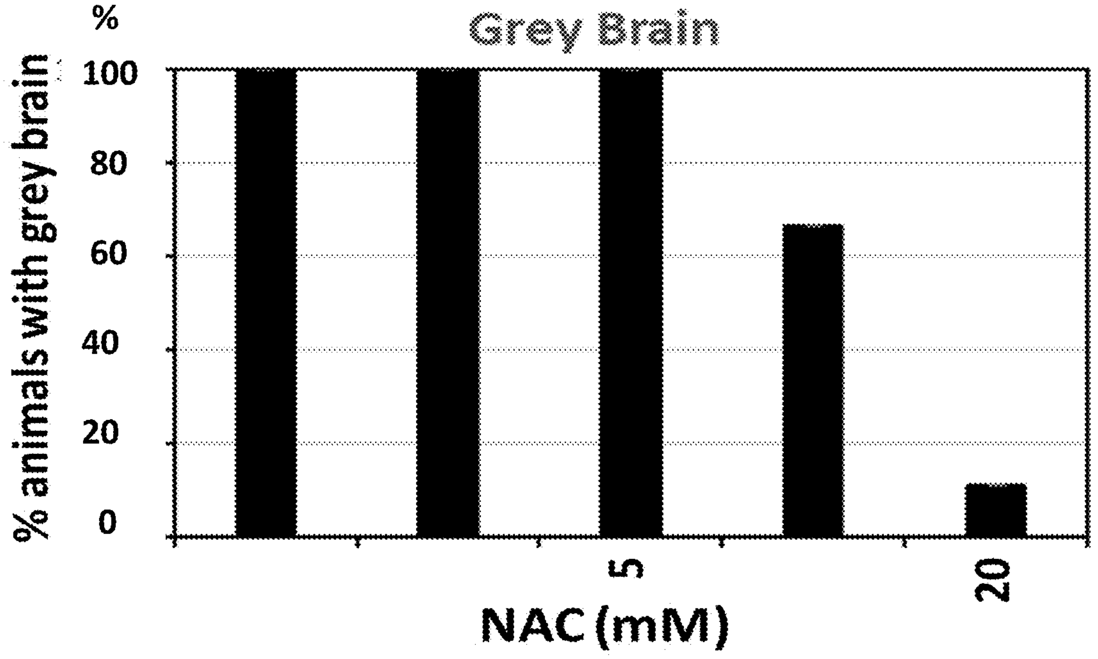
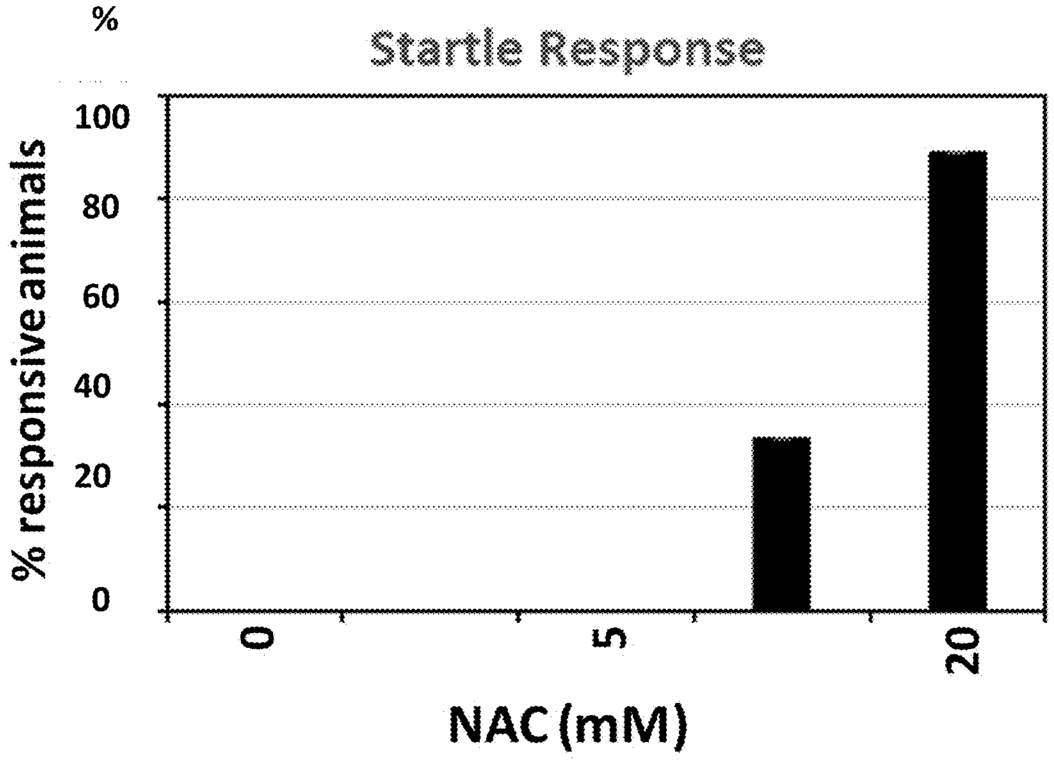
Fig. 24B

Fig. 24C
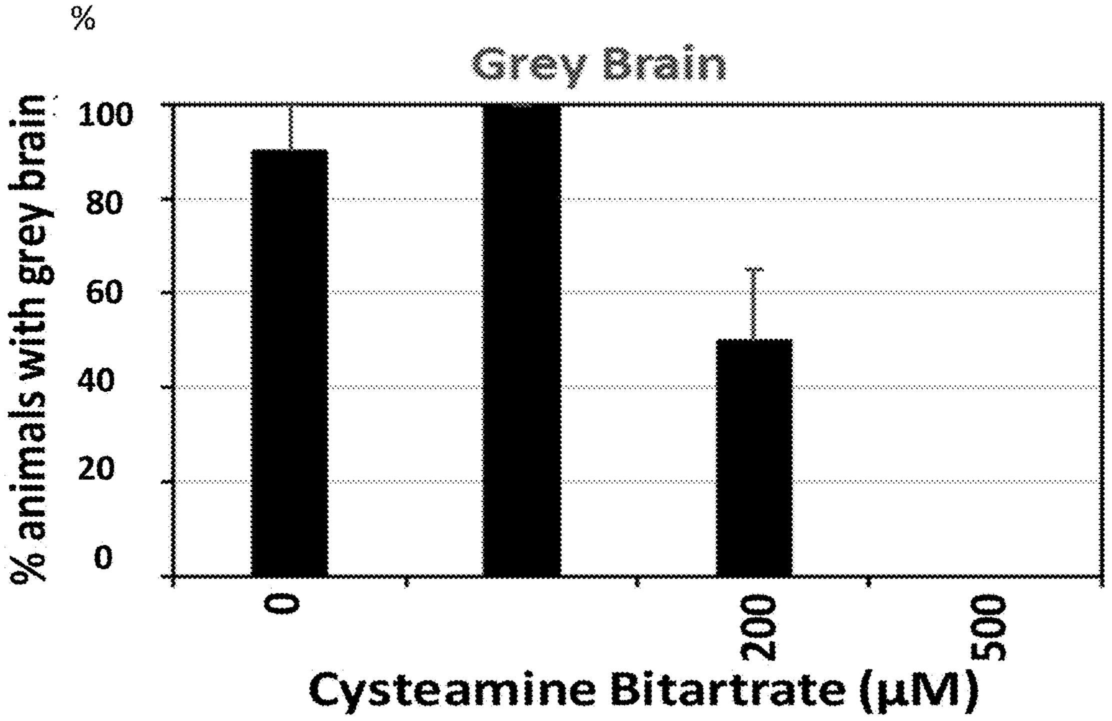
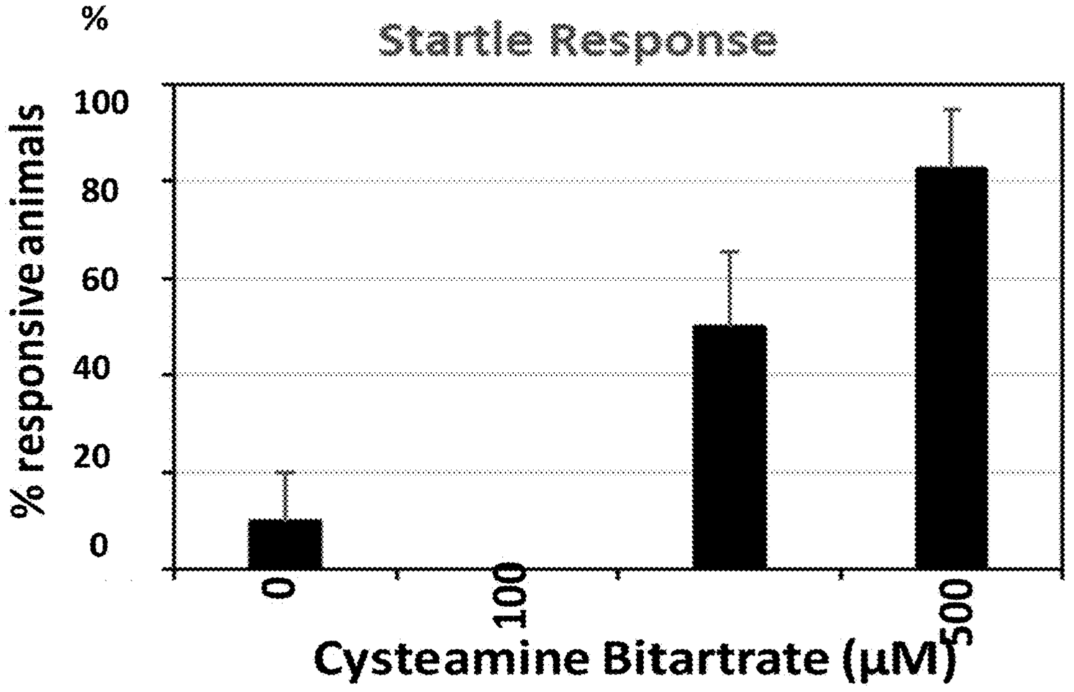
Fig. 24D

Synergistic effect on lifespan only observed with Glu+NA+NAC

Zebrafish screening of relative therapeutic effects on individual organs

Sodium Azide-stressor

NAC + 25 µ $NaN_3$

NAC + NA & NAC + GLU

Partially restored globally

Decreased gene expression after 24 hour treatment

COMPOSITIONS AND METHODS FOR TREATMENT OF MITOCHONDRIAL RESPIRATORY CHAIN DYSFUNCTION AND OTHER MITOCHONDRIAL DISORDERS

CROSS-REFERENCE TO RELATED APPLICATIONS

This application is a continuation of U.S. application Ser. No. 17/256,406, filed Dec. 28, 2020 which is a § 371 of International Application No. PCT/US2019/039631, filed Jun. 27, 2019, which claims priority to U.S. Provisional Patent Application Nos. 62/690,718 and 62/830,850, filed Jun. 27, 2018 and Apr. 8, 2019, respectively, the entire contents of each being incorporated herein by reference as thought set forth in full.

CROSS-REFERENCE TO RELATED APPLICATIONS

This application is a § 371 of International Application No. PCT/US2019/039631, filed Jun. 27, 2019, which claims priority to US Provisional Patent Application Nos: 62/690,718 and 62/830,850 filed Jun. 27, 2018 and Apr. 8, 2019 respectively, the entire contents of each being incorporated herein by reference as thought set forth in full.

GOVERNMENT SUPPORT CLAUSE

This invention was made with government support under grant numbers, RO1-GM120762-08, R01-HD-065858, P30-HD-026979, R03-DK-082521, T32-GM-008638, T32-NS-007413 awarded by The National Institutes of Health. The US government has certain rights in the invention.

FIELD OF THE INVENTION

This invention relates to the fields of physiology and mitochondrial disease. More specifically, the invention provides compositions and methods effective to develop and optimally, ameliorate symptoms of mitochondrial disease in human subjects. Also provided are screening methods for identifying novel and potent therapeutic agents and effective protocols for the treatment of mitochondrial disease in simple model animals (*C. elegans* worms, *D. rerio* zebrafish, *M. musculus* mice), and in human cells.

BACKGROUND OF THE INVENTION

Several publications and patent documents are cited throughout the specification in order to describe the state of the art to which this invention pertains. Each of these citations is incorporated herein by reference as though set forth in full.

Mitochondrial disease results from malfunctions in mitochondria, the energy-generating "batteries" powering our cells. The disease is highly variable and may affect potentially any organ and body system. Given the lack of validated treatments, many patients take vitamins and supplements on an "empiric" basis, relying on the assumption that this somehow in a vague and difficult to quantify fashion benefits their altered cellular metabolism and overall health. Unfortunately, most of these compounds are currently unregulated, unstandardized and untested, and have not been compared with one another or optimized to determine which may be the most safe, potent and effective in any given type of mitochondrial disease.

Complex I deficiency is the most frequently encountered single mitochondrial respiratory chain enzyme deficiency in patients with a mitochondrial disorder. Although specific genotype-phenotype correlations are very difficult to identify due to extensive pleiotropy, locus heterogeneity, and allelic heterogeneity, the majority of patients present with neurologic or muscular symptoms such as metabolic stroke, leukodystrophy, fatigue, exercise intolerance, myopathy, vision loss, and hearing loss. The average mitochondrial disease patient suffers up to 16 symptoms, which can be highly variable in onset and severity, but often induced or exacerbated by stressors that can lead to severe morbidity or death. The poor genotype-phenotype correlations can make establishing a diagnosis a challenge. The classical way to establish a respiratory chain complex(es) deficiency in patients is by performing polarographic and/or spectrophotometric measurements of the enzyme in a muscle biopsy or other patient-derived material (liver or heart biopsy, cultured skin fibroblasts). Complexes I, III, IV, and V are encoded by both mitochondrial DNA (mtDNA) and nuclear DNA. Pathogenic mutations have been identified in many different structural subunits of the respiratory chain, respiratory chain assembly factors, mtDNA-encoded transfer or ribosomal RNAs, and a host of nuclear genes effecting nucleotide metabolism, mitochondrial DNA replication and repair, oxidative stress, and mitochondrial dynamics such as fission and fusion. In recent years, the increasing possibilities for diagnostic molecular genetic tests of large gene panels, exomes, and even entire genomes has led to the identification of many novel genetic defects causing respiratory chain disease, with more than 350 genes now known to play a causal role in every possible Mendelian or maternal inheritance pattern. Respiratory chain complex disorders not only result in a reduced enzyme activity, impaired mitochondrial membrane potential and oxygen consumption capacity, mitochondrial morphology, energy generation in the form of adenosine triphosphate (ATP), altered redox balance of nicotinamide dinucleotide (NADH, NAD+) metabolism, but also induce secondary effects at the cellular level, such as globally disrupted signaling pathways. Those particularly affected involve the nutrient-sensing signaling network, increased autophagy and mitophagy, increased cytosolic translation, increased lysosomal numbers, and globally elevated reactive oxygen species production. Also common is glutathione depletion, along with a wide range of secondary intermediary metabolic alterations, stressor sensitivity, oxidative stress, proteotoxic stasis and stress, and cell death. At this moment there are no demonstrated safe and effective therapies nor cure for mitochondrial respiratory chain diseases, and treatment options for mitochondrial respiratory chain disease patients are limited to stress avoidance and symptom treatment.

It is clear that there is a need in the art for improved therapeutics and treatment protocols for this, and other mitochondrial diseases in general and in particular, mitochondrial respiratory chain disorders.

SUMMARY OF THE INVENTION

In accordance with the present invention, a composition having efficacy for the treatment of mitochondrial disease, comprising effective amounts of at least glucose, N-acetylcysteine, and nicotinic acid in a pharmaceutically acceptable carrier is disclosed. In certain embodiments, the glucose, N-acetylcysteine, nicotinic acid and probucol are administered separately. Cysteine bitartrate may optionally be included. In other embodiments, the glucose, N-acetylcysteine, nicotinic acid and probucol are administered together.

In another aspect, a method for alleviating symptoms associated with mitochondrial disease is provided. An exemplary method comprises administration of glucose, N-acetylcysteine, and nicotinic acid and/or probucol to a subject in need thereof. In certain embodiments, the symptoms include one or more of muscle weakness, exercise intolerance, chronic fatigue, gastrointestinal dysmotility, impaired balance, peripheral neuropathy, metabolic strokes, dysautonomia, vision loss, eye muscle and eyelid weakness, hearing loss, glomerular or tubular renal disease, endocrine dysfunction, dyslipidemia, cardiomyopathy, arrhythmia, anemia, failure to thrive, over or underweight, developmental delay, neurodevelopmental regression, cognitive decline and memory impairment, Parkinsonism, dystonia, liver dysfunction or failure, infertility, metabolic instability, stressor-induced acute decompensation, DLD disease, Mitophagy disorders, Mitochondrial lipid biogenesis disorders, mitochondrial cofactor disorders, and secondary mitochondrial disorders including but not limited to resulting from toxins, drugs, age, prescribed or illicit medications, smoking, alcohol, environmental exposures, obesity, and other primary genetic disorders that secondarily impair mitochondrial function, structure, or activities.

The compositions and methods of the invention can be used to advantage to treat a mitochondrial disease selected from the group consisting of Complex I disease, Complex II disease, Complex III disease, Complex IV disease, Complex V disease, Multiple respiratory chain complex disease, adenine nucleotide translocase deficiency, pyruvate dehydrogenase deficiency, mitochondrial depletion disease, multiple mitochondrial DNA deletions disease, mitochondrial DNA maintenance defects, mitochondrial translation defects, mitochondrial nucleotide import disease, Friedreich's ataxia, Leber's Hereditary Optic Neuropathy, Kearns-Sayre Syndrome, Pearson Syndrome, Mitochondrial Myopathy, Mitochondrial Encephalomyopathy with Lactic Acidosis and Stroke-Like Episodes, Myoclonic epilepsy and ragged red fibers, Neurogenic Ataxia and Retinitis Pigmentosa, Mitochondrial Neuro-gastrointestinal encephalomopathy, maternally inherited diabetes and deafness, primary lactic acidosis, Leigh syndrome, Leigh-like syndrome, and multi-system mitochondrial disease.

In another embodiment of the invention, a screening method for identifying agents which modulate mitochondrial respiratory chain dysfunction is provided. An exemplary method entails providing genetically altered *C. elegans*, the genetic alteration impacting a gene associated with mitochondrial respiratory chain dysfunction, and wild-type *C. elegans*, lacking the alteration; contacting the *C. elegans* from step a) with an agent; and determining whether the agent alters a cellular parameter associated with mitochrondrial function in *C. elegans* comprising said genetic alteration relative to wild type *C. elegans*; agents which alter said parameter in said genetically altered *C. elegans* being identified as modulators of mitochondrial respiratory dysfunction. The cellular parameters to be assessed include for example, fecundity, egg hatching rate, development, lifespan, stressor survival, healthspan, animal activity, swimming capacity, pharyngeal pumping rate, mitochondrial oxidant burden, cellular oxidant burden, antioxidant capacity, CI enzyme activity, CI enzyme assembly, oxygen consumption capacity, ATP production, ATP levels, nicotinamide dinucleotide (NADH and NAD+) levels, (NADH and NAD+) ratio, NAD metabolism, mitochondrial membrane potential, mitochondrial content, mitochondrial structure, mitochondrial ultrastructure, mitochondrial unfolded protein response, mitochondrial import, mitophagy, autophagy, cytosolic translation activity, nutrient-sensing signaling profile, unfolded protein response activation, lysosomal number, lysosomal activity, proteasome number or activity, transcriptome-wide signaling, amino acid pathway profiles, intermediary metabolic flux rates, steady state metabolism of intermediary metabolites, amino acid levels, organic acid levels, ammonia levels, and glycoprotein production, cellular proliferation, cell growth, lactic acid level, glycolysis, cellular redox levels, and lactate/pyruvate ratio.

The *C. elegans* may have a naturally occurring mutation, a chemically induced mutation, or the alteration may be generated via introduction of a silencing RNA or antisense oligonucleotide that targets a gene that modulates mitochondrial function. Genetic alterations can also be introduced using the CRISPR-CAS 9 gene knock out and knock-in system.

In another embodiment, the screening method further comprises contacting a zebrafish comprising a mutation in the cognate zebrafish gene with the identified agent and determining whether said agent alters a cellular parameter associated with mitochondrial dysfunction in said zebrafish. In yet another aspect the invention can further comprise contacting a human fibroblast, lymphoblastoid cell line, or derived iPSC or differentially terminated cell line comprising a mutation in the cognate human gene with the identified agent and determining whether said agent alters a cellular parameter associated with mitochondrial dysfunction in said human fibroblast. The method may also include incubation of *C. elegans* with a stressor prior to, along with, or after, exposure to the putative therapeutic agent(s).

In yet another aspect, the method entails screening zebrafish initially, then screening *C. elegans* and human cells with effective therapeutic agents identified in zebrafish. In alternative approaches, human cells can initially be screened followed by analysis in *C. elegans* and zebrafish. When screening zebrafish, cellular parameters to be assessed, include, without limitation, fecundity, egg hatching rate, development, lifespan, stressor survival, healthspan, animal activity, swimming capacity, pharyngeal pumping rate, mitochondrial oxidant burden, cellular oxidant burden, antioxidant capacity, CI enzyme activity, CI enzyme assembly, oxygen consumption capacity, ATP production, ATP levels, nicotinamide dinucleotide (NADH and NAD+) levels, (NADH and NAD+) ratio, NAD metabolism, mitochondrial membrane potential, mitochondrial content, mitochondrial structure, mitochondrial ultrastructure, mitochondrial unfolded protein response, mitochondrial import, mitophagy, autophagy, cytosolic translation activity, nutrient-sensing signaling profile, unfolded protein response activation, lysosomal number, lysosomal activity, proteasome number or activity, transcriptome-wide signaling, amino acid pathway profiles, intermediary metabolic flux rates, steady state metabolism of intermediary metabolites, amino acid levels, organic acid levels, ammonia levels, and glycoprotein production, cellular proliferation, cell growth, lactic acid level, glycolysis, cellular redox levels, and lactate/pyruvate ratio.

In certain embodiments the genetic alterations occur in a gene selected from NDUFS2, NUBPL, FBXL4, C12ORF65, SURF1, and DLDH. In other embodiments, the genetic alterations are selected from NDUFS2 p.R290K; FBXL4 p.G356fs, p.Q597P; SURF1 p.R912W, NUBPL p.G56R; and DLDH p.E375K. Any other mitochondrial disease gene and/or mutation can be similarly studied, for example see any gene/mutation provided on the world wide web in the MSeqDR online data base at https://mseqdr.org.

In yet another aspect of the invention, a highperformance liquid chromatography-electron chemical detection (HPLC-ECD) assay for accurate quantitation of reduced GSH and oxidized GSSG glutathione levels in a biological sample is disclosed. An exemplary method comprises obtaining a biological sample to be tested; contacting said sample with an extraction buffer and optionally, a detergent, and homogenizing said sample; centrifuging said homogenized sample and removing any cellular debris; deproteinizing said sample and collecting supernatant; and subjecting said sample to HPLC-ECD, thereby quantifying said reduced GSH. For the assessment of oxidized GSSG glutathione levels in said sample, the following procedure can be performed. The sample is first reacted with N-ethylmaleimide (NEM) to remove free GSH, followed by deproteinization with metaphosphoric acid/methanol. Then, the excess amount of NEM is removed from the sample by chloroform extraction. The resultant upper layer which contains GSSG is transferred to a new tube and reduction of GSSG to GSH is achieved by the reaction with sodium borohydride/Tris (3-hydroxypropyl)phosphine (THPP)/Tris(2-carboxyethyl) phosphine (TCEP). In certain embodiments, the sample is first contacted with N-ethylmaleimide (NEM) to remove free GSH. In some embodiments, the sample is further contacted with sodium borohydride and extracted with chloroform to remove excess NEM. They can also be deproteinized using metaphosphoric acid.

The invention also includes a reiterative screening method for identifying agents effective to modulate a disease phenotype in at least three biological models of mitochondrial respiratory chain dysfunction. An exemplary method comprises providing genetically altered *C. elegans*, said genetic alteration impacting a gene associated with mitochondrial respiratory chain dysfunction, and wild-type *C. elegans* lacking said genetic alteration; contacting the *C. elegans* from step a) with an agent; determining whether said agent alters a cellular parameter associated with mitochrondrial function in *C. elegans* comprising said genetic alteration relative to wild type *C. elegans*; and identifying an agent which alters said cellular parameter in *C. elegans*; contacting genetically altered zebrafish comprising a cognate genetic alteration and zebrafish lacking said genetic alteration, with the agent identified in *C. elegans*; determining whether said agent alters a cellular parameter associated with mitochondrial function in zebrafish harboring said genetic alteration relative to wild type zebrafish and identifying an agent which alters said cellular parameter in both *C. elegans* and zebrafish; and contacting a human fibroblast, lymphoblastoid cell line, or derived iPSC or differentially terminated cell line, comprising a mutation in the cognate human gene with said identified agent in *C. elegans* and zebrafish and determining whether said agent alters a cellular parameter associated with mitochondrial dysfunction in said human fibroblast, lympholastoid cell line, or derived iPSC or differentially terminated cell line, thereby identifying an agent effective to modulate a disease phenotype in at least three biological models of mitochondrial respiratory chain dysfunction. In certain embodiments, at least one of said *C. elegans*, zebrafish and said human fibroblast, lymphoblastoid cell line, or derived iPSC or differentially terminated cell line is contacted with a stressor, prior to, after, or concomitantly with said agent. The cellular parameter to be assessed includes for example, fecundity, egg hatching rate, development, lifespan, stressor survival, healthspan, animal activity, swimming capacity, pharyngeal pumping rate, mitochondrial oxidant burden, cellular oxidant burden, antioxidant capacity, CI enzyme activity, CI enzyme assembly, oxygen consumption capacity, ATP production, ATP levels, nicotinamide dinucleotide (NADH and NAD+) levels, (NADH and NAD+) ratio, NAD metabolism, mitochondrial membrane potential, mitochondrial content, mitochondrial structure, mitochondrial ultrastructure, mitochondrial unfolded protein response, mitochondrial import, mitophagy, autophagy, cytosolic translation activity, nutrient-sensing signaling profile, unfolded protein response activation, lysosomal number, lysosomal activity, proteasome number or activity, transcriptome-wide signaling, amino acid pathway profiles, intermediary metabolic flux rates, steady state metabolism of intermediary metabolites, amino acid levels, organic acid levels, ammonia levels, and glycoprotein production, cellular proliferation, cell growth, lactic acid level, glycolysis, cellular redox levels, and lactate/pyruvate ratio.

The invention also encompasses a preclinical method for identifying mitochondrial disease subjects likely to respond to treatment for mitochondrial dysfunction. On exemplary method comprises provide patient cell lines or cells from said subject, said subject having a predetermined genotype; contacting said cells with at least one agent; culturing said cells under normal and stressed growth conditions, wherein said stressor is applied in increasing concentrations; and determining the protective effects of said agent on said cells, agents having protective action being effective in subjects having said predetermined genotype. In certain embodiments, tolerability and efficacy of said agent are assessed in a whole animal model of mitochondrial dysfunction. In some embodiments, the cells are contacted with said agent for a time period of between one hour, 2 hours, 5 hours, 1 day, 2 days, 3 days, 4 days, up to 7 days. In some embodiments, the cells are contacted with the stressor for a time period of between one hour, 2 hours, 3 hours, 4 hours, 1 day, 2 days, 3 days, up to four days. Protective effects determined include one or more of improvement in cell viability, cell proliferation, ATP production, mitochondrial membrane protection mitochondrial mass, mitochondrial content, total cellular oxidant levels, cellular pH and oxygen capacity consumption.

BRIEF DESCRIPTION OF THE DRAWINGS

FIGS. 1A-1E. Grow delay and body length. 15-20 Adults were selected from both N2 (ctrl) and fbxl-1 worms. After 3 hours ~15-20 eggs were randomly chosen to assess grow delay. At Day 4 fbxl-1 (ok3741) showed a grow delay of ~10-18 hours. On day 4, all N2 worms were adult or gravid (FIG. 1A), while fbxl-1 worms were detected at stage L4 (FIG. 1B). fbxl-1 *C. elegans* length (FIG. 1D) is slightly reduced compared to N2 (FIG. 1C): 619±60 μm vs 696±64 μm (mean±SD); n=10; *p<0.05 (FIG. 1E).

FIG. 5A) Plates were scanned twice on day 4 and brood size analysis was obtained by analyzing the difference in pixels of the skeletonized images. FIG. 5B) N2 worms brood size is not affected after exposure to DCA (data not shown). The difference image score was normalized using a "percent of control" method to derive a normalized WormScan score. Decrease in fbxl-1 brood size compared to N2 is confirmed: 19±2 (Mean±SEM, n=35) vs 100±7.12 (n=38); **p<0.0001. Fbxl-1 brood size is significantly rescued by 25 mM DCA: 74.04±6.5 in fbxl-1 treated worms (n=57) vs 18.77±2.078 (n=35) untreated ones (**p<0.0001).

FIGS. 6A-6I. Stress and DCA treatment assay: light microscopy analysis. FIG. 6A-C) Control fibroblasts morphology is maintained after 24 and 48 hours exposure to glucose/uridine-free media and after treatment with 20 mM DCA. FIG. 6D) FBXL4 proband fibroblasts' morphology in culture medium is comparable at baseline to healthy controls (FIG. 6A). FBXL4 proband fibroblasts' morphology is affected by 24 hours of exposure to glucose/uridine-free media (FIG. 6E) which is mostly rescued by exposure to 20 mM DCA (FIG. 6F). FIG. 6G) After 48 hrs, stressed proband fibroblasts mostly show round shapes indicating active apoptosis and detachment. FIG. 6H) 20 mM DCA mostly rescues fibroblasts morphology: cells are elongated and well attached to the bottom of the dish; morphology is comparable to both FBXL4 proband and control fibroblasts in control medium (FIG. 6A, 6D).

FIGS. 7A-7C. Confocal microscopy of FBXL4 fibroblasts. Confocal live imaging of mitochondria stained with mitotracker green, did not show obvious differences between mitochondria in proband fibroblasts FIG. 7B) compared to control FIG. 7A). Immunostaining of proband mitochondria with TOM20 antibody (red) and nuclei staining with DAPI (blue, FIG. 7C) was performed to ensure that mitochondria morphology is comparable to the one detected using live imaging approach.

FIGS. 8A-8F. Fluorescence microscopy analysis of FBXL4 proband mitochondria after induced stress and DCA treatment. Live imaging shows that mitochondria are slightly affected by exposure to glucose/uridine-free media (FIG. 8A; FIG. 8D) after 24 hrs and 48 hrs of exposure if compared to fibroblasts in control media (FIG. 8B). Mitochondria aggregation and fragmentation is observed in some unhealthy cells (FIG. 8B). Exposure to 20 mM DCA for 24 hrs partially preserves mitochondrial damage (FIG. 8C). After 48 hrs, most cells show mitochondria fragmentation and aggregation (FIG. 8E). Most FBLX4 cells are rounded indicating active apoptosis (FIG. 8F).

FIG. 9E, e) Control cells and mitochondria structure is maintained after treatment with 20 mM DCA. FIG. 9F, f) FBXL4 cell damage is prevented and mitochondria ultrastructure rescued after 48 hrs exposure to 20 mM DCA. FIG. 6B shows a cell viability prototype screening plate design.

FIG. 11A) was compared against the CI mutant NDUFS2 (FIG. 11B) and the F0 NUBPL (FIG. 11C) in-cross. NUBPL displays a reduction in CI activity of 20% compared to AB. It is worth noting that NUBPL has a greatly reduced C2 activity of 80%. This is data was obtained based on 30 fish. Outcrossing could be done in further assays. FIG. 11D) Glucose and N-acetylcysteine improve lifespan in a genetic *C. elegans* $NUBPL^{-/-}$ model of Complex I disease.

FIG. 12. Lifespan analysis of WT (N2) and heterozygous dld-1 mutant *C. elegans*. Lifespan analysis was started at L4 larval stage and worms were monitored for survival daily by response to touch in the head and tail regions. Triplicate analysis was performed, n=30 worms/replicate. (FIG. 12B) Activity analysis was carried out by blue light stimulation of worms. Images were taken at two time points and pixels changed were measured. Analysis was carried out in triplicate with n=~40 worms per replicate. Mean and SEM are shown. *, p<0.05.

(FIG. 13A) Schematic of dldh CRISPR guide RNA. DldhsgRNA 3 targets Exon 1 of zebrafish DLDH gene. PAM sequence is indicated in red font. Successful deletion removes a MSII restriction enzyme site. Blue arrows indicate DLDH forward and reverse primers used to amplify a 300 bp segment of Exon 1. (FIG. 13B) dldh-3 sgRNA CRISPR efficiency. Dldh-3 sgRNA and Cas9 protein were injected into freshly fertilized AB (WT) embryos at 1 hpf. DNA was extracted from larvae at 7 dpf. PCR product with DLDH forward and reverse primers subsequently digested with MSII. 100% bi-allelic (homozygous) deletion was observed. Sanger sequencing dldh CRISPR larvae. A dldh mutant allele of a 7 bp deletion, resulting in a premature stop codon in the DLDH protein was identified. (FIG. 13C) Immunoblot of 7 dpf zebrafish. 30 μg control and dldh larvae lysate was loaded and probed with anti-DLD antibody and α-Citrate Synthase antibody, confirming the dldh deletion in the CRISPR-generated knockout fish.

FIGS. 14A-14D. dldh−/− Zebrafish display enlarged liver and failure to thrive. FIG. 14A. Control and dldh CRISPR injected Zebrafish Larvae lateral viewed at 1.6× magnification. dldh−/− larvae show swollen liver and deflated swim bladder compared to wild-type controls at 8 dpf. FIG. 14B. Survival analysis comparing control and dldh−/− zebrafish, N=30 larvae for each group. Death was defined by absence of a heartbeat. FIG. 14C shows control zebrafish before and after treatment of 100 nM Rotenone. FIG. 14D shows that the combination of glu+NA+NAC prevents brain death.

FIG. 15A) Lipid accumulation in dldh−/− Zebrafish liver. Oil Red O staining of control and dldh−/− larvae at 7 dpf at 1.6× (left) and 6.8× (right). dldh−/− larvae shows oil Red O staining in the liver compared to controls. FIG. 15B) Electron micrograph shown accumulation of lipids.

FIG. 16A. Electron transport chain Complex IV enzyme activity analysis of zebrafish lysate at 6 dpf and 7 dpf. Each bar represents 2 biological replicates of ~30 larvae. Values are normalized to citrate synthase. Bars indicate mean and standard deviation. (FIG. 16B. EM analysis of tail muscle in control and dldh−/− larvae at 7 dpf. EM micrographs show degenerating mitochondria (M) in and dldh−/− larva compared to controls. dldh−/− mitochondria are swollen with loss of mitochondrial matrix density and possible cristae damage, while mitochondria structure is preserved in wild-type controls.

FIGS. 17A-17D: (FIG. 17A) Immunoblot analysis of worms fed control plasmid (L4440) and dld-1 RNAi (LLCI.3), 30 μg of whole worm lysate was loaded and immunblot was probed with anti-DLD antibody and α-tubulin was used as a loading control. (FIG. 17B) Brood size analysis of control and dld-1 RNAi worms. Graph represents the average of 4 independent experiments $P<0.005$. (FIG. 17C) Images displaying size of control worms (Left) compared to dld-1 RNAi worms (right), magnification at (1.6×). (FIG. 17D) Measurement of worm size over time (TOF represents length and Extinction represents width). Analysis performed using the COPAS Biosorter (Union Biometrica).

(FIG. 18A) Transgenic hsp-6p::GFP reporter strain was fed Control (L4440) and dld-1 (LLCI.3) RNAi. Left: Control and dld-1 RNAi worms viewed at 10× bright field image and GFP channel. FIG. 18B) Chemoattractant motility assay for neuromuscular function. 30 control and dld-1 RNAi worms were spotted on a plate 5 cm from a chemoattractant. The position after one hour was measured and analyzed via Image J. Graph represents three technical replicates for each group. *$P<0.05$. *$P<0.0005$. (FIG. 18**C): High content analysis of GFP fluorescence utilizing the COPAS biosorter. N=200 worms for each group. $P<0.0005$.

FIGS. 19A-19B. (FIG. 19A) Therapeutic efficacy of 25 mM dichloroacetate (DCA) and 25 mM Thiamine on mitochondrial stress (induction of hsp-6p::GFP). Worms fed Control or dld-1 RNAi were treated with the therapies from birth and fluorescence intensity of the GFP signal was analyzed at adult day 1 as described above. (FIG. 19B) Therapeutic efficacy of 50 μM Riboflavin and 25 mM Thiamine on animal size. Worms were treated with the therapies from birth and size was analyzed as described in FIG. 1D at adult day 1. *$P<0.005$, ***$P<0.0005$.

(FIG. 20A) Images were taken of larvae at 8 dpf and liver area was measured using Image J. $P<0.05$. (FIG. 20B) Survival analysis. Death was defined by absence of heartbeat.

FIGS. 23A-23D. SURF1del1−/− zebrafish are hypersensitive to CIV inhibition with $NaN_3$, developing neuromuscular dysfunctionWild-type zebrafish display reduced heartrate and neuromuscular (startle) response at 100 μM azide from 6-7 dpf (left panels), further exacerbated at higher doses. SURF1-del1−/− zebrafish show azide hypersensitivity, with bradycardia and impaired neuromuscular function (reduced startle response) starting at 40 μM azide.

FIGS. 24A-24D. SURF1del1−/− zebrafish pre-treatment with N-acetylcysteine (NAC) or cysteamine bitartrate preserves neuromuscular function in 45 μM $NaN_3$. SURF1-del1−/− zebrafish were pre-treated from 5 dpf with either NAC or cysteamine bitartrate, exposed to 45 μM $NaN_3$ from 6 dpf, and assessed on 7 dpf. FIGS. 24A and 24B show NAC pre-treatment prevented brain death and neuromuscular dysfunction (preserved startle response) from $NaN_3$ exposure. FIGS. 24C and 24D are graphs showing cysteamine bitartrate treatment also prevented brain death (FIG. 24C) and neuromuscular dysfunction (preserve startle response, FIG. 24D) from $NaN_3$ exposure.

FIG. 25A), and following 10 minutes of strobe light stress after which animals were allowed to recover in darkness for 20 minutes (right panel; FIG. 25B). SURF1-del2−/− zebrafish (red) displayed lower basal and post-stress activity and endurance relative to wild-type (AB) control zebrafish.

FIG. 32) Glucose+Nicotinic acid+N-acetyl cysteine. FIG. 32B) Resveratrol+Folinic acid+Cysteamine.

FIG. 36B) Wild-type (AB) fish are pre-exposed to drug treatments in their water from 5 days post fertilization (dpf) to 7 dpf. On 7 dpf, Zebrafish are co-treated with 150 nM of Rotenone (complex I inhibitor) and the same drug treatment(s). Zebrafish are then placed on the automated Zebrabox (Viewpoint) for 20 minutes of light at 60% followed by 20 minutes of darkness (eg, light at 0%) to induce a neurobehavioral startle response. The activity from the startle response is binned to 5 minute, and shown here as average activity at 581 minutes post-rotenone exposure. Activity score is normalized using percent of control (POC) to wild-type AB fish. These data represents mean of 3 independent biological replicates, with total of 24 zebrafish per condition. Error bars convey standard error of mean. *, $p<0.05$; , $p<0.01$; *, $p<0.001$ by Student's T test. Glu, 10 mM glucose. NA, 1 mM nicotinic acid. NAC, 2.5 mM N-acetylcysteine. FIG. 36D shows % with normal brain following treatment. FIG. 36D shows the protective effects of glucose, NA and NAC on the sodium azide treated (stressor) brains of surf1 KO zebrafish. FIG. 36D+36E. Protective effects of NAC on the rotenone treated (stressor) brains of zebrafish.

DETAILED DESCRIPTION OF THE INVENTION

Figure 1E:
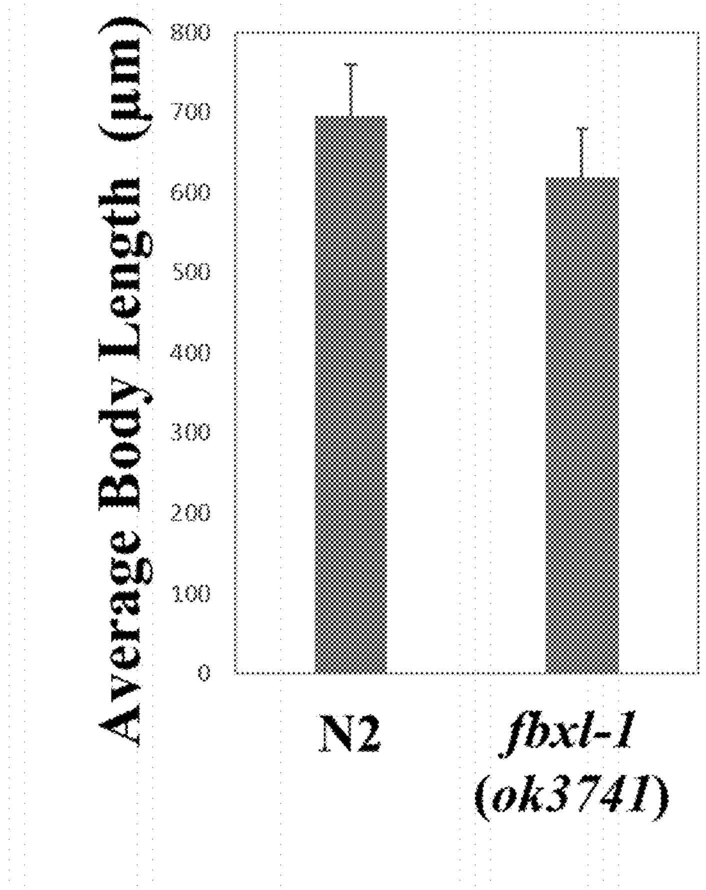
Figure 2A:
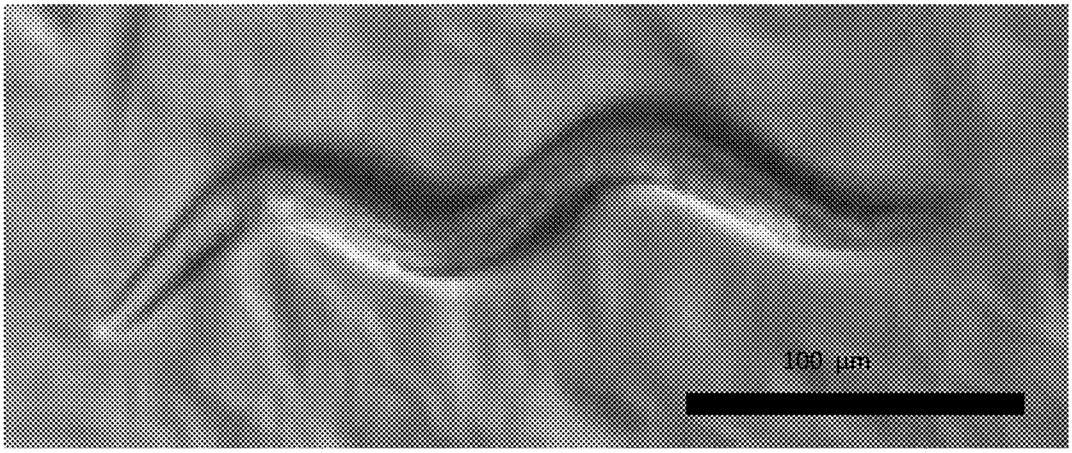
FIGS. 2A-2D. Neuromuscular activity: body bends and pharyngeal pump assay. Body bends/min was estimated by observing young adults movement as number of bends (FIG. 2A, arrows) during 3 minutes. Their neuromuscular function was impaired, with significantly reduced motility compared to N2: 5.0±2.3 vs 12.6±4.0; n=10; 2 replicates; *p<0.001 (FIG. 2B). Pharyngeal pump rate was measured counting the grinder contraction in the head of the worms (at day 4) when moving back and forth (FIG. 2C, from 1 to 3). Using oblique illumination contrast method, the rate was obtained by manually counting the bright spot at the 3th movement of the grinder (C3). The pharyngeal pump rate is significantly increased in fbxl-1 worms than in N2 worms (FIG. 2D): 310±24.5 vs 264±13.0; n=15; **p<0.0001.
Figure 2B:
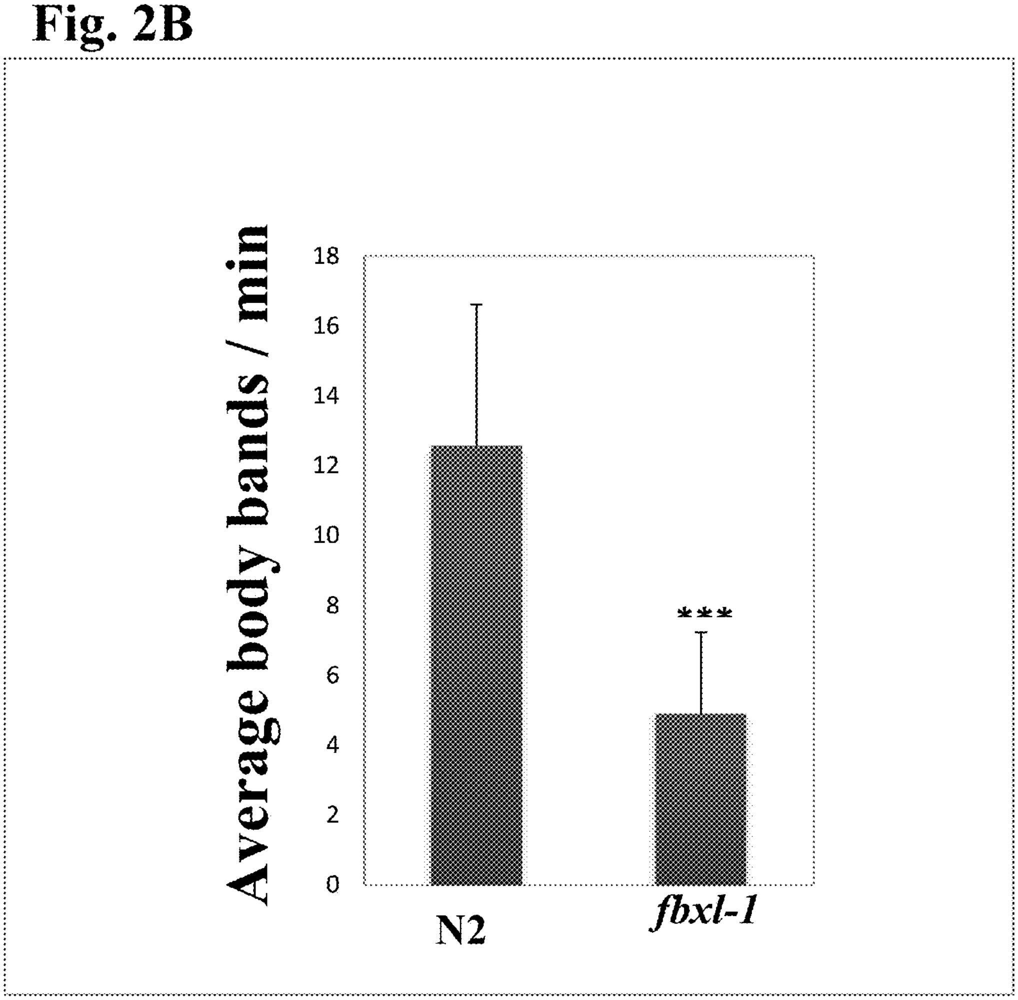
Figure 2C:
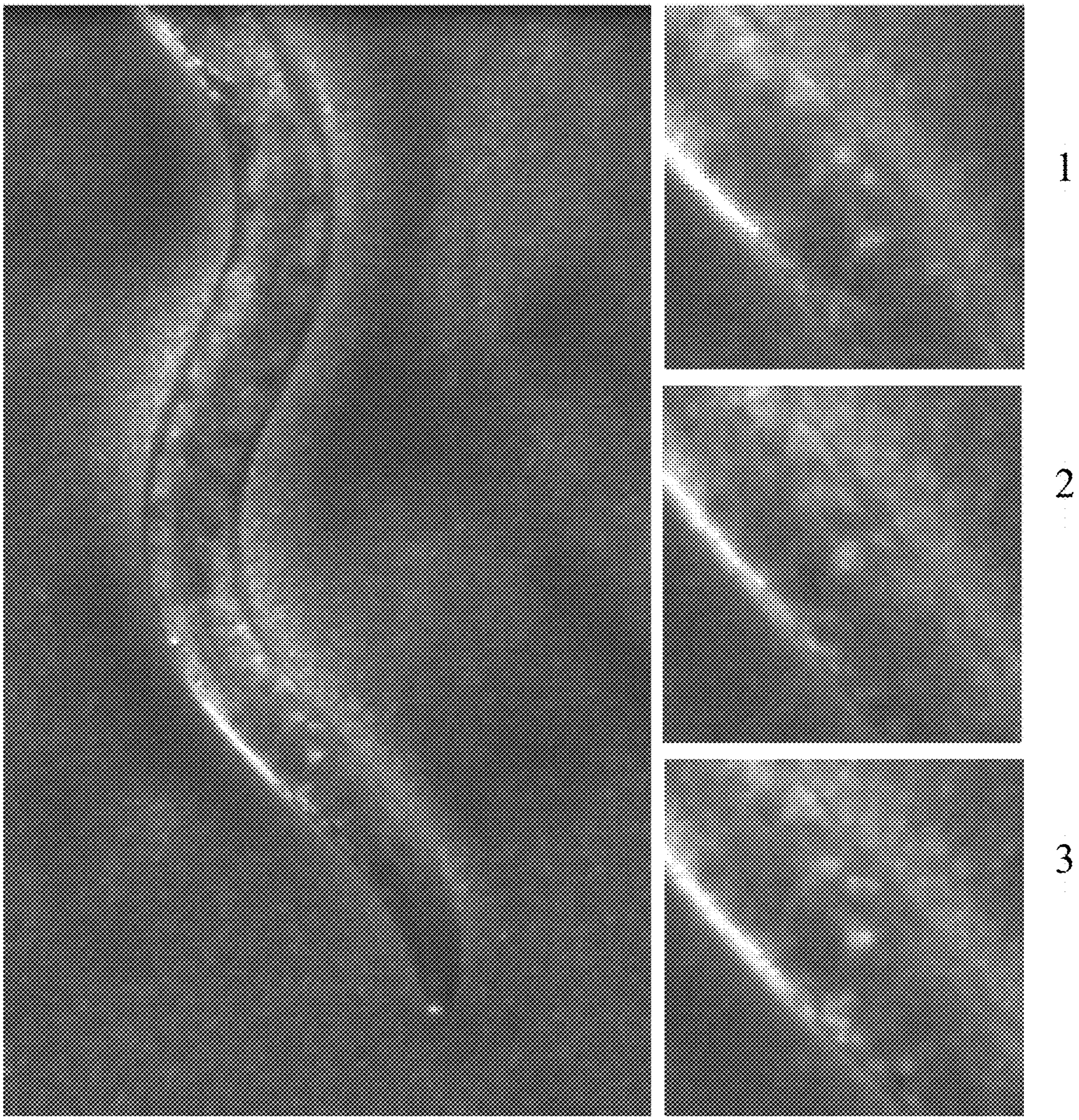
Figure 2D:
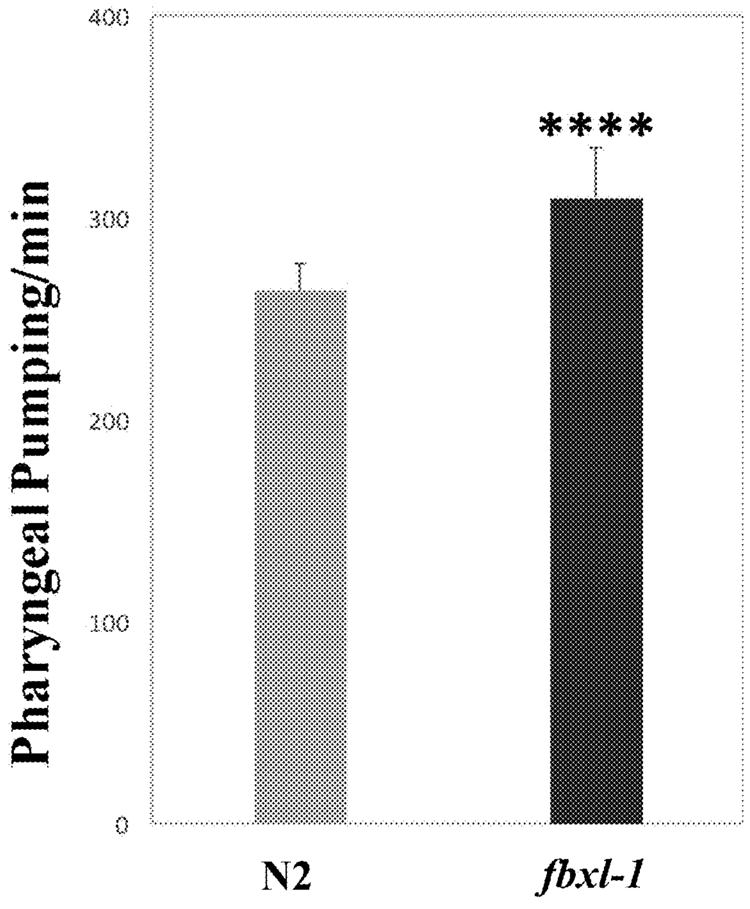
Figure 3:
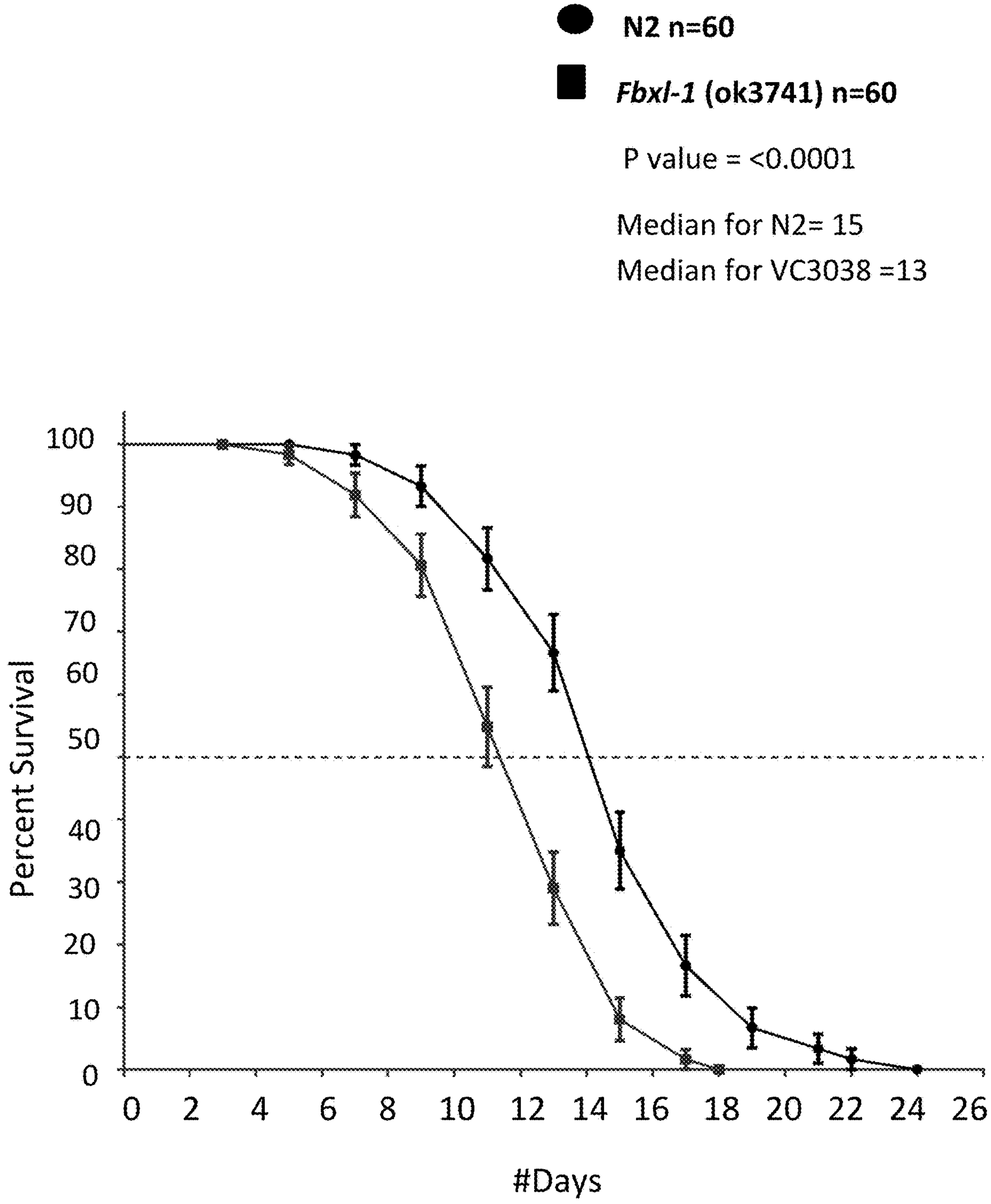
FIG. 3. *C. elegans* life span. fbxl-1 worms at 20° C. had significantly reduced survival (87% and 73% of wild-type N2 Bristol median and maximal lifespan respectively, p<0.0001). 2 replicates were obtained.
Figure 4:
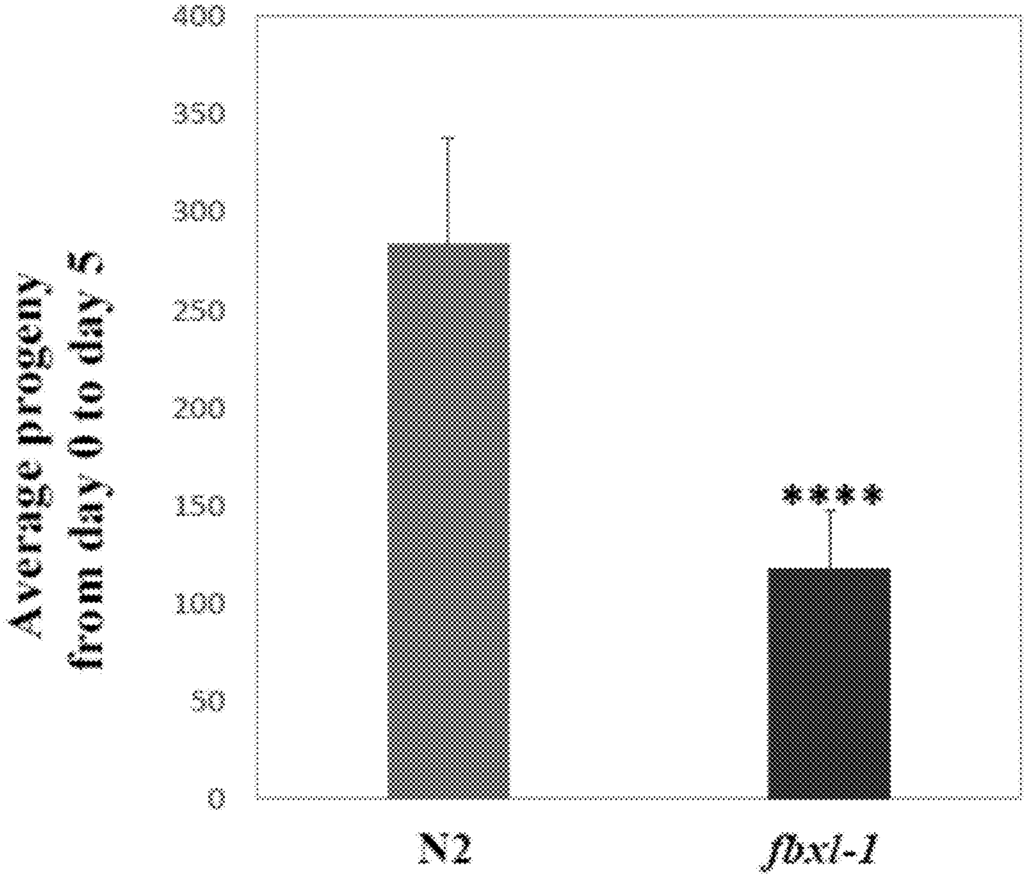
FIG. 4. Brood size. Manual brood size was estimated using adults worms (n=9 each strain) quantifying the number of eggs laid over the worm's reproductive lifetime (5 days). Manual brood size assay showed a decrease in progeny of >50% compared to N2: 117.11±30 vs 283.33±54; ****p<0.0001.
Figure 5A:
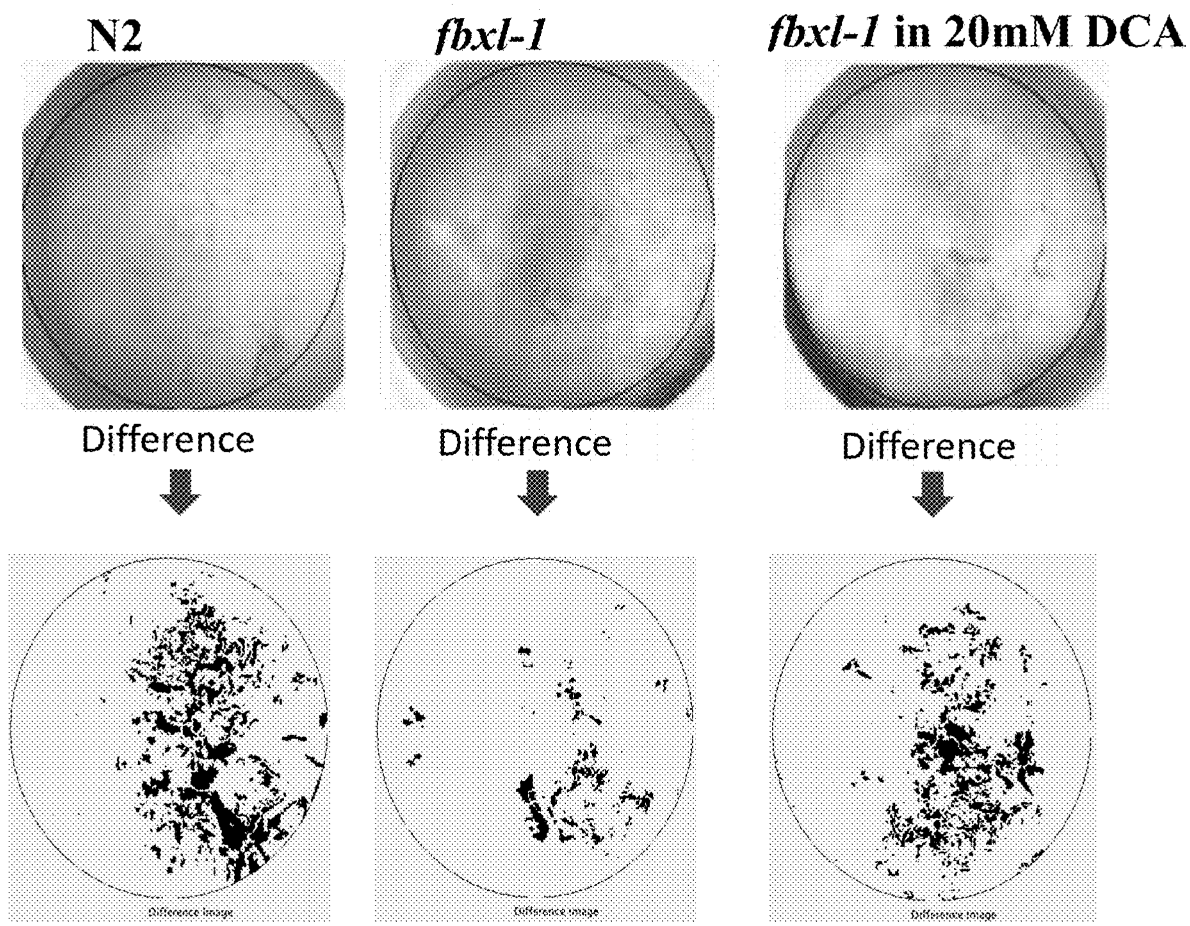
FIGS. 5A-5B. Brood size and treatment with DCA using WormScan. N2 and fbxl-1 adult worms were treated with 25 mM DCA for 4 days. Two worms were transferred to one well in a 96-wells plate with OP50 bacteria and with or without 20 mM DCA.
Figure 5B:
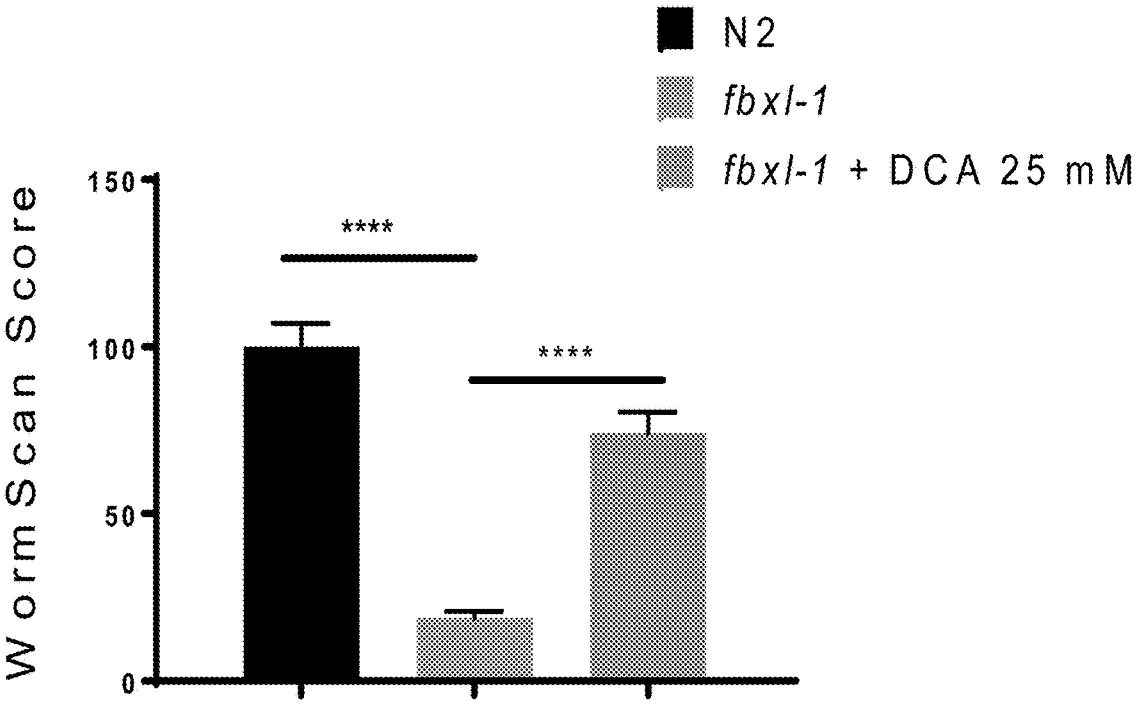
Figure 6I:
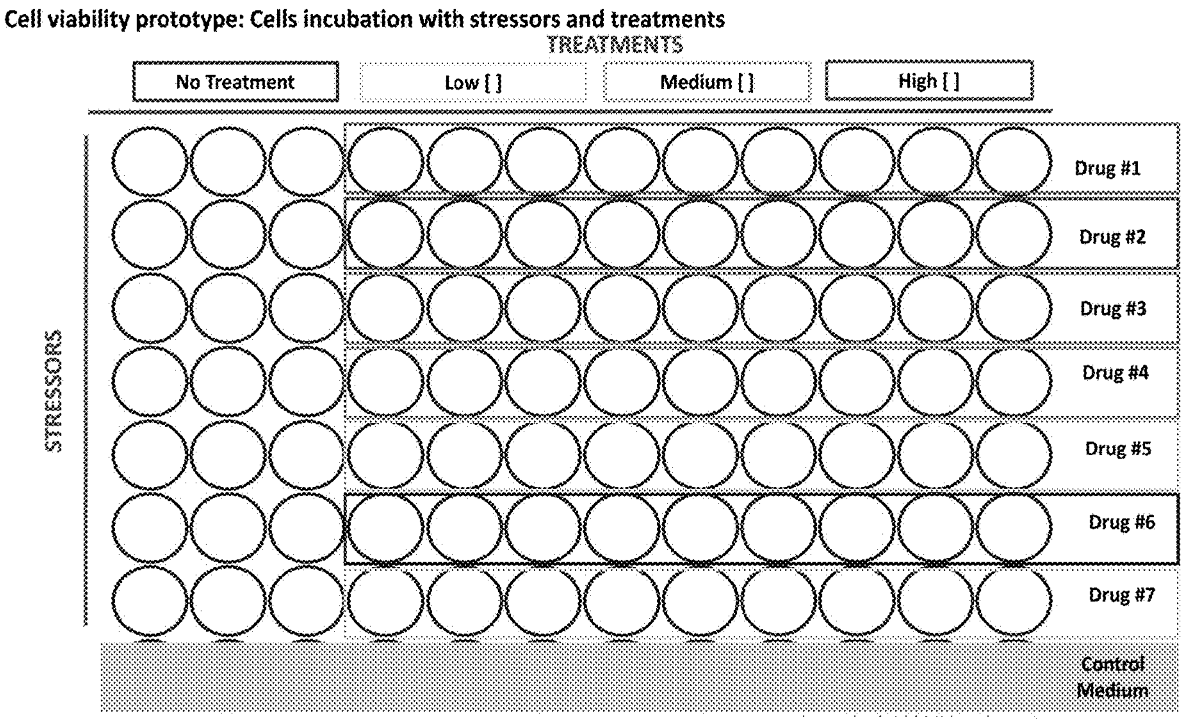
Figures 9A, 9B:
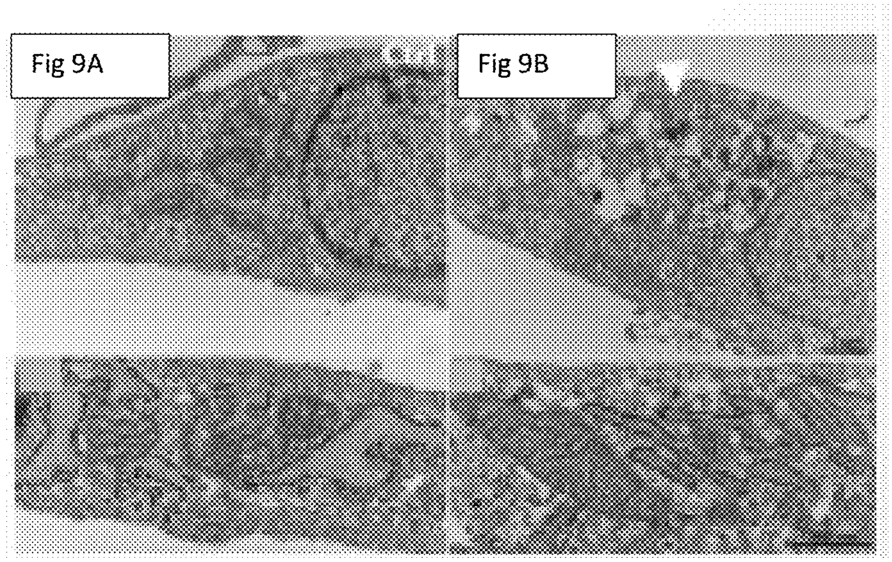
FIGS. 9A-9F. FBXL4 cells and mitochondria ultrastructure after treatment with DCA. Electron microscopy. FBXL4 proband fibroblasts and mitochondria ultrastructure (FIG. 9B, b) at baseline is comparable to the control (FIG. 9A, a) except for the higher frequency of lysosomes (FIG. 9B, arrow head) compared to control. After 48 hrs exposure to glucose/uridine-free media, fibroblasts ultrastructure and shape is critically damaged (FIG. 9D): cells are rounded, high frequency of lysosomes and general cell degeneration is detected. On the contrary, control cells ultrastructure is unaltered (FIG. 9C). In control cells mitochondria structure is maintained, showing electron-dense matrix and visible cristae (c) while in proband cells, mitochondria show loss of matrix density as mis-orientated cristae that are reduced in number (d).
Figures 9C, 9D:
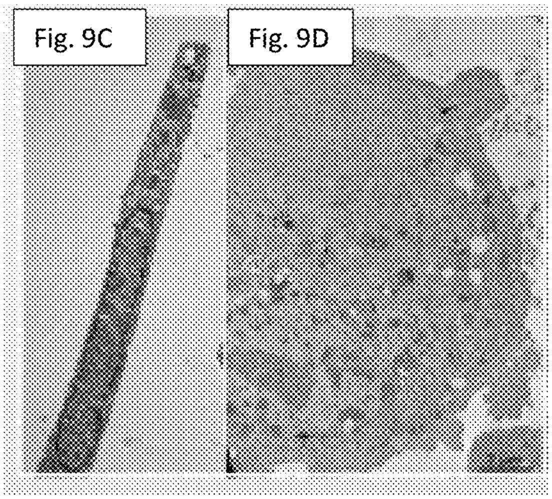
Figures 9E, 9F:
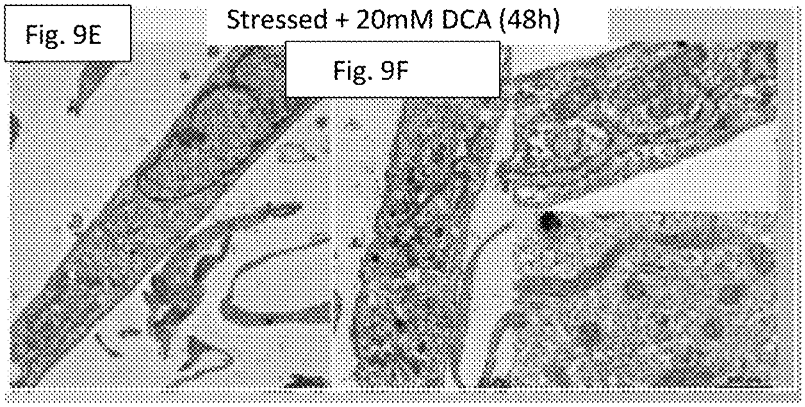
Figures 10A, 10B, 10C, 10D, 10E:
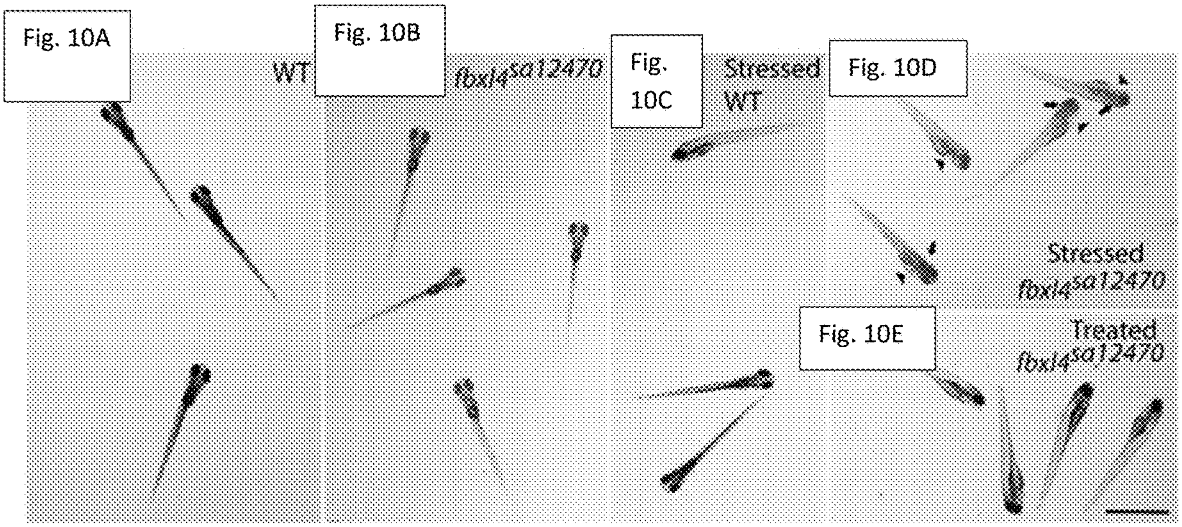
FIGS. 10A-10E. The results of DCA in a thrashing model in an fbxl4s@12470 zebrafish model is shown. fbxl4sa12470 larvae do not show any evident morphological defect in normal media conditions at 6 dpf. fbxl4sa12470 homozygous mutant larvae are more sensitive to RC stress, showing increased morphological defects than WT fish after exposure to 2.5 mM CMP, including grey brain (arrows), heart edema (arrow heads, generally not observed in WT), and overall body degeneration including muscle damage. Co-exposure of stressed fbxl4sa12470 larvae with CMP and 5 mM DCA slightly decreased morphological damage. Both stressed and treated fbxl4sa12470 larvae show developmental delay, with absent swim bladder; this was not rescued with DCA treatment. bar=1 mm.

Primary mitochondrial respiratory chain (RC) disease is highly heterogeneous in etiologies and phenotypes, with causal mutations now recognized in more than 350 different genes across both nuclear and mitochondrial genomes, following all Mendelian and maternal inheritance patterns. This new genomic understanding represents a transformative explosion in our understanding of mitochondrial RC disease etiologies and biochemical mechanisms. More than 5-fold increased identification of mitochondrial disease genes has occurred over the last decade, with likely hundreds more to be recognized—indeed, over half of causal gene disorders were identified in the past 6 years. Secondary mitochondrial RC dysfunction is also now widely recognized to occur in a host of common disorders, from neurodegenerative diseases such as Parkinson's and Alzheimers, to complex phenotypes like metabolic syndrome, aging, sepsis, and ischemia-reperfusion injury after cardiac arrest or stroke. Sharing the basic underlying phenomenon of energy failure, RC disorders involve an impressively diverse spectrum of functional deficiencies that clinically present across central, peripheral, and autonomic nervous systems, skeletal muscle, heart, gastrointestinal tract, kidney, vision, hearing, hematologic, endocrine, and immune systems. Remarkably, each mitochondrial disease patient suffers on average 16 (range 7-35) major medical problems, which may involve any organ(s) and onset at any stage in their lifespan from birth through old age. With a collective minimal prevalence of 1 in 4,300, mitochondrial disease inflicts high health care burden and cost.

To identify and, optionally optimize efficacious and non-toxic individual and multi-drug treatments for major respiratory chain (RC) disease subtypes, we have employed *C. elegans* and Zebrafish models of major RC disease. Lifespan screen in *C. elegans* gas-1(fc21) Complex I NDUFS2 subunit homozygous missense mutant worms has been completed by us using classical experimental methods for 13 triplicate combinations randomly selected by combining compounds we previously found to have individual efficacy at specific concentrations for improving gas-1(fc21) worm short lifespan that we classified into 3 major categories, namely antioxidants [N-acetyl cysteine (2.5 mM), vitamin E (250 uM), coenzyme Q10 (650 uM), lipoic acid (10 uM)], signaling modifiers [nicotinic acid (1 mM), resveratrol (500 uM), AICAR (500 uM), rapamycin (2.5 nM)], and intermediary metabolic modifiers [glucose (10 mM), thiamine (25 mM), riboflavin (10 uM), folinic acid, probucol (5-50 μM) (10 uM), dichloroacetate (25 mM)].

A novel FBXL4 (vc3038) knockout *C. elegans* strain has been characterized, as well as two novel, DLD-1 mutant animal models in *C. elegans* and zebrafish that display the classical hallmarks of mitochondrial and liver dysfunction that occur in human DLD disease (a rare form of pyruvate dehydrogenase deficiency). Assessments included lifespan analysis application of an integrated, rapid screen of worm development (WormScan).

The applicability of new treatment paradigms, specifically in mitochondrial DLD-based pyruvate dehydrogenase deficiency disease is also described herein. We have (a) established and characterized informative translational disease models, (b) used these models to objectively and efficiently screen the efficacy and toxicity of individual therapeutic agents that have been empirically used in DLD disease or shown promise in our prior mitochondrial disease models, and (c) identified optimal therapeutic combinations for use in personalized clinical trials in affected patients. These specific disease models include human fibroblasts from a DLD disease patient and parental controls, as well as *C. elegans* (invertebrate animal) and Zebrafish (vertebrate animal) models of DLD disease we have established. In certain approaches, paradigms can be established for precision therapeutic development for individual mitochondrial disease patients with distinct genetic etiologies, where therapies can first be prioritized in human patient cell and simple animal models (*C. elegans* and Zebrafish), and then lead therapeutic regimens showing greatest and most consistent efficacy in these models can be administered in an individualized ('n-of-1') treatment trial to objectively evaluate outcomes on overall well-being and organ-specific function in a child with DLD disease. Additional clinical trials can be performed to test new therapies that prove effective in individual patients in a larger number of patients with similar molecular genetic causes or types of biochemical deficiencies underlying their mitochondrial disease. Also described is a semi-automated *C. elegans* lifespan and healthspan system, WorMotel (Churgin M A et al, *eLife*, 2017, PMC5484621) is employed that utilizes blue light rather than manual prodding to assess worm viability. This approach allowed us to substantially increase lifespan analyses from one experiment every 4-6 weeks, to up to 10 lifespan experiments simultaneously in this same time period. This system also enables rapid and efficient screening of lead compounds in the other mitochondrial RC Complex mutants, including, for example, stable knock-out mutant *C. elegans* strains NDUFB3 (CI8E9.4) Complex I disease model and FBXL4 (C02F5.7, VC3038) allele as models of multiple RC complex disease. Prior work by us and others has shown that feeding RNA interference knockdown of complex I (NDUFBII), Complex IV (COXIV), and Complex V (COXVa) subunits each decreases worm lifespan. We have also contributed to optimization and statistical analysis of a new blue light based, robotic life span and heath span (activity) analysis system that concurrently analyzes 90×24 well plates simultaneously, where each well holds approximately 50 living worms.

In order to more accurately identify glutathione metabolite (GSH and GSSG) levels in a sample, we have now developed a novel HPLC-ECD assay which effectively measures GSH levels, with 100 times higher sensitivity compared to the standard enzymatic assay, exhibiting linearity over five digits. This system also enables specific measurement of GSSG, as well as the ratio of GSH:GSSH to inform reduced (active, GSH) to oxidized (inactive, GSSG) glutathione level.

Of 13 combination therapies selected from lead molecules we categorized into 3 common major categories, we identified a superior combinatorial treatment which shows synergy in extending lifespan in gas-1(fc21) mutant worms beyond that of wild-type control animals. A 24 hour treatment of these complex I disease worms with this 3-drug combination originally selected based on the top hits in each treatment class, namely glucose (Glu, a metabolic modifier), nicotinic acid (NA, a signaling modifier), and N-acetylcysteine (NAC, an antioxidant) of young adult gas-1(fc21) worms significantly improved their reduced in vivo mitochondrial membrane potential, but not their reduced mitochondrial content. Interestingly, Glu+NAC 24 hour treatment significantly rescued their reduced in vivo mitochondrial membrane potential (TMRE) but not mitochondrial content, while Glc+NA 24 hour treatment had the opposite effects and NA+NAC did not grossly resolve the altered mitochondrial physiology of gas-1(fc21) mitochondrial respiratory chain deficient worms.

Definitions

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, *C. elegans*, zebrafish, mice, rats, hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

A "genetic or protein alteration" as used herein, includes without limitation, naturally occurring mutations, chemically induced mutations, genetic alterations generated via introduction of siRNA, antisense oligonucleotides and CRISPR-CAS 9 targeted gene constructs. Protein alterations can be generated via pharmacological inhibition or modification of proteins involved in mitochondrial respiratory chain function.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented.

As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of a mitochondrial disease associated gene.

As used herein, "mitochondrial related disorders" related to disorders which are due to abnormal mitochondria such as for example, a mitochondrial genetic mutation, enzyme pathways etc. Examples of disorders include and are not limited to: loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection. The mitochondrial abnormalities give rise to "mitochondrial diseases" which include, but not limited to: AD: Alzheimer's Disease; ADPD: Alzheimer's Disease and Parkinsons's Disease; AMDF: Ataxia, Myoclonus and Deafness CIPO: Chronic Intestinal Pseudoobstruction with myopathy and Opthalmoplegia; CPEO: Chronic Progressive External Opthalmoplegia; DEAF: Maternally inherited DEAFness or aminoglycoside-induced Deafnness; DEMCHO: Dementia and Chorea; DMDF: Diabetes Mellitus & Deafness; Exercise Intolerance; ESOC: Epilepsy, Strokes, Optic atrophy, & Cognitive decline; FBSN: Familial Bilateral Striatal Necrosis; FICP: Fatal Infantile Cardiomyopathy Plus, a MELAS-associated cardiomyopathy; GER: Gastrointestinal Reflux; KSS Kearns Sayre Syndrome LDYT: Leber's hereditary optic neuropathy and Dystonia; LHON: Leber Hereditary Optic Neuropathy; LIMM: Lethal Infantile Mitochondrial Myopathy; MDM: Myopathy and Diabetes Mellitus; MELAS: Mitochondrial Encephalomyopathy, Lactic Acidosis, and Stroke-like episodes; MEPR: Myoclonic Epilepsy and Psychomotor Regression; MERME: MERRF/MELAS overlap disease; MERRF: Myoclonic Epilepsy and Ragged Red Muscle Fibers; MHCM: Maternally Inherited Hypertrophic CardioMyopathy; MICM: Maternally Inherited Cardiomyopathy; MILS: Maternally Inherited Leigh Syndrome; Mitochondrial Encephalocardiomyopathy; Mitochondrial Encephalomyopathy; MM: Mitochondrial Myopathy; MMC: Maternal Myopathy and Cardiomyopathy; Multisystem Mitochondrial Disorder (myopathy, encephalopathy, blindness, hearing loss, peripheral neuropathy); NARP: Neurogenic muscle weakness, Ataxia, and Retinitis Pigmentosa; alternate phenotype at this locus is reported as Leigh Disease; NIDDM: Non-Insulin Dependent Diabetes Mellitus; PEM: Progressive Encephalopathy; PME: Progressive Myoclonus Epilepsy; RTT: Rett Syndrome; SIDS: Sudden Infant Death Syndrome.

Screening Methods for Identifying Agents and Therapeutic Regimens Having Efficacy for the Treatment of Mitochondrial Disease Primary drug screening for novel agents can be performed in the *C. elegans* disease models described herein. Compounds can initially be screened using the high-throughput technique WormScan, which can quantify the phenotypical endpoints of brood size, changes in behavior/motility response and mortality. WormScan can screen compounds at a rate of ~1,900 compounds per hour, with a theoretical limit of >10,000 compounds per hour. The case and pace of primary screening of using this platform is unprecedented and has led to efficient identification of new compound leads, as described herein.

Once promising candidates are identified, secondary screens will be performed. The evolutionarily conserved model systems of primary complex I disease due to structural subunit or complex I assembly dysfunction will enable identification and optimization of a consistent lead therapeutic regimen to prioritize as precision medicine for neurodevelopmental dysfunction in complex I disease patients. Candidates identified in *C. elegans* (invertebrate animal model) are then confirmed in Zebrafish (vertebrate animal model) as well as human fibroblasts from a NUBPL disease (or other mitochondrial disease) patient and parental controls, for example. The data presented herein, based on a cross-model organism validation approach, coupled with human patient cell analyses, reveal that targeting the broader cellular pathogenesis associated with primary mitochondrial disease provides new therapeutic avenues for the treatment of this disorder.

Preferred agents for screening alone and in combination include the agents listed in Table II, SIRT Agonists, e.g., Nicotinic Acid or resveratrol, MTORCI inhibitors such as rapamycin and derivatives thereof, PPAR Agonists, such as Rosiglitazone or Fenofibrate, AMPK Agonists such as AICAR. Translation Inhibitors, such as cycloheximide, actinomycin and anisomycin, Autophagy Inhibitors, e.g., (lithium chloride or 3-methyladenine), hydralazine, Pyruvate dehydrogenase complex activators (e.g., Dichloroacetate (DCA). Nutrients such as glucose, and Antioxidants, including Vitamin E and N-acetylcysteine. Acipimox can also be employed.

In one aspect, existing libraries of compounds can be screening using the protocols described herein. Such libraries are commercially available and include, without limitation, Large Compound libraries, e.g., LOPAC 1280: Contains 1280 market drugs covering majority of targets as described on the world wide web at sigmaaldrich.com/life-science/cell biology/bioactive-small-molecules/lopaCI280-navigator.html; Pharmakon 1600: Collection of 1600 known drugs on world wide web at ms.discovery.com; Selleck chem bioactive compounds library: 2645 bioactive compounds covering inhibitors, Natural products, API and chemotherapeutic agents described on the web at selleckchem.com/screening/chemical-library.html; ChemBridge DIVERset: Contains 50000 compounds for primary screening described on the world wide web at chembridge.com/screening_libraries/diversity_libraries/diverset/; the NIH clinical collection: approx 450 drugs which have been in phase I-III clinical trials listed on the web at iccb.med.harvard.edu/application. Micorsource Discovery Spectrum Collection of 2560 FDA approved drugs and human biologics.

Natural Product Library: About 800 Natural Products described on the web at nccih.nih.gov/grants/natural products/libraries Small and targeted Libraries: Drugs/Molecules targeting specific pathways (PI3K/Akt/mTOR, Autophagy, Oxidation-Reduction Compound Library etc), contains approx 50-200 Drugs on average and provided by Enzo, Sigma etc.

Compositions and Methods for the Treatment of Mitochondrial and Respiratory Chain Disorders In one aspect, the invention provides a method for treating or protecting mitochondria with respiratory chain lesions, comprising administering to a subject in need of such treatment an effective amount of one or more combinatorial compositions of the invention. An exemplary composition comprises N-acetylcysteine, glucose and nicotinic acid in the following concentrations: Glucose: 5-11 mM, N-acetylcysteine 0.1-10 mM, and Nicotinic acid 0.1-10 mM and lithium chloride 0.1-10 mM. In certain embodiments, at least 5, at least 6, at least 8, at least 9 mM, at least 10 mM (or any integer in between) glucose is used. In certain embodiments, at least 0.2, at least 0.4, at least 1, at least 3, at least 5, at least 8 mM, at least 10 mM N-acetyl cysteine (or any integer in between) is used. On other embodiments, at least 0.2, at least 0.4, at least 1, at least 3, at least 5, at least 8 mM, at least 10 mM nicotinic acid (or any integer in between) is used. While nicotinic acid is exemplified herein, nicotinamide, nicotinamide riboside or Acipmox could also be used. The 3 components can be present in a 1:1:1 ratio, 1:2:1: ratio, 1:3:1, 1:2:2 and 1:3:3.

As discussed above, mitochondrial diseases present challenges to the development of therapeutic modalities. The inventors have developed a method of combinatorial compound screening and have identified several combinations of agents that address one or more deficits in models of Mitochondrial Complex I disease. Some of these agents act synergistically to correct defects in mitochondrial function. These and other aspects of the disclosure are set out in detail below.

A. Mitochondrial Structure and Function

The mitochondrion is a double-membrane-bound organelle found in most eukaryotic organisms. Some cells in some multicellular organisms may however lack them (for example, mature mammalian red blood cells). A number of unicellular organisms, such as microsporidia, parabasalids, and diplomonads, have also reduced or transformed their mitochondria into other structures. To date, only one eukaryote, Monocercomonoides, is known to have completely lost its mitochondria. Mitochondria generate most of the cell's supply of adenosine triphosphate (ATP), used as a source of chemical energy.

Mitochondria are commonly between 0.75 and 3 μm in diameter but vary considerably in size and structure. Unless specifically stained, they are not visible. In addition to supplying cellular energy, mitochondria are involved in other tasks, such as signaling, cellular differentiation, and cell death, as well as maintaining control of the cell cycle and cell growth. Mitochondrial biogenesis is in turn temporally coordinated with these cellular processes. Mitochondria have been implicated in several human diseases, including mitochondrial disorders, cardiac dysfunction, heart failure and autism.

The number of mitochondria in a cell can vary widely by organism, tissue, and cell type. For instance, red blood cells have no mitochondria, whereas liver cells can have more than 2000. Oocytes have approximately 250,000 mitochondria. The organelle is composed of compartments that carry out specialized functions. These compartments or regions include the outer membrane, the intermembrane space, the inner membrane, and the cristae and matrix.

Mitochondrial DNA (mtDNA or mDNA) is the DNA located in mitochondria, cellular organelles within eukaryotic cells that convert chemical energy from food into a form that cells can use, adenosine triphosphate (ATP). Mitochondrial DNA is only a small portion of the DNA in a eukaryotic cell; most of the DNA can be found in the cell nucleus and, in plants and algae, also in plastids such as chloroplasts.

Eukaryotic cells having mitochondria produce ATP from products of the citric acid cycle and perform fatty acid and amino acid oxidation. At the mitochondrial inner membrane, electrons from NADH and FADH2 pass through the electron transport chain to oxygen, which is reduced to water. The electron transport chain comprises an enzymatic series of electron donors and acceptors. Each electron donor will pass electrons to a more electronegative acceptor, which in turn donates these electrons to another acceptor, a process that continues down the series until electrons are passed to oxygen, the most electronegative and terminal electron acceptor in the chain. Passage of electrons between donor and acceptor releases energy, which is used to generate a proton gradient across the mitochondrial membrane by actively "pumping" protons into the intermembrane space, producing a thermodynamic state that has the potential to do work. The entire process is called oxidative phosphorylation, since ADP is phosphorylated to ATP using the energy of hydrogen oxidation in many steps.

A small percentage of electrons do not complete the whole series and instead directly leak to oxygen, resulting in the formation of the free-radical superoxide, a highly reactive molecule that contributes to oxidative stress and has been implicated in a number of diseases and aging.

Energy obtained through the transfer of electrons down the ETC is used to pump protons from the mitochondrial matrix into the intermembrane space, creating an electrochemical proton gradient (ΔpH) across the inner mitochondrial membrane (IMM). This proton gradient is largely but not exclusively responsible for the mitochondrial membrane potential ($\Delta\psi_M$). It allows ATP synthase to use the flow of $H^+$ through the enzyme back into the matrix to generate ATP from adenosine diphosphate (ADP) and inorganic phosphate. Complex I (NADH coenzyme Q reductase; labeled I) accepts electrons from the Krebs cycle electron carrier nicotinamide adenine dinucleotide (NADH), and passes them to coenzyme Q (ubiquinone; labeled Q), which also receives electrons from complex II (succinate dehydrogenase; labeled II). Q passes electrons to complex III (cytochrome bCI complex; labeled III), which passes them to cytochrome c (cyt c). Cyt c passes electrons to Complex IV (cytochrome c oxidase; labeled IV), which uses the electrons and hydrogen ions to reduce molecular oxygen to water.

Four membrane-bound complexes have been identified in mitochondria. Each is an extremely complex transmembrane structure that is embedded in the inner membrane. Three of them are proton pumps. The structures are electrically connected by lipid-soluble electron carriers and water-soluble electron carriers. The overall electron transport chain:

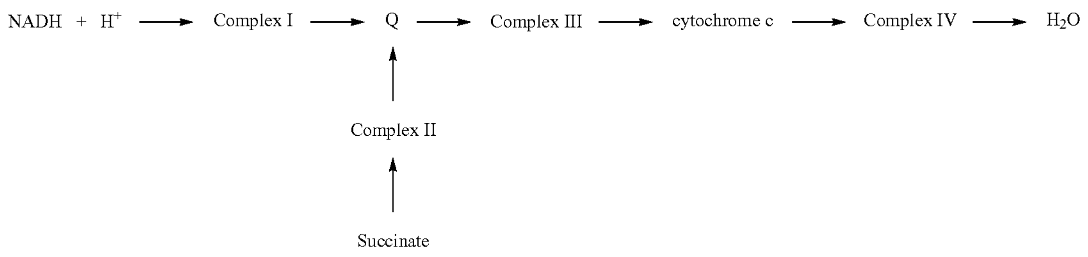

In Complex I (NADH:ubiquinone oxidoreductase, NADH-CoQ reductase, or NADH dehydrogenase), two electrons are removed from NADH and ultimately transferred to a lipid-soluble carrier, ubiquinone (UQ). The reduced product, ubiquinol ($UQH_2$), freely diffuses within the membrane, and Complex I translocates four protons ($H^+$) across the membrane, thus producing a proton gradient. Complex I is one of the main sites at which premature electron leakage to oxygen occurs, thus being one of the main sites of production of superoxide.

The pathway of electrons is as follows. NADH is oxidized to $NAD^+$, by reducing Flavin mononucleotide to $FMNH_2$ in one two-electron step. $FMNH_2$ is then oxidized in two one-electron steps, through a semiquinone intermediate. Each electron thus transfers from the $FMNH_2$ to an Fe—S cluster, from the Fe—S cluster to ubiquinone (Q). Transfer of the first electron results in the free-radical (semiquinone) form of Q, and transfer of the second electron reduces the semiquinone form to the ubiquinol form, $QH_2$. During this process, four protons are translocated from the mitochondrial matrix to the intermembrane space. As the electrons become continuously oxidized and reduced throughout the complex an electron current is produced along the 180 Angstrom width of the complex within the membrane. This current powers the active transport of four protons to the intermembrane space per two electrons from NADH.

The oxphos complexes are inhibited by many different toxins including but not limited to alkylguanides (e.g., Guanethidine), rotenone, barbiturates, chlorpromazine, piericidin, cyanide, azide, oligomycine, etc.

B. Mitochondrial Complex I Disease

Mitochondrial complex I deficiency is due to limited structure, assembly, or function (deficiency) of a very large protein complex called complex I. Complex I is found in cell structures called mitochondria, which convert the energy from food into a form that cells can use. Complex I is the first of five mitochondrial respiratory chain complexes that carry out a multi-step process called oxidative phosphorylation, through which cells derive much of their energy.

Mitochondrial complex I deficiency can cause a wide variety of signs and symptoms affecting many organs and systems of the body, particularly the nervous system, the heart, and the muscles used for movement (skeletal muscles). These signs and symptoms can appear at any time from birth to adulthood. Mitochondrial diseases are thought to occur in at least 1 in 4,300 people. Mitochondrial complex I deficiency is the most common cause of mitochondrial disease in children, accounting for approximately 30 percent of cases.

People with mitochondrial complex I deficiency typically have neurological problems, such as abnormal brain function (encephalopathy), recurrent seizures (epilepsy), intellectual disability, difficulty coordinating movements (ataxia), or involuntary movements (dystonia). Affected individuals may have low muscle tone (hypotonia), muscle pain (myalgia), and extreme fatigue in response to physical activity (exercise intolerance). They tend to develop elevated levels of lactic acid in the blood (lactic acidosis), which can cause nausea, vomiting, weakness, and rapid breathing. In severe cases, lactic acidosis can be life-threatening.

People with mitochondrial complex I deficiency sometimes have heart, liver, or kidney problems. Vision problems due to abnormal eye movement or breakdown (degeneration) of the nerves that carry signals from the eyes to the brain (optic nerves) can also occur. They may also have severe vision loss due to optic nerve or retinal diseases, including Leber's Hereditary Optic Neuropathy.

Some people with mitochondrial complex I deficiency have groups of signs and symptoms that are classified as a specific syndrome. For example, a condition called Leigh syndrome is most commonly caused by mitochondrial complex I deficiency. Leigh syndrome is characterized by progressive loss of mental and movement abilities (developmental or psychomotor regression) and typically results in death within 2 to 3 years from the onset of symptoms. Another condition that can be caused by mitochondrial complex I deficiency, Leber's hereditary optic neuropathy, is associated mainly with vision problems due to optic nerve degeneration. These syndromes can also have other causes. There are now nearly 100 different genes in which mutations have been found to cause Leigh syndrome.

Mutations in many genes can cause mitochondrial complex I deficiency. Most of these genes provide instructions for making components of complex I or proteins that help assemble the complex. In some cases, the genes are involved in other functions that influence these processes. Mutations that cause mitochondrial complex I deficiency impair the formation or function of complex I. As a result, complex I activity is reduced and oxidative phosphorylation is impaired. Researchers believe that problems with oxidative phosphorylation can lead to cell death by reducing the amount of energy available in the cell. It is thought that tissues and organs that require a lot of energy, such as the nervous system, heart, liver, kidneys, and skeletal muscles, are most affected by a reduction in oxidative phosphorylation. Other biochemical factors can also cause cell dysfunction and death in complex I deficiency, including increased oxidative stress and impaired cellular redox signaling involving reduced to oxidized ratios of nicotinamide adenine dinucleotide (NADH:NAD+).

Most genes known to be involved in mitochondrial complex I deficiency are found in nuclear DNA, which is packaged in chromosomes within the cell nucleus. Other genes involved in the condition are found in mitochondrial DNA (mtDNA), which is located in the mitochondria themselves. Most of the body's cells contain many mitochondria, and the mitochondria each contain many sets of mtDNA. When a mutation occurs in mtDNA, either all the mtDNA will have the same change (homoplasmy), or just some of the mtDNA will contain the change (heteroplasmy). A higher percentage of mutated mtDNA typically causes more severe disease. Mitochondrial complex I deficiency shows extreme genetic heterogeneity and can be caused by mutation in nuclear-encoded genes or in mitochondrial-encoded genes. There are no obvious genotype-phenotype correlations, and inference of the underlying basis from the clinical or biochemical presentation is difficult, if not impossible; however, the majority of cases are caused by mutations in nuclear-encoded genes.

In some individuals, the clinical picture is characteristic of a specific mitochondrial disorder (e.g., LHON, NARP, or maternally inherited LS), and the diagnosis can be confirmed by identification of a pathogenic mtDNA variant on molecular genetic testing of DNA extracted from a blood sample. In many individuals, such is not the case, and a more structured approach is needed, including family history, blood and/or CSF lactate concentration, neuroimaging, cardiac evaluation, and molecular genetic testing for a mtDNA or nuclear gene pathogenic variant. Approaches to molecular genetic testing of a proband to consider are serial testing of single genes, multi-gene panel testing (simultaneous testing of multiple genes), and/or genomic testing (e.g., sequencing of the entire mitochondrial genome, genome sequencing, or exome sequencing to identify a pathogenic variant in a nuclear gene). In many individuals in whom molecular genetic testing does not yield or confirm a diagnosis, further investigation of suspected mitochondrial disease can involve a range of different clinical tests, including muscle biopsy for respiratory chain function.

Mitochondrial disorders may be caused by defects of nuclear DNA or mtDNA. Nuclear gene defects may be inherited in an autosomal recessive or autosomal dominant manner. Mitochondrial DNA defects are transmitted by maternal inheritance. Mitochondrial DNA deletions generally occur de novo and thus cause disease in one family member only, with an approximate recurrence risk of 1 in 24. Mitochondrial DNA single-nucleotide variants and duplications may be transmitted down the maternal line. The father of a proband is not at risk of having the mtDNA pathogenic variant, but the mother of a proband (usually) has the mitochondrial pathogenic variant and may or may not have symptoms. A male does not transmit the mtDNA pathogenic variant to his offspring. A female harboring a heteroplasmic mtDNA single-nucleotide variant may transmit a variable amount of mutated mtDNA to her offspring, resulting in considerable clinical variability among sibs within the same family. Prenatal genetic testing and interpretation of test results for mtDNA disorders are difficult because of mtDNA heteroplasmy. De novo tissue-specific pathogenic nucleotide variants are rare, but associated with low recurrence risks.

The management of mitochondrial disease is largely supportive and may include early diagnosis and treatment of diabetes mellitus, cardiac pacing for conduction defects or arrhythmia, ptosis correction, intraocular lens replacement for cataracts, and cochlear implantation for sensorineural hearing loss. Individuals with complex I and/or complex II deficiency may benefit from oral administration of riboflavin; those with ubiquinone (coenzyme Q10) deficiency may benefit from oral coenzyme $Q_{10}$ therapy; arginine may prevent or modulate stroke in MELAS or Leigh syndrome; exercise may improve function in individuals with mitochondrial myopathy; and those with mitochondrial neurogastrointestinal encephalomyopathy (MNGIE) may benefit from hematopoietic stem cell transplantation.

II. Therapeutic Agents

As shown in the data included herein, the inventors have screened over 40 drugs for effects on lifespan of gas-1(fc21) *C. elegans* exhibiting NDUFS2 dysfunction (see FIGS. 1-2). They discovered 17 hits in three main categories: antioxidants, metabolic modifiers and signaling modifiers. Several combinations were randomly screened for effects on lifespan (efficacy, toxicity and synergy). Two combinations of drugs restored lifespan (glucose (Glu)+nicotinic acid (NA)+N-Acetylcysteine (NAC); resveratrol+Folinic acid+cysteamine). Dual combinations of NA+Glu, NA+NAC, and Glu+NAC also showed improved lifespan (see FIGS. 3-8 and Examples).

The following is a general discussion of the agents contemplated for use in treating mitochondrial disease.

A. Glucose (GLU)

Glucose (GLU) is a simple sugar with the molecular formula $C_6H_{12}O_6$. Glucose circulates in the blood of animals as blood sugar. It is made during photosynthesis from water and carbon dioxide, using energy from sunlight. It is the most important source of energy for cellular respiration. Glucose is stored as a polymer, in plants as starch and in animals as glycogen.

With six carbon atoms, it is classed as a hexose, a subcategory of the monosaccharides. D-Glucose is one of the sixteen aldohexose stereoisomers. The D-isomer, D-glucose, also known as dextrose, occurs widely in nature, but the L-isomer, L-glucose, does not. Glucose can be obtained by hydrolysis of carbohydrates such as milk sugar (lactose), cane sugar (sucrose), maltose, cellulose, glycogen, etc. It is commonly commercially manufactured from cornstarch by hydrolysis via pressurized steaming at controlled pH in a jet followed by further enzymatic depolymerization. Unbonded glucose is one of the main ingredients of honey.

Glucose is the most widely used aldohexose in most living organisms. One possible explanation for this is that glucose has a lower tendency than other aldohexoses to react nonspecifically with the amine groups of proteins. This reaction—glycation—impairs or destroys the function of many proteins. Glucose's low rate of glycation can be attributed to its having a more stable cyclic form compared to other aldohexoses, which means it spends less time than they do in its reactive open-chain form. The reason for glucose having the most stable cyclic form of all the aldohexoses is that its hydroxy groups (with the exception of the hydroxy group on the anomeric carbon of D-glucose) are in the equatorial position. Many of the long-term complications of diabetes (e.g., blindness, kidney failure, and peripheral neuropathy) are probably due to the glycation of proteins or lipids. In contrast, enzyme-regulated addition of sugars to protein is called glycosylation and is essential for the function of many proteins.

Glucose is a monosaccharide with formula $C_6H_{12}O_6$ or $H—(C{=}O)—(CHOH)_5—H$, whose five hydroxyl (OH) groups are arranged in a specific way along its six-carbon back.

In its fleeting open-chain form, the glucose molecule has an open (as opposed to cyclic) and unbranched backbone of six carbon atoms, C-1 through C-6; where C-1 is part of an aldehyde group $H(C{=}O)—$, and each of the other five carbons bears one hydroxyl group —OH. The remaining bonds of the backbone carbons are satisfied by hydrogen atoms —H. Therefore, glucose is both a hexose and an aldose, or an aldohexose. The aldehyde group makes glucose a reducing sugar giving a positive reaction with the Fehling test.

Each of the four carbons C-2 through C-5 is a stereocenter, meaning that its four bonds connect to four different substituents. (Carbon C-2, for example, connects to —(C═O)H, —OH, —H, and $—(CHOH)_4H$.) In D-glucose, these four parts must be in a specific three-dimensional arrangement. Namely, when the molecule is drawn in the Fischer projection, the hydroxyls on C-2, C-4, and C-5 must be on the right side, while that on C-3 must be on the left side.

The positions of those four hydroxyls are exactly reversed in the Fischer diagram of L-glucose. D- and L-glucose are two of the 16 possible aldohexoses; the other 14 are allose, altrose, galactose, gulose, idose, mannose, and talose, each with two enantiomers, "D-" and "L-".

It is important to note that the linear form of glucose makes up less than 3% of the glucose molecules in a water solution. The rest is one of two cyclic forms of glucose that are formed when the hydroxyl group on carbon 5 (C5) bonds to the aldehyde carbon 1 (CI).

In solutions, the open-chain form of glucose (either "D-" or "L-") exists in equilibrium with several cyclic isomers, each containing a ring of carbons closed by one oxygen atom. In aqueous solution however, more than 99% of glucose molecules, at any given time, exist as pyranose forms. The open-chain form is limited to about 0.25% and furanose forms exists in negligible amounts. The terms "glucose" and "D-glucose" are generally used for these cyclic forms as well. The ring arises from the open-chain form by an intramolecular nucleophilic addition reaction between the aldehyde group (at C-1) and either the C-4 or C-5 hydroxyl group, forming a hemiacetal linkage, —C(OH)H—O—.

The reaction between C-1 and C-5 yields a six-membered heterocyclic system called a pyranose, which is a monosaccharide sugar (hence "-ose") containing a derivatised pyran skeleton. The (much rarer) reaction between C-1 and C-4 yields a five-membered furanose ring, named after the cyclic ether furan. In either case, each carbon in the ring has one hydrogen and one hydroxyl attached, except for the last carbon (C-4 or C-5) where the hydroxyl is replaced by the remainder of the open molecule (which is $—(C(CH_2OH)HOH)—H$ or —(CHOH)—H, respectively). The ring-closing reaction makes carbon C-1 chiral, too, since its four bonds lead to —H, to —OH, to carbon C-2, and to the ring oxygen. These four parts of the molecule may be arranged around C-1 (the anomeric carbon) in two distinct ways, designated by the prefixes "α-" and "β-". When a glucopyranose molecule is drawn in the Haworth projection, the designation "α-" means that the hydroxyl group attached to C-1 and the $—CH_2OH$ group at C-5 lies on opposite sides of the ring's plane (a trans arrangement), while "β-" means that they are on the same side of the plane (a cis arrangement). Therefore, the open-chain isomer D-glucose gives rise to four distinct cyclic isomers: α-D-glucopyranose, β-D-glucopyranose, α-D-glucofuranose, and β-D-glucofuranose. These five structures exist in equilibrium and interconvert, and the interconversion is much more rapid with acid catalysis.

The other open-chain isomer L-glucose similarly gives rise to four distinct cyclic forms of L-glucose, each the mirror image of the corresponding D-glucose.

The rings are not planar, but are twisted in three dimensions. The glucopyranose ring (α or β) can assume several non-planar shapes, analogous to the "chair" and "boat" conformations of cyclohexane. Similarly, the glucofuranose ring may assume several shapes, analogous to the "envelope" conformations of cyclopentane.

In the solid state, only the glucopyranose forms are observed, forming colorless crystalline solids that are highly soluble in water and acetic acid but poorly soluble in methanol and ethanol. They melt at 146° C. (295° F.) (α) and 150° C. (302° F.) (β), and decompose at higher temperatures into carbon and water.

Each glucose isomer is subject to rotational isomerism. Within the cyclic form of glucose, rotation may occur around the O6-C6-C5-O5 torsion angle, termed the ω-angle, to form three staggered rotamer conformations called gauche-gauche (gg), gauche-trans (gt) and trans-gauche (tg). There is a tendency for the ω-angle to adopt a gauche conformation, a tendency that is attributed to the gauche effect.

All forms of glucose are colorless and easily soluble in water, acetic acid, and several other solvents. They are only sparingly soluble in methanol and ethanol.

The open-chain form is thermodynamically unstable, and it spontaneously isomerizes to the cyclic forms. (Although the ring closure reaction could in theory create four- or three-atom rings, these would be highly strained, and are not observed in practice.) In solutions at room temperature, the four cyclic isomers interconvert over a time scale of hours, in a process called mutarotation. Starting from any proportions, the mixture converges to a stable ratio of α:β 36:64. The ratio would be α:β 11:89 if it were not for the influence of the anomeric effect. Mutarotation is considerably slower at temperatures close to 0° C. (32° F.).

Mutarotation consists of a temporary reversal of the ring-forming reaction, resulting in the open-chain form, followed by a reforming of the ring. The ring closure step may use a different —OH group than the one recreated by the opening step (thus switching between pyranose and furanose forms), or the new hemiacetal group created on C-1 may have the same or opposite handedness as the original one (thus switching between α and β forms). Thus, though the open-chain form is barely detectable in solution, it is an essential component of the equilibrium.

Depending on conditions, three major solid forms of glucose can be crystallised from water solutions: α-glucopyranose. β-glucopyranose, and β-glucopyranose hydrate.

The value of glucose at physiologic levels in primary mitochondrial respiratory chain relates to the ability to generate cellular energy (adenosine triphosphate, ATP) through the anaerobic process of glycolysis. Glycolysis is much less efficient at generating ATP than mitochondrial oxidative phosphorylation. However, individuals with primary mitochondrial respiratory chain disease who have impaired ability to generate ATP efficiently from mitochondrial oxidative phosphorylation often have cellular upregulation of their glycolytic capacity as an adaptive response—therefore, the finding that glucose is therapeutic in mitochondrial oxidative phosphorylation disease represents not just the glucose molecule itself, but the value of providing nutritional equivalents that can be effectively used to improved energy production in the setting of primary mitochondrial respiratory chain disease.

B. N-Acetylcysteine (NAC)

Acetylcysteine, also known as N-acetylcysteine (NAC), is a medication that is used to treat paracetamol (acetaminophen) overdose, and to loosen thick mucus in individuals with cystic fibrosis or chronic obstructive pulmonary disease. It can be taken intravenously, by mouth, or inhaled as a mist. Some people use it as a dietary supplement.

Common side effects include nausea and vomiting when taken by mouth. The skin may occasionally become red and itchy with either form. A non-immune type of anaphylaxis may also occur. It appears to be safe in pregnancy. For paracetamol overdose, it works by increasing the level of glutathione, an antioxidant that can neutralize the toxic breakdown products of paracetamol. When inhaled, it acts as a mucolytic by decreasing the thickness of mucus.

Acetylcysteine was initially patented in 1960 and licensed for use in 1968. It is on the World Health Organization's List of Essential Medicines, the most effective and safe medicines needed in a health system. It is available as a generic medication and is inexpensive.

Acetylcysteine serves as a prodrug to L-cysteine. L-cysteine is a precursor to the biologic antioxidant glutathione. Hence, administration of acetylcysteine replenishes glutathione stores.

Glutathione, along with oxidized glutathione (GSSG) and S-nitrosoglutathione (GSNO), have been found to bind to the glutamate recognition site of the NMDA and AMPA receptors (via their γ-glutamyl moieties), and may be endogenous neuromodulators. At millimolar concentrations, they may also modulate the redox state of the NMDA receptor complex. In addition, glutathione has been found to bind to and activate ionotropic receptors that are different from any other excitatory amino acid receptor, and which may constitute glutathione receptors, potentially making it a neurotransmitter. As such, since N-acetylcysteine is a prodrug of glutathione, it may modulate all of the aforementioned receptors as well. Glutathione also modulates the NMDA receptor by acting at the redox site.

L-cysteine also serves as a precursor to cystine which in turn serves as a substrate for the cystine-glutamate antiporter on astrocytes hence increasing glutamate release into the extracellular space. This glutamate in turn acts on $mGluR_{2/3}$ receptors, and at higher doses of acetylcysteine, $mGluR_5$.

Acetylcysteine also possesses some anti-inflammatory effects possibly via inhibiting NF-κB and modulating cytokine synthesis. It is extensively liver metabolized, CYP450 minimal, urine excretion is 22-30% with a half-life of 5.6 hours in adults and 11 hours in neonates. Acetylcysteine is the N-acetyl derivative of the amino acid L-cysteine, and is a precursor in the formation of the antioxidant glutathione in the body. The thiol (sulfhydryl) group confers antioxidant effects and is able to reduce free radicals.

N-acetyl-L-cysteine is soluble in water and alcohol, and practically insoluble in chloroform and ether. It is a white to white with light yellow cast powder, and has a pKa of 9.5 at 30° C. Acetylcysteine is available in different dosage forms for different indications:

- solution for inhalation (Assist, Mucomyst, Mucosil)—inhaled for mucolytic therapy or ingested for nephroprotective effect (kidney protection)
- intravenous injection (Assist, Parvolex, Acetadote)—treatment of paracetamol/acetaminophen overdose
- oral solution—various indications.
- effervescent tablets
- ocular solution—for mucolytic therapy
- tablets—sometimes in a sustained release formula sold as a nutritional supplement capsules The IV injection and inhalation preparations are, in general, prescription only, whereas the oral solution and the effervescent tablets are available over the counter in many countries. Acetylcysteine is available as a health supplement in the United States, typically in capsule form. The utility of N-acetylcysteine in primary mitochondrial disease is to rebalance oxidative stress, which occurs throughout the body and central nervous system. As oxidant production is increased and oxidative stress responses are depleted in primary mitochondrial disease, the value of N-aceytlcysteine is to improve cellular resiliency at the level of boosting oxidative stress responses, thereby improving cellular healthy and reducing cellular decompensation upon stressors that leads to multi-system disease and/or death.

Nicotinic Acid (NA)

Nicotinic acid (NA), also known as niacin, is an organic compound and a form of vitamin B3, an essential human nutrient. It has the formula $C_6H_5NO_2$ and belongs to the group of the pyridinecarboxylic acid.

NA is obtained in the diet from a variety of whole and processed foods, with highest contents in fortified packaged foods, tuna, some vegetable and other animal sources. Some countries require its addition to grains. Medication and supplemental NA are primarily used to treat high blood cholesterol and pellagra (niacin deficiency). Insufficient NA in the diet can cause nausea, skin and mouth lesions, anemia, headaches, and tiredness. The lack of niacin may also be observed in pandemic deficiency diseases, which are caused by a lack of five crucial vitamins (NA, vitamin C, thiamin, vitamin D, and vitamin A) and are usually found in areas of widespread poverty and malnutrition.

This colorless, water-soluble solid is a derivative of pyridine, with a carboxyl group (COOH) at the 3-position. Other forms of vitamin B3 include the corresponding amide nicotinamide (niacinamide), where the carboxyl group has been replaced by a carboxamide group ($CONH_2$), as well as more complex amides and a variety of esters.

NA and nicotinamide are both precursors of the coenzymes nicotinamide adenine dinucleotide (NAD) and nicotinamide adenine dinucleotide phosphate (NADP) in vivo. NAD converts to NADP by phosphorylation in the presence of the enzyme NAD+ kinase. NADP and NAD are coenzymes for many dehydrogenases, participating in many hydrogen transfer processes. NAD is important in catabolismof fat, carbohydrate, protein, and alcohol, as well as cell signaling and DNA repair, and NADP mostly in anabolism reactions such as fatty acid and cholesterol synthesis. High energy requirements (brain) or high turnover rate (gut, skin) organs are usually the most susceptible to their deficiency.

NA supplementation has not been found useful for decreasing the risk of cardiovascular disease in those already on a statin, but appears to be effective in those not taking a statin. Although NA and nicotinamide are identical in their vitamin activity, nicotinamide does not have the same pharmacological effects (lipid-modifying effects) as NA. Nicotinamide does not reduce cholesterol or cause flushing. As the precursor for NAD and NADP, NA is also involved in DNA repair.

NA is available as a prescription product, and in the United States as a dietary supplement. Prescription products can be immediate release (Niacor, 500 mg tablets) or extended release (Niaspan, 500 and 1000 mg tablets). Dietary supplement products can be immediate or slow release, the latter including inositol hexanicotinate.

Over-the-counter NA is not federally regulated in the United States. Some "no flush" types, such as inositol hexanicotinate contain convertible niacin compounds, but have little clinical efficacy in reducing cholesterol levels.

Nicotinamide may be obtained from the diet where it is present primarily as NAD+ and NADP+. These are hydrolyzed in the intestine and the resulting nicotinamide is absorbed either as such, or following its hydrolysis to nicotinic acid. Nicotinamide is present in nature in only small amounts, however it is the main form of vitamin B3 in plasma. In unprepared foods, niacin is present mainly in the form of the cellular pyridine nucleotides NAD and NADP. Enzymatic hydrolysis of the co-enzymes can occur during the course of food preparation. Boiling releases most of the total NA present in sweet corn as nicotinamide (up to 55 mg/kg). Nicotinamide may be toxic to the liver at doses exceeding 3 g/day for adults.

A prescription extended release NA, Niaspan, has a film coating that delays release of the niacin, resulting in an absorption over a period of 8-12 hours. The extended release formulations generally reduce vasodilation and flushing side effects, but increase the risk of hepatotoxicity compared to the immediate release forms.

One form of dietary supplement is inositol hexanicotinate (IHN), which is inositol that has been esterified with NA on all six of inositol's alcohol groups. IHN is usually sold as "flush-free" or "no-flush" NA in units of 250, 500, or 1000 mg/tablets or capsules. It is sold as an over-the-counter formulation, and often is marketed and labeled as NA, thus misleading consumers into thinking they are getting the active form of the medication.

The value of NA in primary mitochondrial disease, particularly those involving impaired function of complex I (a.k.k the NADH Dehydrogenase enzyme) is to improve levels of nicotinamide adenine dinucleotide, and the ratios of its reduced (NADH) to oxidized (NAD+) redox forms, which regulate hundreds of other cellular reactions throughout the mitochondria and cell. These levels become deficient in mitochondrial disease, and the NADH:NAD+ ratio becomes altered, negatively impacting global mitochondrial and cellular metabolism and function. Providing precursor forms of NADH and NAD+ in the formulation of NA (and related formulations including by not limited to nicotinamide, nicotinamide riboside, long-acting nicotinic acid, etc) improves the cellular redox balance that is a hallmark of the secondary pathology that causes multi-organ symptoms in primary mitochondrial disease.

Other preferred combinations for use in the invention include glucose and cycloheximide.

Compounds of the invention, such as those provided in the tables herein are useful, for example, for treating or suppressing diseases associated with decreased mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in a subject by administering an effective amount of a compound as described above.

In addition, the compounds of the invention can be used for prophylaxis of redox stress and enhancement of cellular function.

In one aspect, the disclosure provides a method for treating or protecting mitochondria with respiratory chain lesions, comprising administering to a subject in need of such treatment an effective amount of one or more compounds of the invention.

Pharmaceutical Formulations

Where clinical applications are contemplated, pharmaceutical compositions will be prepared in a form appropriate for the intended application. Generally, this will entail preparing compositions (e.g., expression vector) that are essentially free of pyrogens, as well as other impurities that could be harmful to humans or animals.

One will generally desire to employ appropriate salts and buffers to render drugs stable and allow for uptake by target cells. Aqueous compositions of the present disclosure comprise an effective amount of the drug dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal, as well as through nasal feeding tubes or gastrostomy or jejunual ports and tubes that are commonly needed in primary mitochondrial disease patients. Alternatively, administration may be by intradermal, subcutaneous, intramuscular, intraperitoneal or intravenous injection. Such compositions would normally be administered as pharmaceutically acceptable compositions. as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that casy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion. (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

IV. Therapies

In another embodiment, combinatorial treatment of mitochondrial disease is contemplated. Combinations may be achieved by treating patients with a single composition or pharmacological formulation that includes two or more agents, or by treating the patient with distinct compositions or formulations, at the same time, wherein each composition includes a distinct agent. Alternatively, the various agents may be given in a staggered fashion ranging from minutes, to hours, to weeks. In such embodiments, one would generally ensure that the period of time between the each delivery was such that the agents would still be able to exert an advantageously combined effect on the cell or subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

By way of illustration, where Glucose is "A" NA is "B," and NAC is "C." the following permutations are exemplary:

A/B/C B/A/C A/C/B B/C/A C/A/B C/B/A

Other combinations wherein multiple administrations of one or more agents are likewise contemplated. Furthermore, multiple administrations of the cocktail itself are contemplated, such as in an ongoing or chronic basis. The administrations may be twice daily, daily, twice weekly, weekly, every other week, or monthly. They may also be administered for therapeutic purposes to mitochondrial disease patients who are acutely decompensating on a continual or more frequent basis in an acute medical setting (emergency department, intensive care unit, etc).

In another aspect, the present disclosure provides compositions comprising one or more of compounds as described above and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound (s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically. The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound (s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pre-gelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophoreυ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an IC50 of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

Kits and Articles of Manufacture

Any of the aforementioned products can be incorporated into a kit which may contain reagents and materials necessary for assessing GSH levels. Kits of the invention can contain the mutated *C. elegans* strains disclosed herein and/or genetically altered zebra fish. Kits can also comprise the necessary housing components for such animals along with requisite food stuffs for maintenance of the same. The kit can comprise an antisense or siRNA oligonucleotide of DNA or RNA, a polypeptide, a peptide, an antibody, a label, said label being detectable and optionally, operably linked to an oligonucleotide, polypeptide or antibody marker, or reporter, reagents for performing HPLC-ECD, a pharmaceutically acceptable carrier, a physiologically acceptable carrier, instructions for use, a container, a vessel for administration, an assay substrate, or any combination thereof.

The following materials and methods are provided to facilitate the practice of the present invention.

*C. elegans*

Strains and Maintenance—*C. elegans* N2 Bristol strain used in this study was obtained from the Caenorhabditis Genetics Center (CGC). Animals were maintained at 20° C. on Nematode Growth Media (NGM) plates spread with *Escherichia coli* OP50.

RNAi feeding—DLD-1 RNAi clone (LLC1.3) was obtained from the Ahringer RNAi collection and was sequence confirmed prior to use. The vector L4440 was utilized as a control.

Brood size analysis—Worms were synchronized by picking ten to fifteen N2 gravid adult worms onto NGM plates containing 0.2 mM IPTG, ampicillin and tetracycline spread with DLD-1 (LLCI.3) or L4440 bacteria and allowed to lay eggs for 2-2.5 hours. A single L4 larvae from the egg lay was placed on a 4 mm dish containing NGM and corresponding RNAi clone and allowed to lay eggs for 24 hours before being transferred to a fresh 4 mm NGM plate. Worms were transferred to fresh plates for 5 days and progeny were counted from each plate.

Western blot analysis—Approximately 500 young adult worms were briefly washed with S. basal media before resuspension in 250 uL of RIPA buffer (50 mM Tris HCl, pH 8.0, 150 mM NaCl, 1.0% NP-40, 0.5% sodium deoxycholate, 1.0 mM EDTA, 0.1% SDS) containing a 1/100 dilution of Protease inhibitor cocktail (Sigma). Worms were lysed using a mechanical hand homogenizer and pestle on ice and the resulting lysate was maintained at constant agitation for 30 minutes at 4° C. Lysate was subsequently centrifuged for 20 minutes at 16,000 rpm and the supernatant was removed. Protein concentration was determined using the Pierce BCA protein assay kit. 30 ug of whole cell lysate was utilized and blots were probed with anti-LAD monoclonal antibody at a 1:7500 dilution (abcam) to detect the DLD-1 protein. As a loading control blots were additionally probed with anti-Beta tubulin (source) at a 1: dilution.

Chemotaxis Assay—Chemotaxis analysis was performed as has been previously described (Haroon, S. J. of Cell Reports (2018); pmid:29562168). In brief, approximately 30 worms were collected and washed with *S. basal* media. Worms were placed 5 cm away from a spot containing 2 uL of 10% isoamyl alcohol dissolved in 100% ethanol and 1 uL of 10% sodium azide. After one hour distance traveled by each worm was marked and analyzed via image J.

Length Analysis—A synchronized population of worms grown on L4440 and LLCI.3 RNAi clones were monitored from the L4 stage of development till day 5 of adulthood. On the day of length analysis 4 mg/mL Quantification of Hsp6::GFP induction—A synchronized egg lay using 15-20 Hsp6::GFP gravid young adult worms on L4440 or LLCI.3 RNAi clones was performed to induce depletion of DLD-1 protein. Day 1 young adult worms were washed once in 4-5 mL of *S. basal* in a 50 mL conical tube and pelleted by centrifugation at 1300×g for 1 minute. Spent *S. basal* was removed and worms were resuspended in a final volume of 10 mL in preparation for biosorter analysis. An excitation wavelength of 488 nm and emission filter of 510 nm was utilized to measure induction of Hsp6::GFP induction in individual worms. Experiments were conducted with approximately 300 worms per sample with three biological replicates for each condition tested.

The following examples are provided to illustrate certain embodiments of the invention. They are not intended to limit the invention in any way.

EXAMPLE I

Dichloroacetate Treatment Improves Survival, Health, and Mitochondrial Morphology in FBXL4 Disease Human Fibroblasts and *C. elegans* Models FBXL4-related encephalomyopathic mitochondrial DNA depletion syndrome is a severe, multi-systemic mitochondrial disease caused by 47 pathogenic mutations reported to date. While FBXL4 function is not well understood, recessive mutations in FBXL4 lead to mitochondrial depletion and multiple respiratory chain complex deficiencies with pronounced lactic acidemia. In the present example, the physiologic effects of FBXL4 genetic mutations in *C. elegans* and human fibroblasts are described, along with stressor screens used to identify effective treatment strategies. The present examples provide data relating to several specific mitochondrial genes. The methods described herein could be employed using any of the over 1500 genes present in mitochondria which are listed on the world wide web at meseqdr.org/Mb.php?url+index.php.

The following materials and methods are provided to facilitate the practice of Example I.

Mitochondrial oxidant burden (MitoSOX Red), membrane potential (tetramethyl-rhodamine ethyl ester, TMRE), and mitochondrial content (MitoTracker Green FM, MTG) were performed in *C. elegans* at 20° C. using in vivo terminal pharyngeal bulb relative fluorescence microscopic quantitation. Briefly, synchronous populations of Day 0 young adults were moved to 35 mm NGM plates spread with OP50 *E. coli*, a desired drug treatment 2.5 mM N-acetylcysteine, Nicotinic acid, glucose and the duplicate or triplicates combination of these drugs or buffer control (S-basal/water for all other drugs) was performed on NGM plates. Simultaneously with the drug treatments, worms were treated with either 10 μM MitoSOX Red (matrix oxidant burden), 100 nM TMRE (mitochondrial membrane potential), or 2 μM MitoTracker Green FM (mitochondria content) for 24 h. The next day, worms were transferred with a pick onto 35 mm agar plates spread with OP50 *E. coli* without dye for 1 h to allow clearing of residual dye from the gut. Worms were then paralyzed in situ with 5 mg/ml levamisole. Photographs were taken in a darkened room at 160× magnification with a Cool Snap cf2 camera (Nikon, Melville, NY). A CY3 fluorescence cube set (MZFLIII, Leica, Bannockburn, IL) was used for MitoSOX and TMRE. A GFP2 filter set (Leica) was used for MitoTracker Green FM. Respective exposure times were 2 s, 320 ms, and 300 ms for each of MitoSOX, TMRE, and MitoTracker Green FM. The resulting images were background subtracted, and the nematode terminal pharyngeal bulb was manually circled to obtain mean intensity of the region by using Fiji Is Just ImageJ. Fluorescence data for each strain were normalized to its same day control to account for day-to-day variation. A minimum of 3 independent experiments of approximately 50 animals per replicate were studied per strain per dye. The significance of the difference in the mean fluorescence intensity between strains under different experimental conditions was assessed by mixed-effect ANOVA, which analyzes potential batch effect due to samples being experimentally prepared, processed, and analyzed on different days by including a batch random effect in the model. A statistical significance threshold was set at $P<0.05$. All statistical analyses were performed in SAS 9.3.

Animal brood size, egg hatching rate, larval development, body length, neuromuscular activity, and lifespan were quantified in the fbxl-1 (ok3741) *C. elegans* strain homolog of human FBXL4 (89.1% homology), which harbors a homozygous fbx1-1 700 basepair deletion. A semi-automated screening method (Mathew et al, 2016) was used to test drug treatment effects on an integrated *C. elegans* health endpoint of fecundity, brood size, and behavior. Human fibroblasts were studied from a subject harboring a 1067del (p.Gly356Alafs*15) nonsense mutation in the maternal FBXL4 allele and a c. 1790A>C (p.GLn597Pro) missense mutation in the paternal FBXL4 allele (Gai et al, 2013). Fibroblasts were cultured in DMEM (1 g/L glucose, 0.8 g/L L-Glutamine, 110 mg/L Sodium Pyruvate). Light, fluorescence, confocal microscopy and transmission electron microscopy (TEM, Lavorato et al, 2017) methods were used to analyze proband fibroblasts and mitochondrial morphology at baseline and following metabolic stress induced by incubating cells for 48 hours in glucose/uridine-free media. Mitotracker green was used for fluorescence microscopy. Tom20 Antibody (Santa Cruz) and DAPI was used for confocal microscopy.

Results

*C. elegans*. FBXL4 (vc3038) knockout worms at 20° C. had significantly reduced survival (87% and 73% of wild-type N2 Bristol median and maximal lifespan, respectively, $p<0.0001$) and brood size (17% of controls, $p<0.0001$). Their neuromuscular function was impaired, with significantly reduced motility (17% body bends/min relative to N2, $p<0.001$). Treating FBXL4 mutant young adult worms with 25 mM dichloroacetate (DCA), a pyruvate dehydrogenase kinase inhibitor that activates the pyruvate dehydrogenase complex, significantly improved brood size by day 3 (from 15% to 85%, $p<0.0001$)). See FIGS. 1-5.

Human fibroblasts. FBXL4 proband fibroblasts' morphology and ultrastructure were comparable at baseline to healthy controls except for increased lysosomes on TEM. When subjected to metabolic stressors (such as nutrient-depleted media) for 48 hrs, however, these cells developed very abnormal mitochondrial morphology and ultrastructure, including increased mitochondrial fragmentation on mitotracker green analysis and substantially increased lysosome content with damaged mitochondria ultrastructure on TEM analysis. Treating FBXL4 proband fibroblasts with 20 mM DCA during exposure to the metabolic stressor rescued their cell morphology and mitochondrial structure. See FIGS. 6-9. These fibroblast assays can be performed in 96 well plates employing different mitochondrial disease patient cell lines with previously identified genetic mutations. See FIG. 6B. In these assays, different stressors (e.g., chloramphenicol, RC complex inhibitors, oxidant stressors (e.g., hydrogen peroxide, diethylmaleate) or nutrient deprivation are tested and those that reduce cell viability by 50-80% are identified. Fibroblasts are then incubated in the presence of the identified stressor and then contacted with the therapeutic compounds of interest. Cellular parameters are then evaluated to identify efficacious therapeutic compound formulations which exert tolerable, protective and or therapeutic effects against mitochondrial disease phenotypes.

The effect of Sodium Dichloroacetate (DCA) on the morphology and behavior of fbxl4 zebrafish larvae carrying a homozygous point mutation (fbxl4$^{sul2470}$) was also studied. Mitochondrial disease often causes functional rather than structural problems, particularly under stress. Thus, fbxl4$^{sal2470}$ zebrafish larvae were exposed to chloramphenicol, a mitochondrial translation inhibitor, to stress larvae to elicit a disease phenotype at the level of morphology and behavior, and co-treated with 5 mM DCA was to investigate its therapeutic potential in this model. WT and homozygous fbxl4$^{sal2470}$ zebrafish larvae were exposed to 2.5 mM chloramphenicol (stressor) or 2.5 mM chloramphenicol plus 5 mM DCA (stressor and treatment) from 2 dpf to 7 dpf, with analysis of morphology and the neuromuscular function by touch and tap response assays. 7 dpf homozygous fbxl4$^{sal2470}$ zebrafish larvae exposed to chloramphenicol alone showed increased frequency of grey brain phenotype indicative of brain damage, marginally reduced survival, and decreased touch and tap response compared to WT larvae. Co-treatment of fbxl4$^{sa12470}$ mutants with chloramphenicol and 5 mM DCA showed a trend toward decreased grey brain frequency and increased tap and touch response at 7 dpf. FIGS. 10A-10E show the results obtained in a zebrafish model of fbxl4 with DCA in a thrashing assay.

Conclusion

FBXL4 knockout *C. elegans* have significantly reduced survival, fecundity, development, and neuromuscular function. Remarkably, 25 mM DCA significantly rescued their fecundity, with study ongoing of additional treatment effects. FBXL4 disease fibroblasts similarly showed reduced survival and abnormal mitochondrial morphology in metabolic stressors, with increased lysosome number suggestive of increased autophagic-lysosomal activity, severe phenotypes that were rescued with 20 mM DCA treatment. Moreover, results in a zebrafish model also showed improvement. These results are suggestive that DCA is a therapeutic candidate for FBXL4 disease that should be evaluated in robust clinical trials, and further highlight the utility of simple cell and animal model systems to identify therapeutic leads for complex mitochondrial diseases.

EXAMPLE II

Methods Employing NUBPL Disease Models in *C. elegans* and Zebrafish for the Identification of Therapeutic Agents for the Treatment of Mitochondrial Disorders Complex I dysfunction is the most common biochemical defect in mitochondrial disorders, particularly in children. The impact of these primary mitochondrial disorders on neurodevelopment and survival is related to critical alterations in cellular metabolism, energy homeostasis, and reactive oxygen species production. As mentioned previously, there is currently no cure or FDA-approved therapy for any mitochondrial disease, since little is known about downstream biochemical and physiologic abnormalities that contribute to their diverse clinical manifestations. Existing therapies are nonspecific, symptom management-based, and non-curative. NUBPL, encodes an Fe/S protein cluster involved in complex I assembly. Despite the importance of NUBPL the precise function of this protein cluster is currently unknown.

Complex I genes and NUBPL have clearly co-evolved and function of NUBPL is required for full activity of complex I. It has been previously shown that NUBPL can bind to iron sulfur clusters and that clusters are readily transferred to an iron-sulfur protein acceptor and facilitates assembly of Fe—S cofactors and subunits of complex I. Deletion of Ind1 (NUBPL) in yeast results in slow growth and decrease in complex I activity and assembly by ~80% [3].

A phylogenetic comparison of the NUBPL. Protein Sequences for NUBPL in *D. rerio, C. elegans, H. sapiens* and *Y. lipolytica* was performed using BlastP and aligned by ClustalW. The key conserved CxxC motif was identified. Data was generated using Geneious version 8.1.7 NUBPL function is dependent on the cysteine residues of the evolutionary conserved CxxC motif.

We obtained a genetic knockout NUBPL (34.7% homology) worm strain TM3754 from the National BioResource Project, which has a 478 base pair deletion. The strain is currently heterozygous for the deletion and displays the phenotypes of slow growth and reduced brood size. The mutation in this strain is currently not balanced, so to balance it and obtain a homozygous mutant strain we have outcrossed it with FX30168 tm18[dpy-5(tmIs1236)]) [5].

Figure 11A:
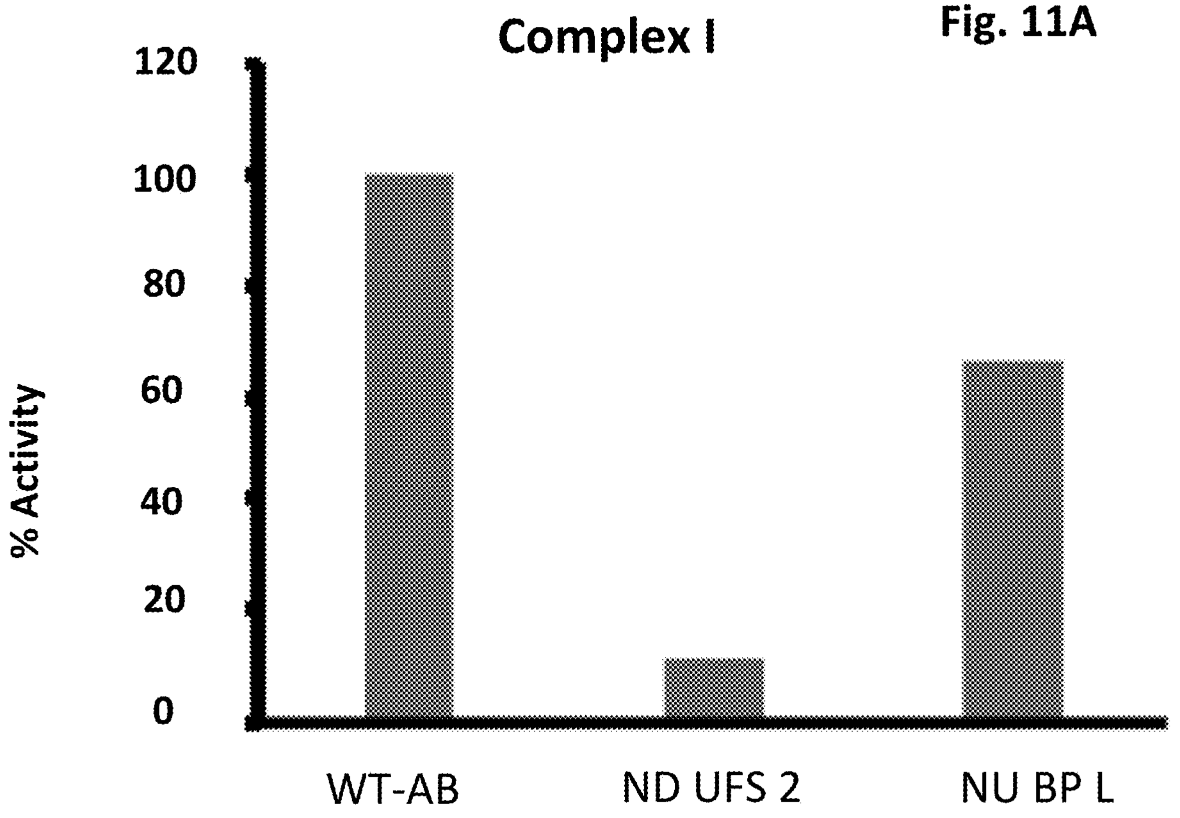
FIGS. 11A-11D. Zebra Fish ETC Activity An electron transport chain activity assay. The ETC activity of CI, C2 and C3 of AB (wild-type.
Figure 11B:
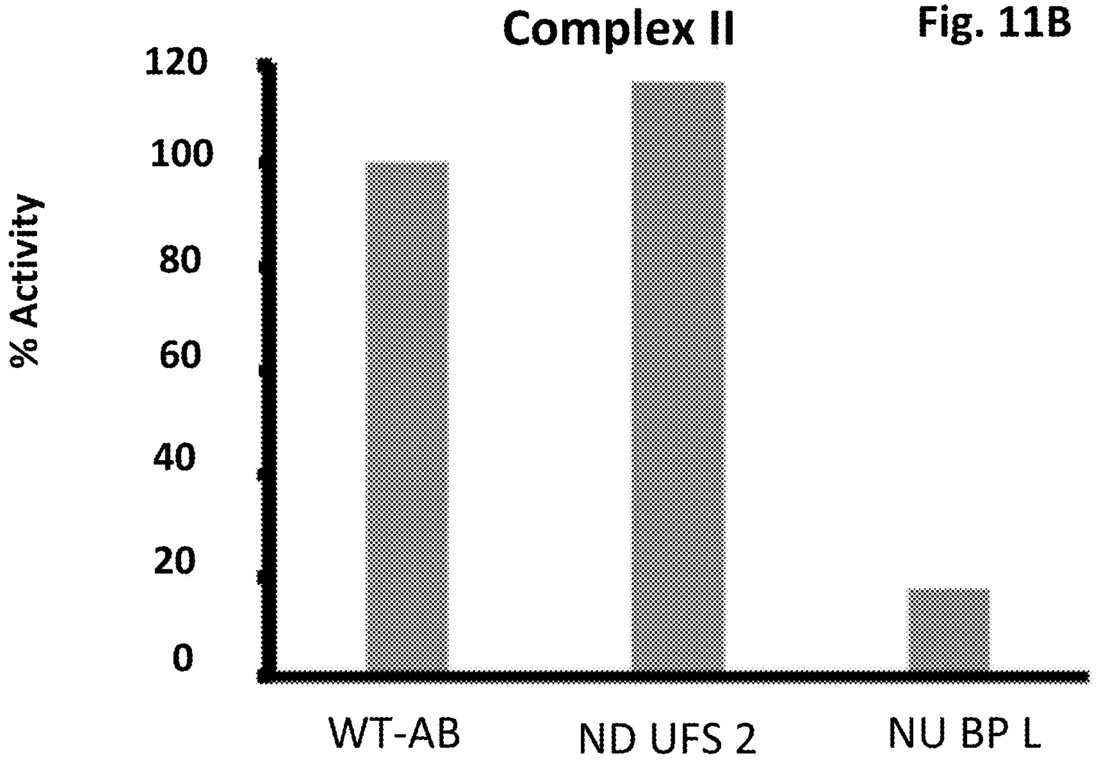
Figure 11C:
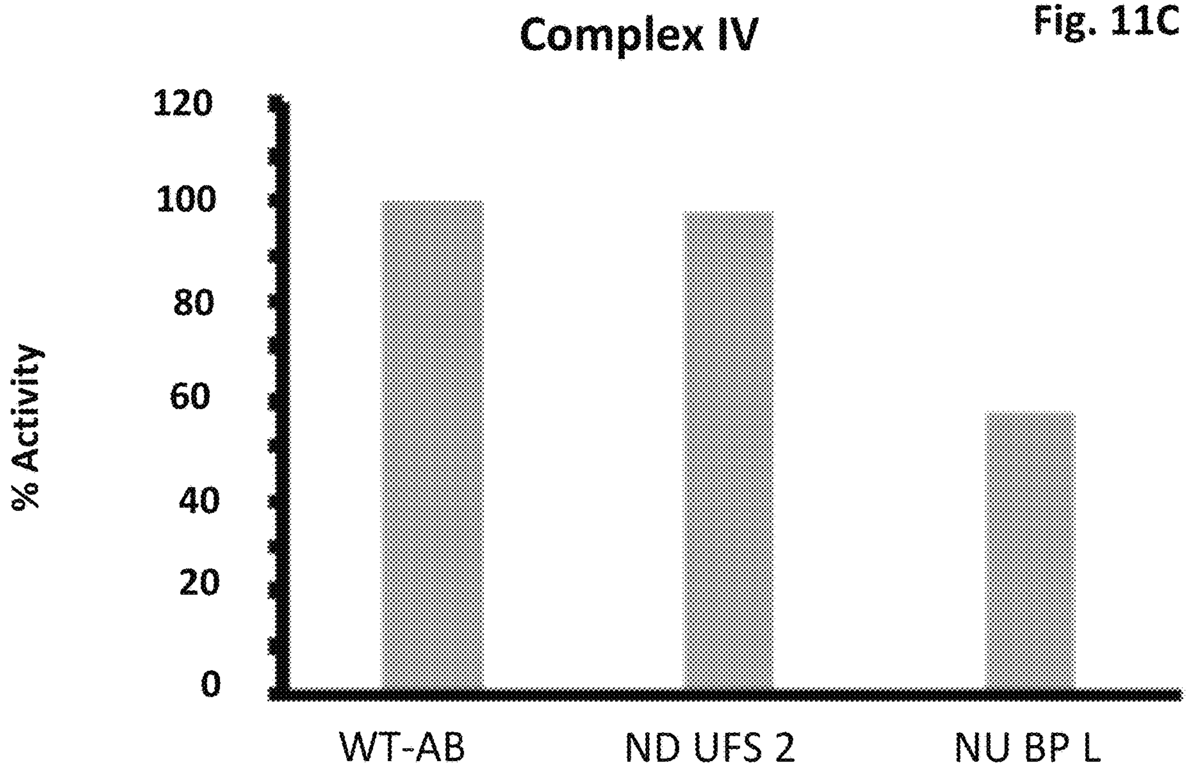

Using CRISPR-Cas9 technology, we have generated NUBPL knockout fish lines (68% homology) and a specific point mutation line with NUBPL c.693+1G>A mutation and the c.815-27T>C; c.166G>A found in a NUBPL disease patient. NUBPL F0 in-cross showed a decreased brood size of 72.5% (four biological replicates, n=80) compared to wild-type. The Electron Transport Chain activity of CI, CII and CIII of AB (wild-type) was compared against the CI mutant NDUFS2 and the F0 NUBPL in-cross. Notably, preliminary analysis suggests NUBPL mutants displays a reduction in CI enzymatic activity of 20% compared to AB and even greater 80% reduction in CII enzymatic activity. See FIG. 11A-11C.

Figure 11D:
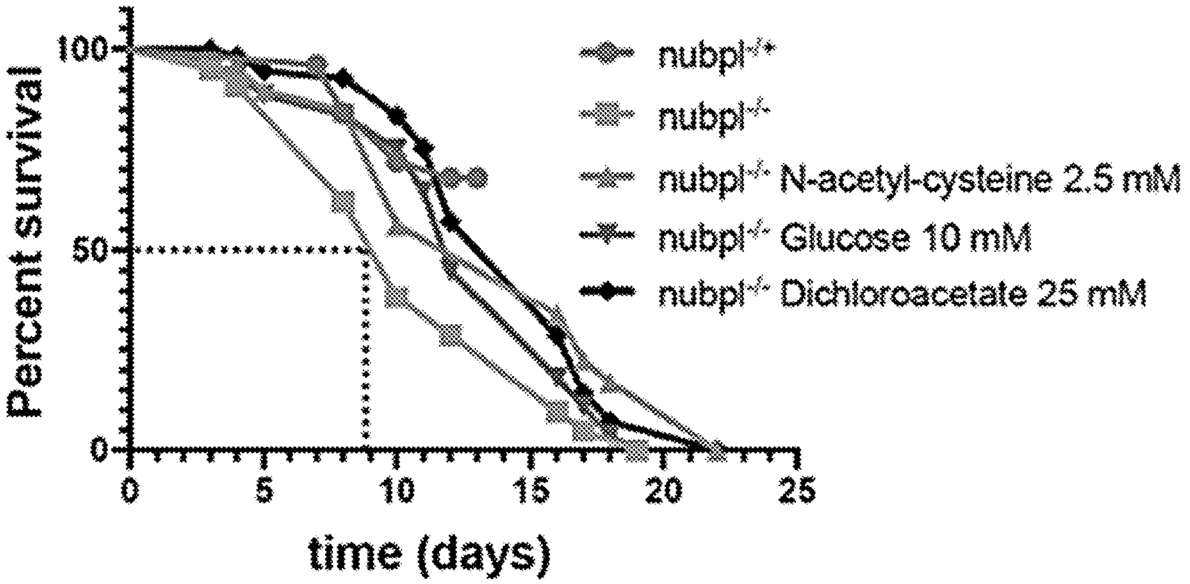

These animal models can be used to advantage for identifying new agents useful for the treatment of mitochondrial and other respiratory chain disorders. FIG. 11D shows that glucose and N-acetylcysteine improve lifespan in a genetic *C. elegans* NUBPL$^{-/-}$ model of Complex I disease. NUBPL is a nuclear gene-encoded complex I assembly factor, in which autosomal recessive (biallelic) mutations cause severe human mitochondrial discase manifesting with cerebellar ataxia and Leigh syndrome. Our data shows that homozygous mutant NUBPL$^{-/-}$ worms have reduced median lifespan relative to wild-type controls (NUBPL$^{+/-}$, blue line with circle marks—incomplete data due to contamination of that sample), which can be significantly rescued toward that of wild-type animals with either Glu 10 mM, NAC 2.5 mM, or dichloracetate (DCA at 25 mM. which a pyruvate dehydrogenase (PDH) enzyme activator by inhibiting the kinase that phosphorylates it to inactivate it). These data indicate results of a single biological replicate experiment. They demonstrate the broader applicability of glucose and NAC therapy to mitochondrial complex I diseases to other genetic etiologies beyond NDUFS2 disease.

References for Example II

1. Swalwell, H., et al., Respiratory chain complex I deficiency caused by mitochondrial DNA mutations. European journal of human genetics: EJHG, 2011. 19(7): p. 769-775.
2. Smeitink, J. A., et al., Cell biological consequences of mitochondrial NADH: ubiquinone oxidoreductase deficiency. Curr Neurovasc Res, 2004. 1(1): p. 29-40.
3. Bych, K., et al., The iron-sulphur protein Ind1 is required for effective complex I assembly. The EMBO journal, 2008. 27(12): p. 1736-1746.
4. Sheftel, A. D., et al., Human ind1, an iron-sulfur cluster assembly factor for respiratory complex I. Molecular and Cellular Biology, 2009. 29(22): p. 6059-6073.
5. Falk, M. J., et al., Probucol ameliorates renal and metabolic sequelae of primary CoQ deficiency in Pdss2 mutant mice. EMBO molecular medicine, 2011. 3(7): p. 410-427.
6. McCormack, S., et al., Pharmacologic targeting of sirtuin and PPAR signaling improves longevity and mitochondrial physiology in respiratory chain complex I mutant *Caenorhabditis elegans*. Mitochondrion, 2015. 22: p. 45-59.

7. Peng. M., et al., Inhibiting cytosolic translation and autophagy improves health in mitochondrial disease. Human molecular genetics, 2015. 24(17): p. 4829-4847.

EXAMPLE III

Robust Animal Models of Mitochondrial Dihydrolipoamide Dehydrogenase (DLD) Deficiency and Use Thereof for Identifying Agents Having Therapeutic Efficacy Dihydrolipoamide dehydrogenase (DLD) functions as the E3 subunit of three mitochondrial enzyme complexes: branched chain alpha-ketoacid dehydrogenase (BCKDH) complex, α-ketoglutarate dehydrogenase (αKGDH) complex, and pyruvate dehydrogenase (PDH) complex. DLD deficiency is a condition that can vary in age of onset, symptoms and severity. The condition may be characterized by early-onset lactic acidosis and delayed development (most commonly); later-onset neurological dysfunction; or adult-onset isolated liver disease. Signs and symptoms may include lactic acidosis shortly after birth; hypotonia and lethargy in infancy; feeding difficulties; seizures; and various other health issues. Liver problems can range from hepatomegaly to life-threatening liver failure. Symptoms often occur in episodes that may be triggered by illness or other stresses on the body. Many affected infants do not survive the first few years of life; those who survive through carly childhood often have growth delay and intellectual disability. Some with onset later in childhood may have neurological dysfunction with normal cognitive development. DLD deficiency is caused by mutations in the DLD gene and is inherited in an autosomal recessive manner.

The signs and symptoms of DLD deficiency can vary widely among affected people. Early-onset DLD deficiency typically appears in early infancy with decreased muscle tone (hypotonia), lethargy, and lactic acidosis. Lactic acidosis can cause nausea, vomiting, severe breathing problems, and an abnormal heartbeat. Symptoms typically occur in episodes that may be triggered by illness, injury, or other stresses on the body. Affected infants often do not survive their initial episode or may die within the first few years of life during a recurrent episode. Children who live beyond the first two to three years often have growth delays and neurological problems such as intellectual disability, spasticity, ataxia, and seizures. However, normal intellect has been reported in a few people with the early-onset form of DLD deficiency.

There are currently no consensus recommendations for the management of dihydrolipoamide dehydrogenase (DLD) deficiency. Management can be hard because various metabolic pathways are impacted, and 3 enzyme complexes are involved. Deficiencies in enzyme pathways vary depending on the specific mutation(s) each affected person has.

Unfortunately, the treatments that have been attempted in children with the early-onset neurologic form do not appear to significantly alter the course of the disease. Even with treatment, children often do not survive infancy or have varying degrees of chronic neurologic impairment if they survive the initial episode. Depending on individual enzyme complex deficiencies, treatment may involve certain dietary restrictions or certain diets; use of medical foods; and/or supplementation of specific amino acids or other substances.

As in the previous examples, *C. elegans* was employed. Lifespan, activity, and DLD-1 protein expression were studied in DLD-1(tm4879) heterozygous mutant worms harboring a 230 base-pair deletion. DNA agarose gel electrophoresis of *C. elegans* dld-1 gene PCR amplified from N2 and dld-1 worms demonstrated worms were heterozygous for the dld-1 deletion. Quantification of DLD protein was performed by ImageJ.

Figure 12A:
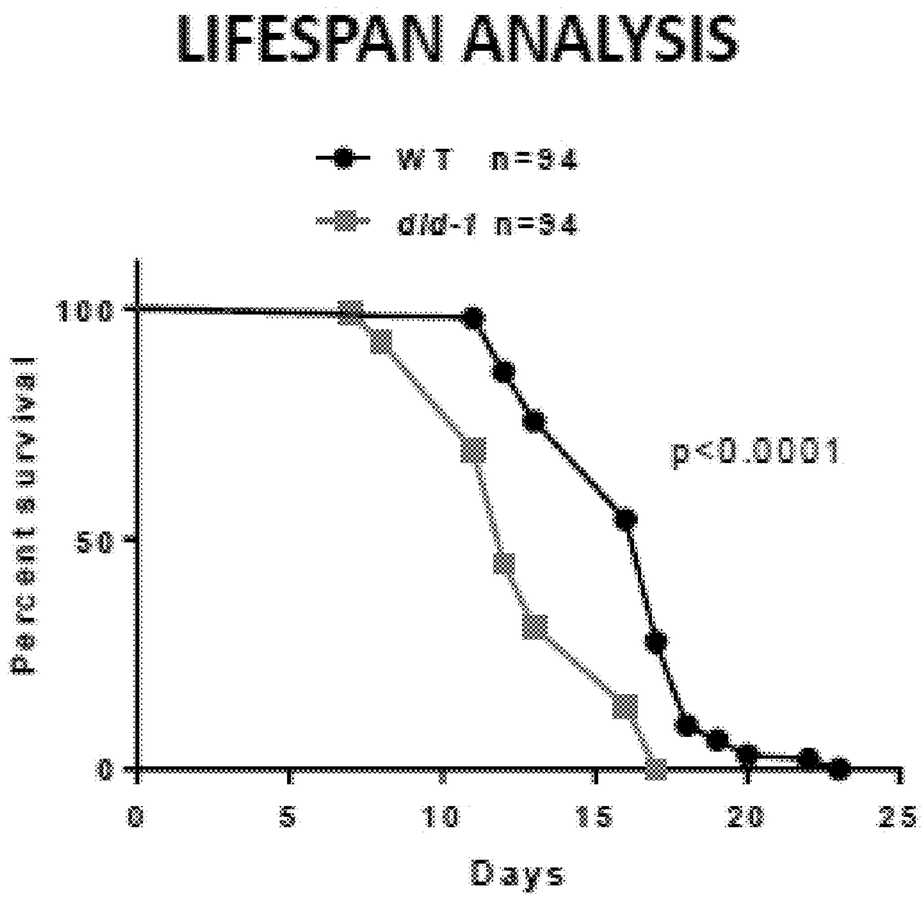
FIGS. 12A-12B. *C. elegans* dld-1 mutant has decreased lifespan and activity.
Figure 12B:
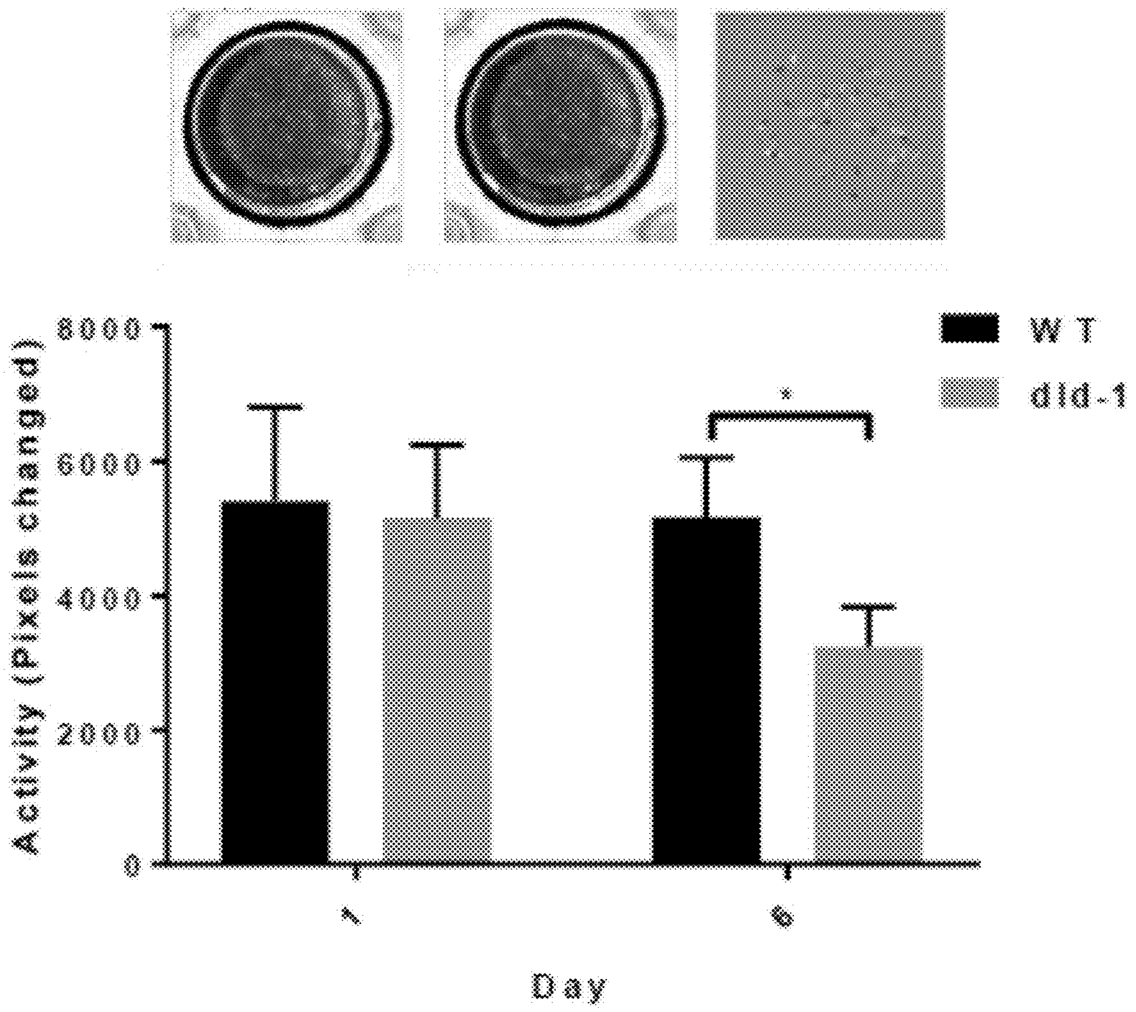
Figure 13A:
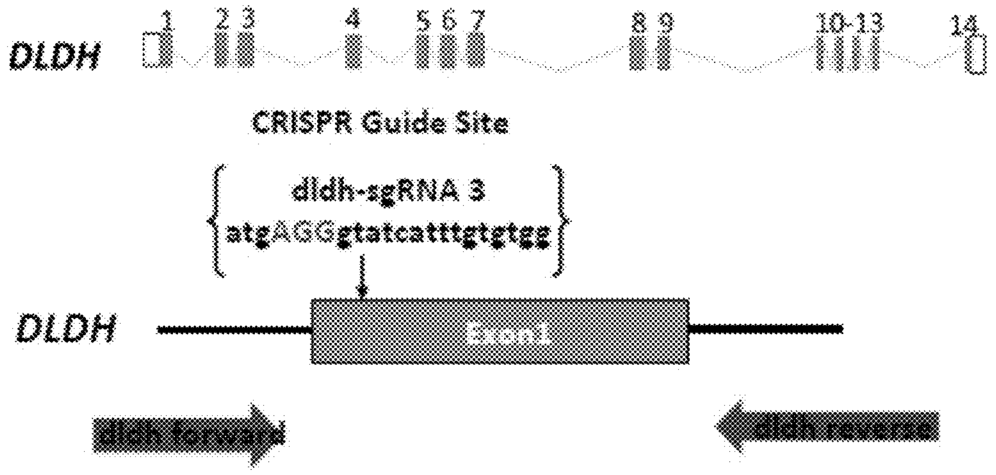
FIGS. 13A-13C.
Figure 13B:
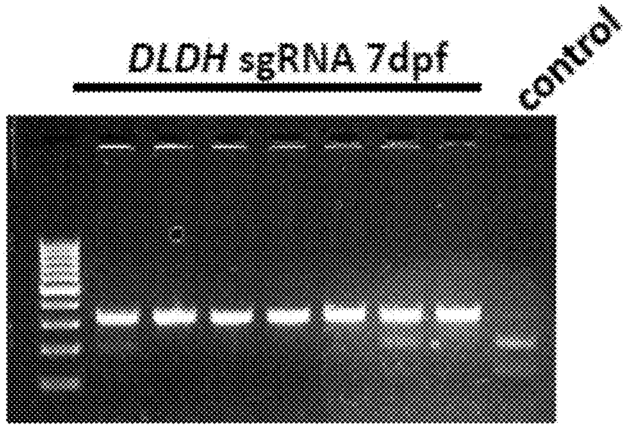
Figure 13C:
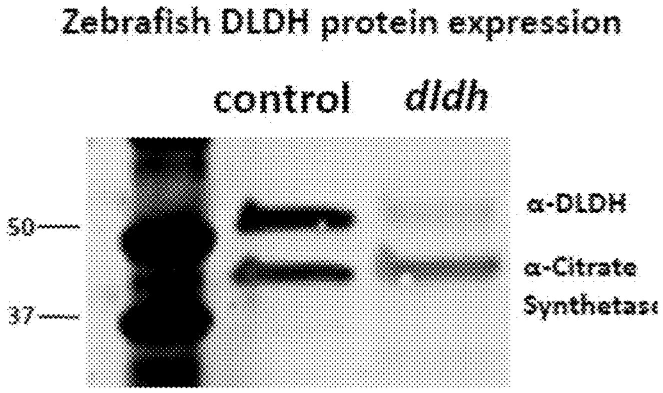
Figure 14A:
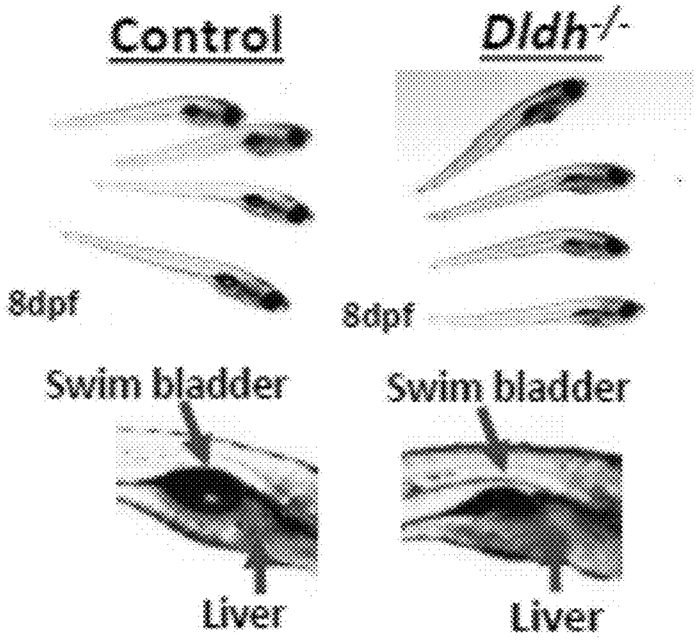
Figure 14B:
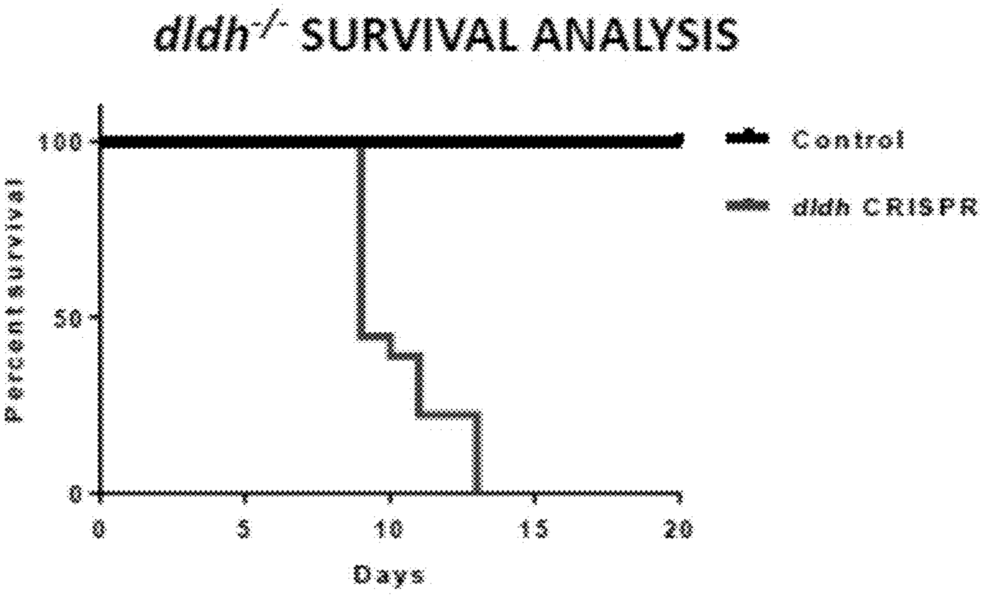

*C. elegans* dld-1+/− heterozygous mutant worms display hallmarks of mitochondrial dysfunction such as decreased lifespan and activity. (FIGS. 12A, 12B), although this is likely attributed to their balancer chromosomal mutation (unc) since homozygosity for DLD knockout is lethal in *C. elegans*. While we have employed a previously identified *C. elegans* mutant, RNAi can also be employed to characterize variable to complete gene knockout mutants. DLDH deletion zebrafish mutants lacking a portion of exon 1 were generated using CRISPR/Cas9 gene editing via microinjection at the 1-cell stage. (FIG. 13). Animal viability, organ development, swim behavior, DLD-1 protein expression, and electron transport chain enzyme activity analyses were evaluated in DLDH mutant relative to AB (wild-type) zebrafish. Liver physiology was studied by Oil Red O staining and transmission electron microscopy. FIG. 14 shows that dldh−/− Zebrafish display enlarged liver and failure to thrive. Control and dldh CRISPR injected Zebrafish Larvae lateral viewed at 1.6× magnification are shown in FIG. 14A. dldh−/− larvae show swollen liver and deflated swim bladder compared to wild-type controls at 8 dpf. FIG. 14B. Survival analysis comparing control and dldh−/− zebrafish, N=30 larvae for each group. Death was defined by absence of a heartbeat. FIGS. 14C and 14D show protection from rotenone induced Complex I dysfunction using the three component composition comprising NAC, NA and glucose.

Figure 15A:
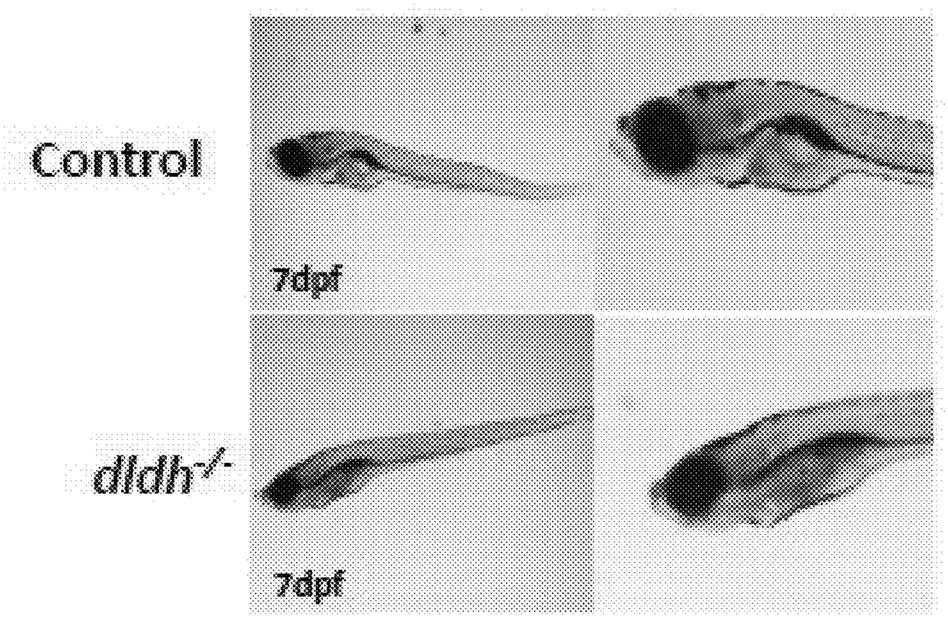
FIGS. 15A-15B.
Figure 15B:
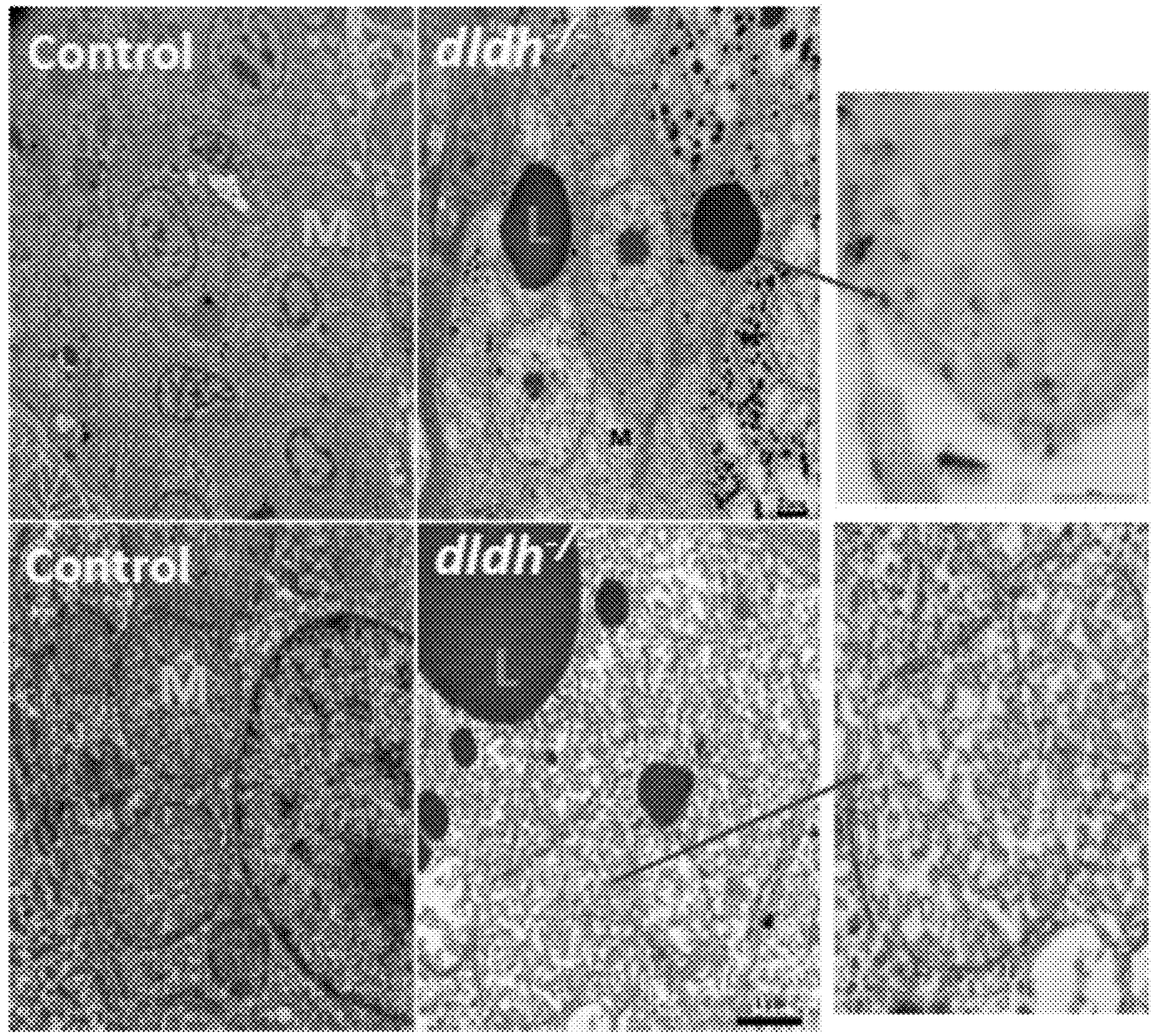
Figure 16A:
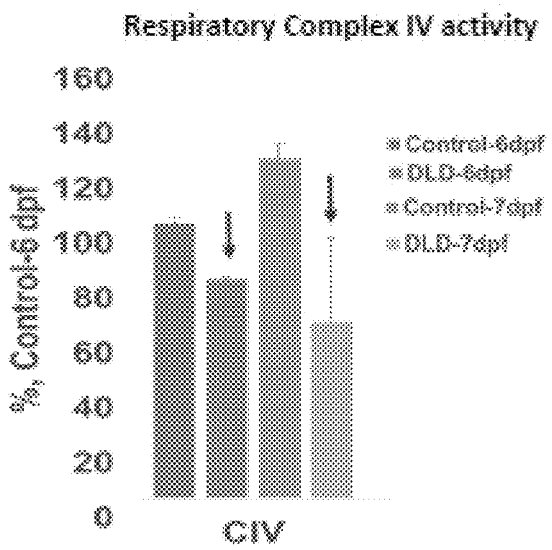
FIGS. 16A-16B. Reduced Complex IV activity and mitochondrial degeneration in dldh−/− Zebrafish muscle.

Lipids also accumulated in dldh−/− Zebrafish liver as shown in FIGS. 15A and 15B. Reduced Complex IV activity and mitochondrial degeneration was also observed in dldh−/− Zebrafish muscle. FIG. 16A shows electron transport chain Complex IV enzyme activity analysis of zebrafish lysate at 6 dpf and 7 dpf. Each bar represents 2 biological replicates of ~30 larvae. Values are normalized to citrate synthase. Bars indicate mean and standard deviation. EM analysis of tail muscle in control and dldh−/− larvae at 7 dpf. EM micrographs show degenerating mitochondria (M) in and dldh−/− larva compared to controls. See FIG. 16B. dldh−/− mitochondria are swollen with loss of mitochondrial matrix density and possible cristae damage, while mitochondria structure is preserved in wild-type controls.

RNAi studies confirmed that DLD-1 deficient worms display reproductive and developmental defects. DLD depletion in *C. elegans* was achieved by feeding wild-type (N2 Bristol) worms *E. coli* expressing a dsRNA targeting DLD-1 messenger RNA. Brood size, survival, activity, growth (length), DLD-1 expression, and mitochondrial unfolded protein response ($UPR^{mt}$) were quantified in the resulting DLD-1" animals. High throughput semi-automated analyses of animal growth (length) and mitochondrial stress response ($UPR^{mt}$) were also measured in day 1 adult worm populations using the COPAS Biosorter (Union Biometrica).

Therapeutic impact on DLD-$1^{-/-}$ *C. elegans* $UPR^{mt}$ induction and growth (length), as well as DLDH−/− zebrafish survival, liver morphology, and swimming behavior were tested for 5 therapies, including a PDH activator (dichloroacetate, DCA), PDH cofactors (thiamine, riboflavin, lipoic acid), and a lipid lowering drug that functions as a signaling modifier to inhibit mTORCI and activate AMPK and PPAR (probucol).

TABLE I shows the results obtained from a variety of agents tested in this model.

| | Size | HSP-6P::GFP |
|---|---|---|
| Water Soluble Drugs | | |
| Nicotinic Acid (1 mM) | No Effect | No Effect |
| Riboflavin (10 uM) | Increase | Increase |
| Thiamine (25 mM) | Increase | Decrease |
| L-Carnitine (100 uM) | No Effect | No Effect |
| Folinic Acid (10 uM) | No Effect | Increase |
| Glucose (10 uM) | No Effect | Increase |
| DCA (25 mM) | No Effect | Decrease |
| Cysteamine (100 um) | No Effect | No Effect |
| NAC (2.5 Mm) | No Effect | No Effect |
| AICAR (500 uM) | No Effect | Decrease |
| Hydralazine (200 uM) | Increase | No Effect |
| Lithium Chloride (10 mM) | No Effect | Decrease |
| Cyclohexamide (2 uM) | No Effect | Increase |
| Arginine (10 mM) | No Effect | Increase |
| Taurine (800 uM) | Increase | Decrease |
| Taurine (8 mM) | In Process | In Process |
| DMSO Soluble Drugs | | |
| Resveratrol (50 uM) | Increase | Increase |
| Ethanol Soluble Drugs | | |
| Rapamycin (2.5 nM) | No Effect | No Effect |
| Probucol (5 uM) | No Effect | No Effect |
| Lipoic Acid (10 uM) | No Effect | Increase |
| Vitamin E (250 uM) | No Effect | Increase |

Figure 16B:
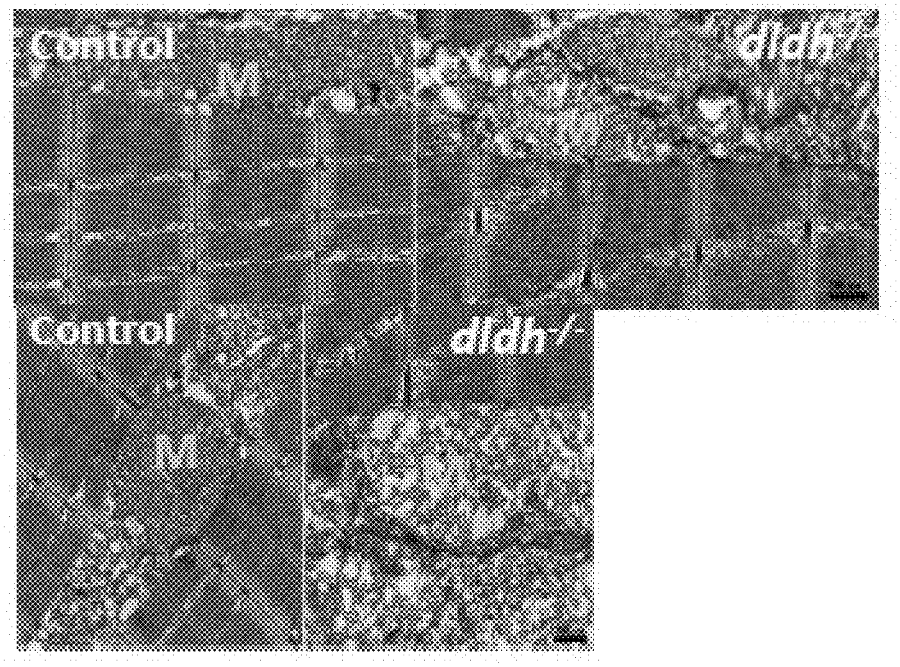
Figure 17C:
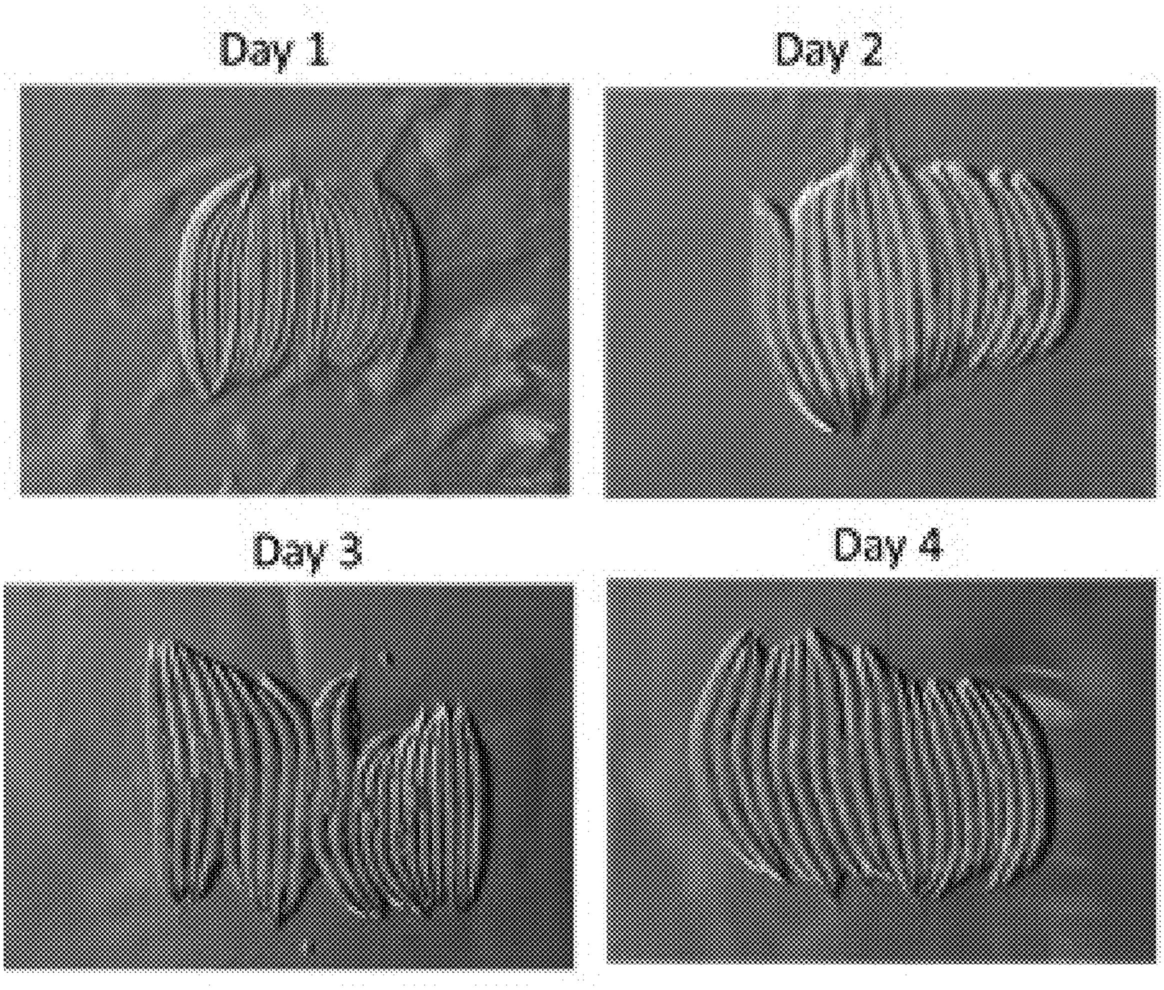
Figure 17D:
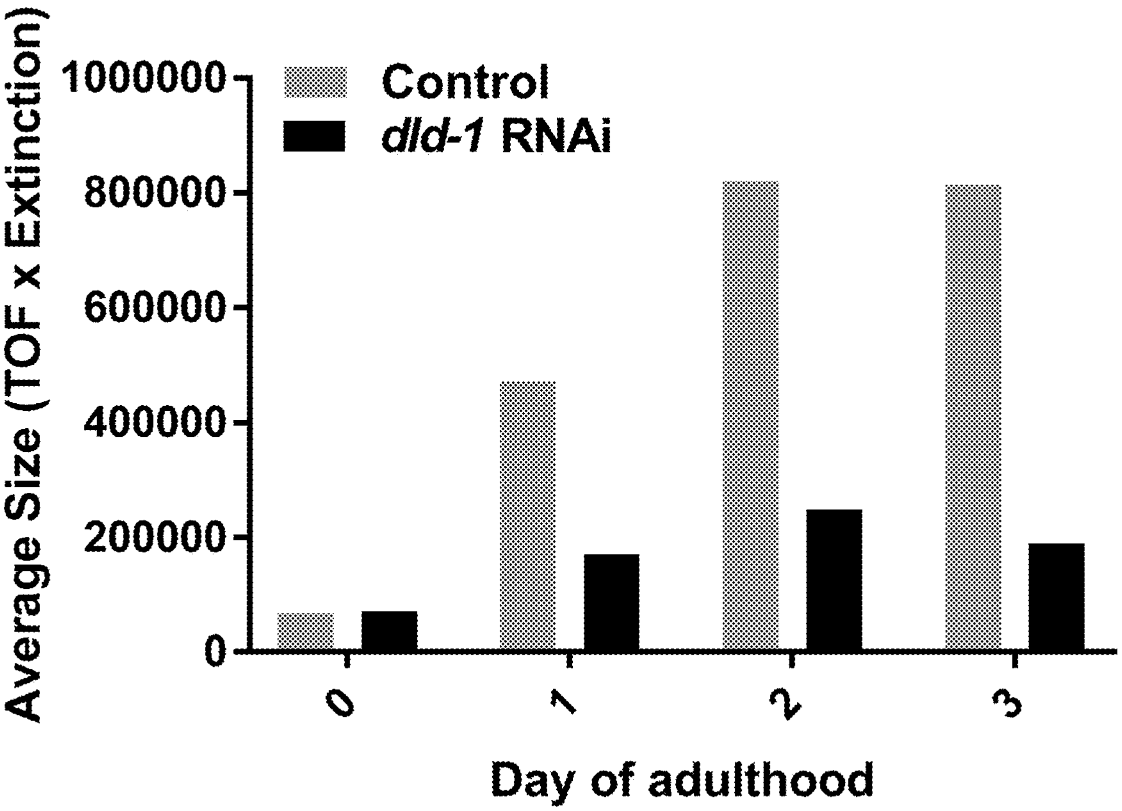
Figure 18A:
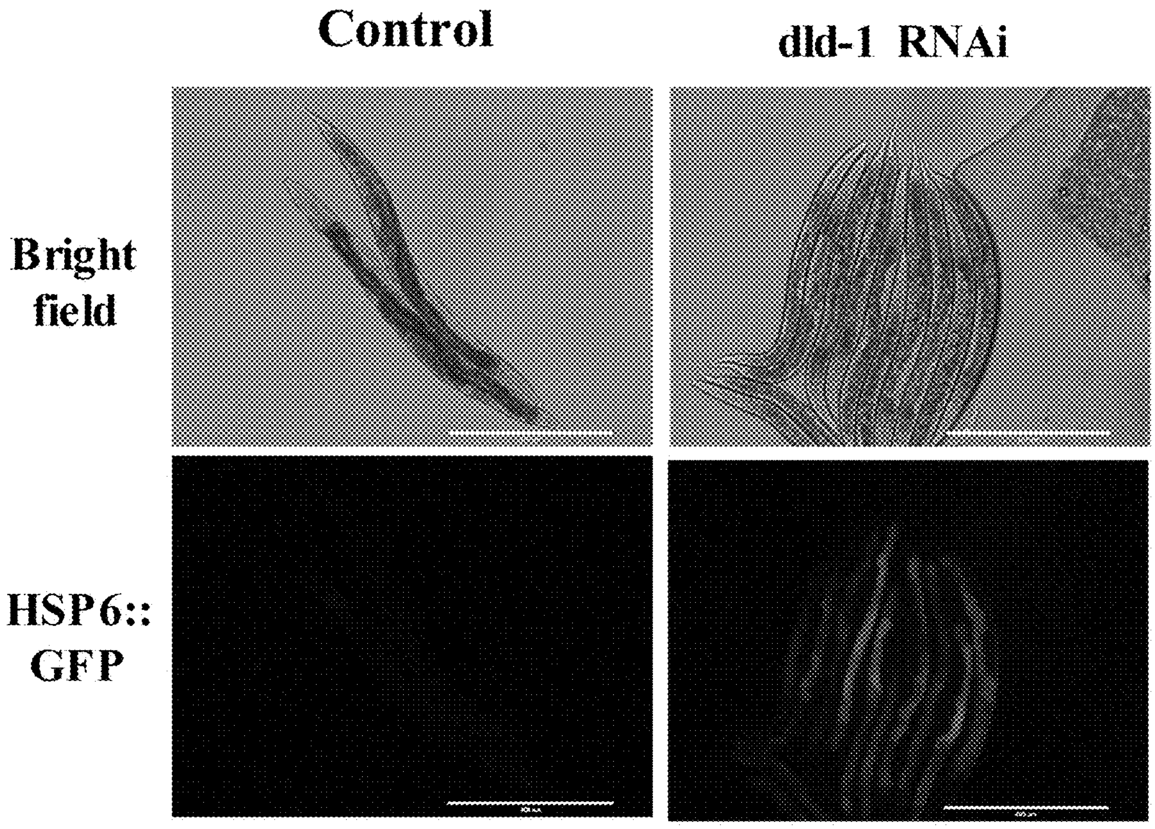
FIGS. 18A-18C.
Figure 18B:
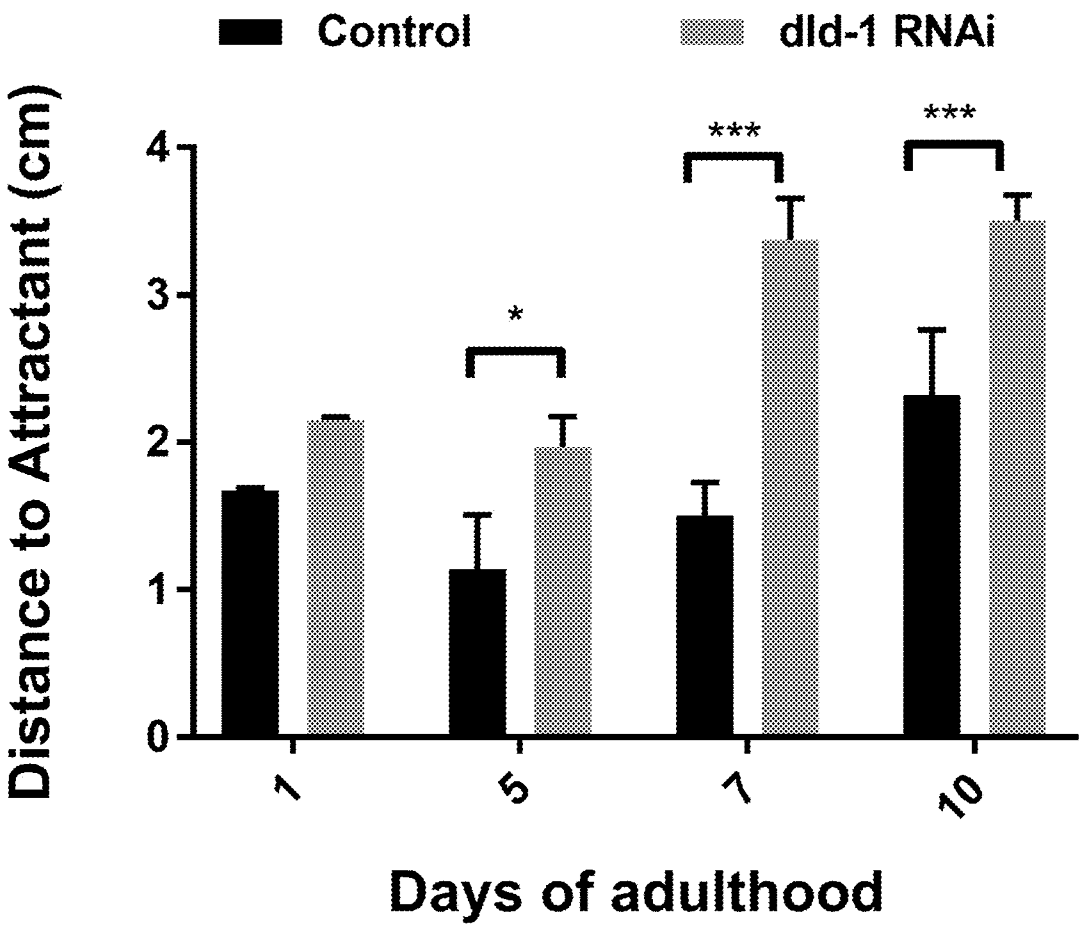
Figure 18C:
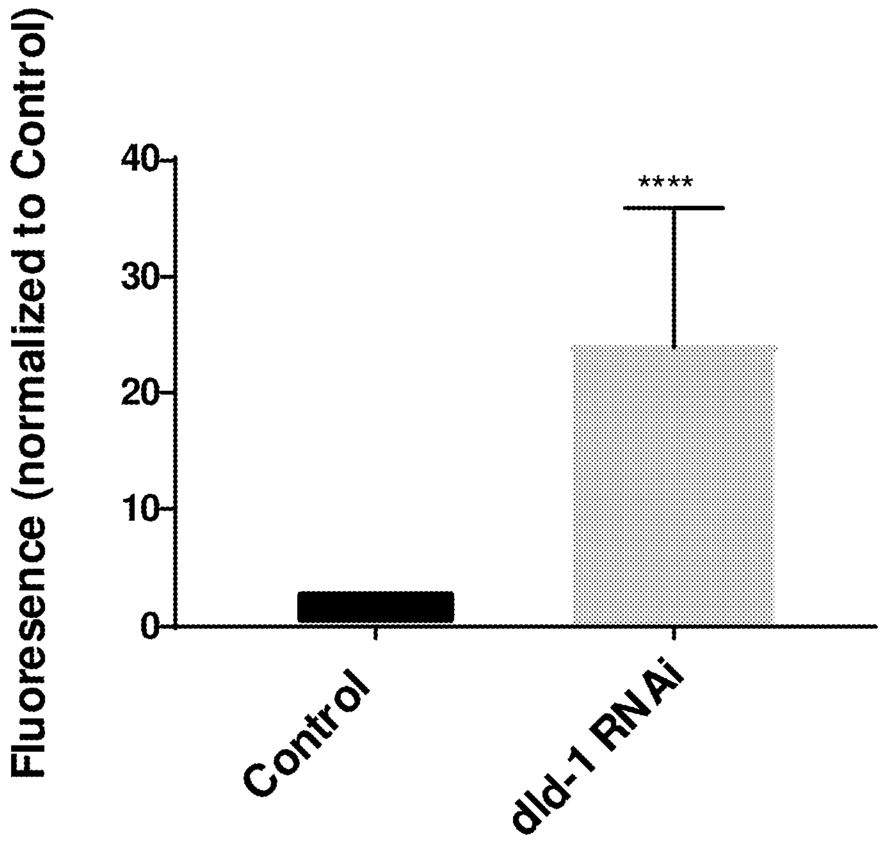
Figure 20A:
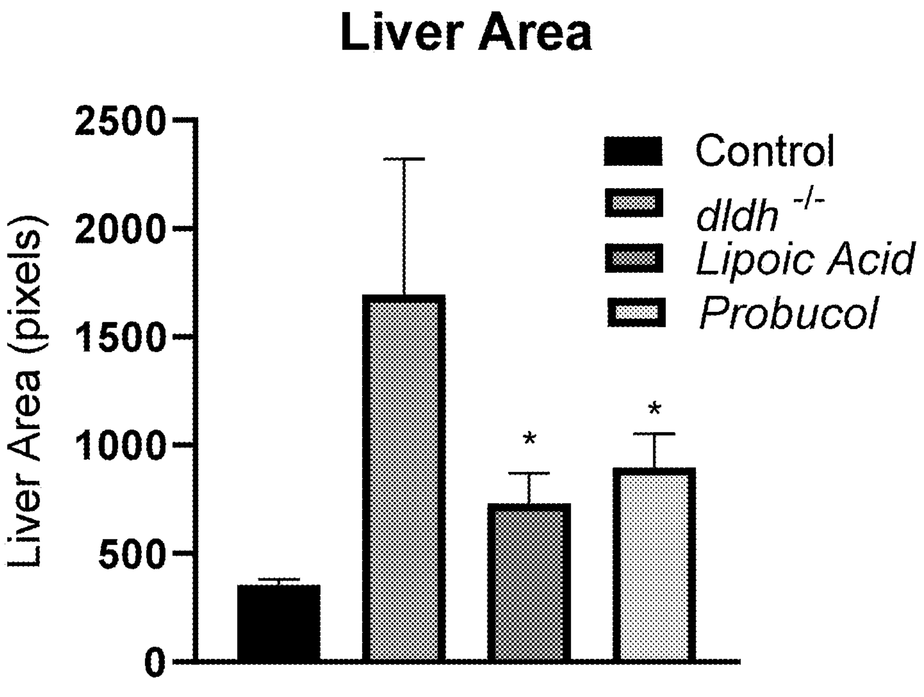
FIGS. 20A-20B: Treatment of zebrafish larvae from 2 dpf with 10 μM lipoic acid and 5 μM Probucol.
Figure 20B:
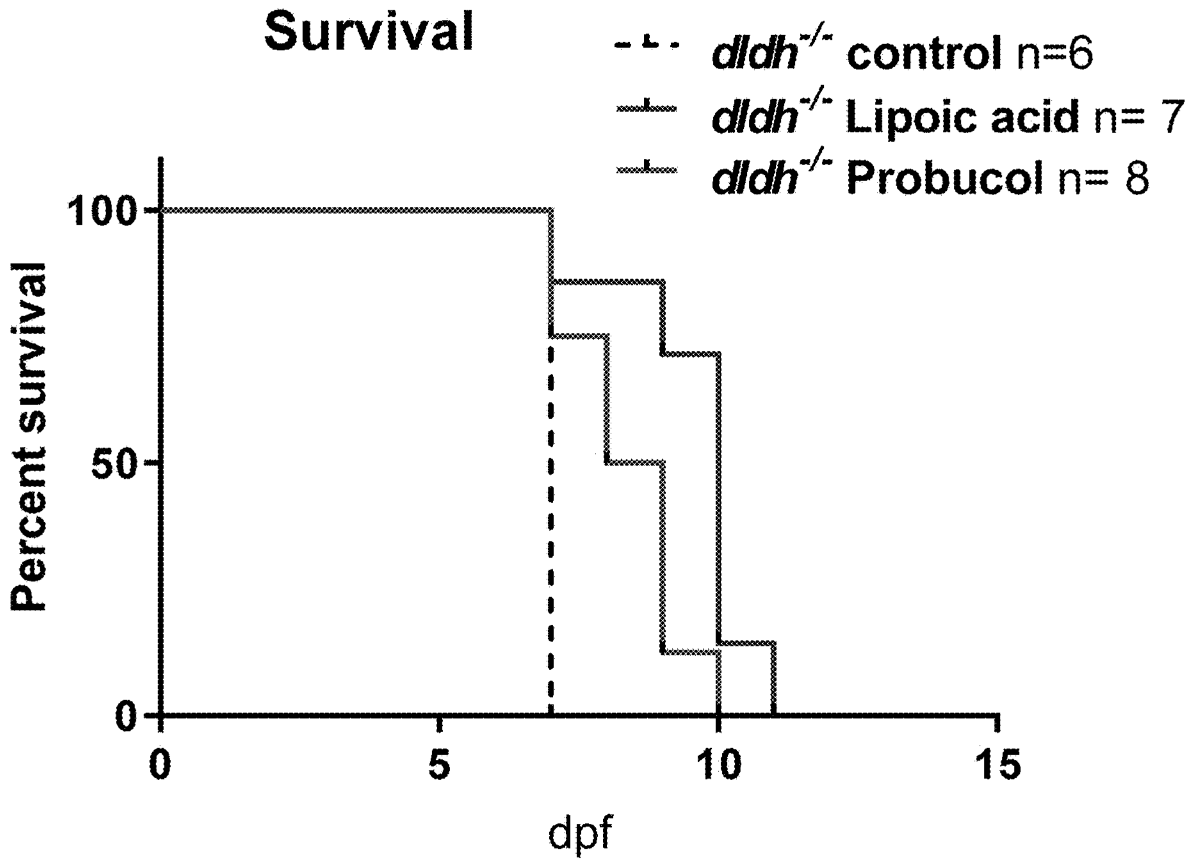

FIGS. 17A-17D show results obtained with worms were fed control plasmid or plasmid encoding RNAi that targets dld-1. FIG. 16B shows brood size analysis. FIGS. 17C and 17D show significant differences in worm size. FIGS. 18A-18C show that DLD-1 deficient worms display hallmarks of mitochondrial stress. FIG. 18 shows the effects of standard therapies on mitochondrial stress and animal development. FIG. 19A shows therapeutic efficacy of 25 mM DCA and 25 mM Thiamine on mitochondrial stress (induction of hsp-6p::GFP). Worms fed Control or dld-1 RNAi were treated with the therapies from birth and fluorescence intensity of the GFP signal was analyzed at adult day 1 as described above. FIG. 18B shows therapeutic efficacy of 50 uM Riboflavin and 25 mM Thiamine on animal size. Worms were treated with the therapies from birth and size was analyzed as described above at adult day 1. *P<0.005, *P<0.0005. See FIG. 20** which provides objective pre-clinical evidence for benefit of several treatments for use in human DLD disease patients.

*C. elegans*: RNAi resulted reduced DLD-1 expression by 90% in young adult worms, brood size by 90%, and adult growth (length) by 23% on adult day 3. Mutants had an ~8-fold mean increase in UPRmt as assessed by HSP6::GFP fluorescence, which was significantly rescued by treatment from early development with DCA (56% reduction) or thiamine (18% reduction) relative to untreated DLD-1−/− worms. The PDH cofactors riboflavin and thiamine significantly increased worm growth (length) by 33% and 16%, respectively.

Zebrafish: DLDH−/− zebrafish had grossly enlarged livers by 5 days post fertilization (dpf). DLDH−/− liver TEM showed pronounced mitochondrial degeneration with increased lipid droplets, confirmed by Oil-Red-O staining. Reduced swimming activity was seen at 7 dpf by automated behavioral analysis (Zebrabox), with 100% animal mortality occurring by 11 dpf. Remarkably, as shown in FIG. 36 pre-treatment of dldh mutant zebrafish larvae from 2 dpf with lipoic acid extended animal survival (FIG. 20B) by 3 days and rescued their liver phenotype (FIG. 20A, with a 58% decrease in liver size compared to untreated DLDH−/− larvae. Further, the metabolic modifier, probucol, also reduced liver disease by 49% compared to untreated mutant fish.

Conclusion

We have generated the first viable DLD disease translational models in any species. Specifically, DLD deficiency in both *C. elegans* and zebrafish replicates the classical hallmarks of mitochondrial and liver dysfunction typical of human DLD disease. Therapeutic modeling has provided objective evidence for benefit of several different treatment regimens used in human DLD disease patients.

EXAMPLE IV

Cysteamine Bitratrate and N-Acetylcysteine Rescue Brain Death and Neuromuscular Activity in a Novel SURF1-Knockout Zebrafish Animal Model of Leigh Syndrome SURF1 is a nuclear gene that encodes an assembly factor required for assembly of cytochrome c oxidase (complex IV). Complex IV (CIV) is final site of electron transfer in the electron transport chain, required for energy production in mitochondria. SURF1 transfers the correct form of heme into CIV. In bacteria, SURF1 transfers the correct heme from the biosynthesis complex CtaA/CtaB to subunit I of CIV. After the heme transfer, SURF1 protein comes apart and allows subunit II to bind to subunit I, after which the rest of CIV forms. SURF1 pathogenic mutations are a cause of Leigh Syndrome. Symptoms of this disorder include reduced complex IV assembly and activity, excessive lactic production. neurological disorder, seizures, + failure to thrive. Leigh syndrome commonly exhibits early childhood onset, although can be adult onset.

To model SURF1 disease in *D. rerio* (zebrafish), we employed CRISPR-Cas9 gene editing technology to create SURF1$^{-/-}$ mutants. These zebrafish are useful to identify aberrant behavior in the mutant fish that mimic SURF1 disease clinical symptoms, thereby facilitating pre-clinical screens for potential therapeutics that improve function in human patients. Two SURF1 mutant zebrafish lines were established. SURF1$^{-/-}$ strain Del1 contains a 23 basepair deletion in exon 6. SURF1−/− strain Del2 contains a 33 basepair deletion in exon 4.

Western Blot analysis has shown that the SURF1del1$^{-/-}$ animals lack SURF1 expression and have reduced COX4 expression. SURF1del2$^{-/-}$ zebrafish have reduced COX4 expression. CIV enzyme activity is reduced by 7 dpf by 90% in SURF1del1$^{-/-}$ and by 50% in SURF1del2$^{-/-}$ zebrafish larvae.

Results

Figure 21A:
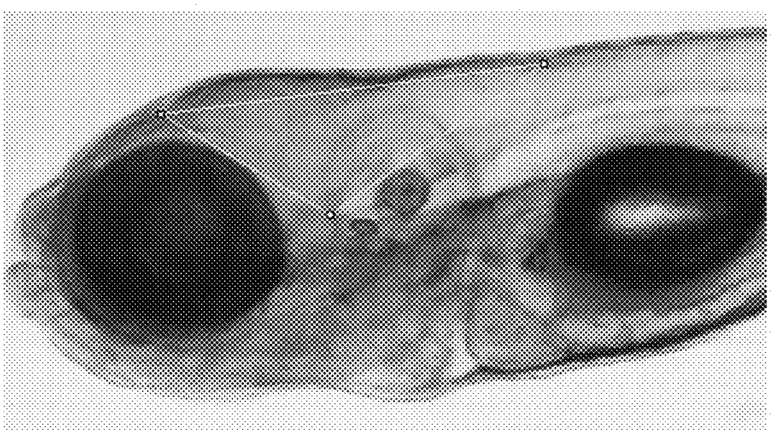
FIGS. 21A-21B. Brain (yellow triangle) is clear in controls (left panel), but grey in SURF1del−/− mutants after overnight azide exposure at 7 dpf (right panel), indicating brain death.
Figure 21B:
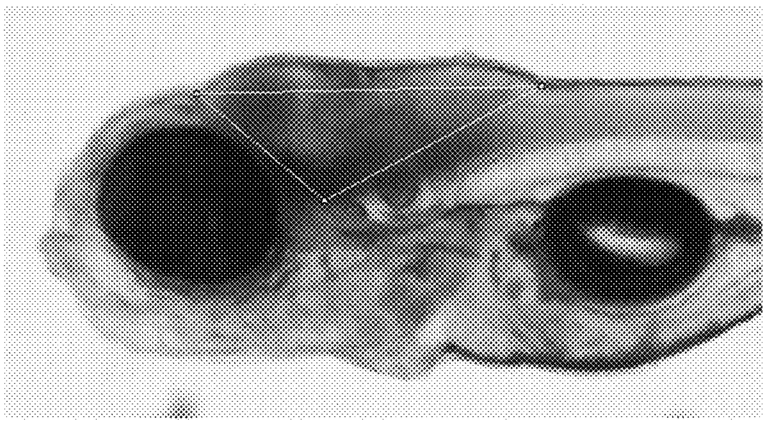
Figure 22A:
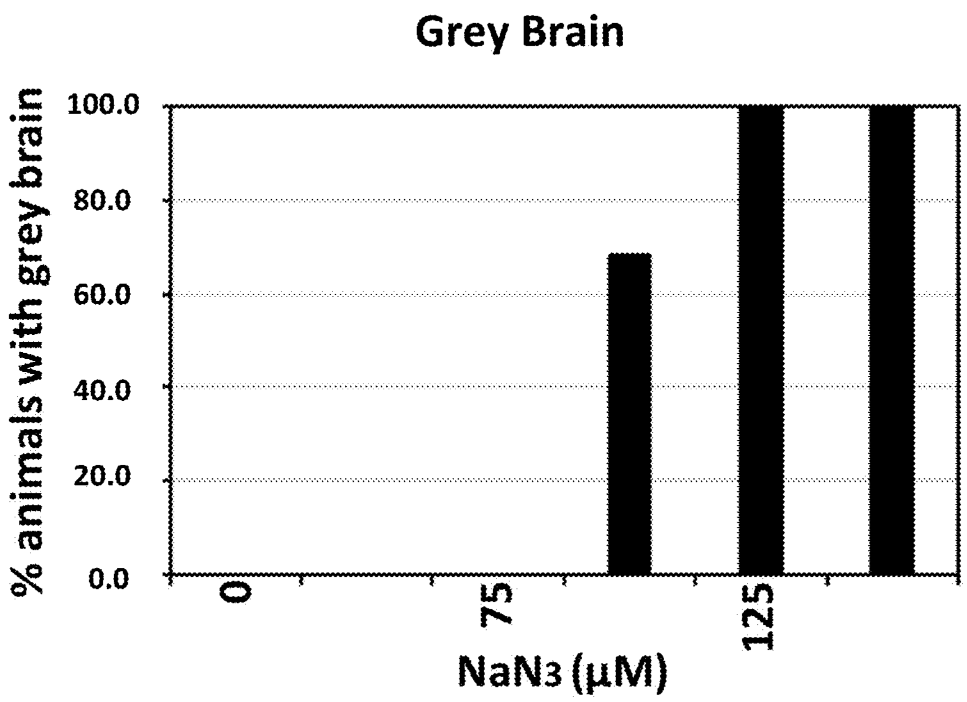
FIGS. 22A-22B. Wild-type zebrafish develop brain death by 7 dpf after exposure to 100 μM $NaN_3$ from 6 dpf, with complete penetrance of the brain death phenotype at 150 μM $NaN_3$ (FIG. 22A). SURF1-del1−/− zebrafish show azide hypersensitivity, with brain death onset at 40 μM $NaN_3$ and complete penetrance by 50 μM $NaN_3$ (FIG. 22B) from 6-7 dpf.
Figure 22B:
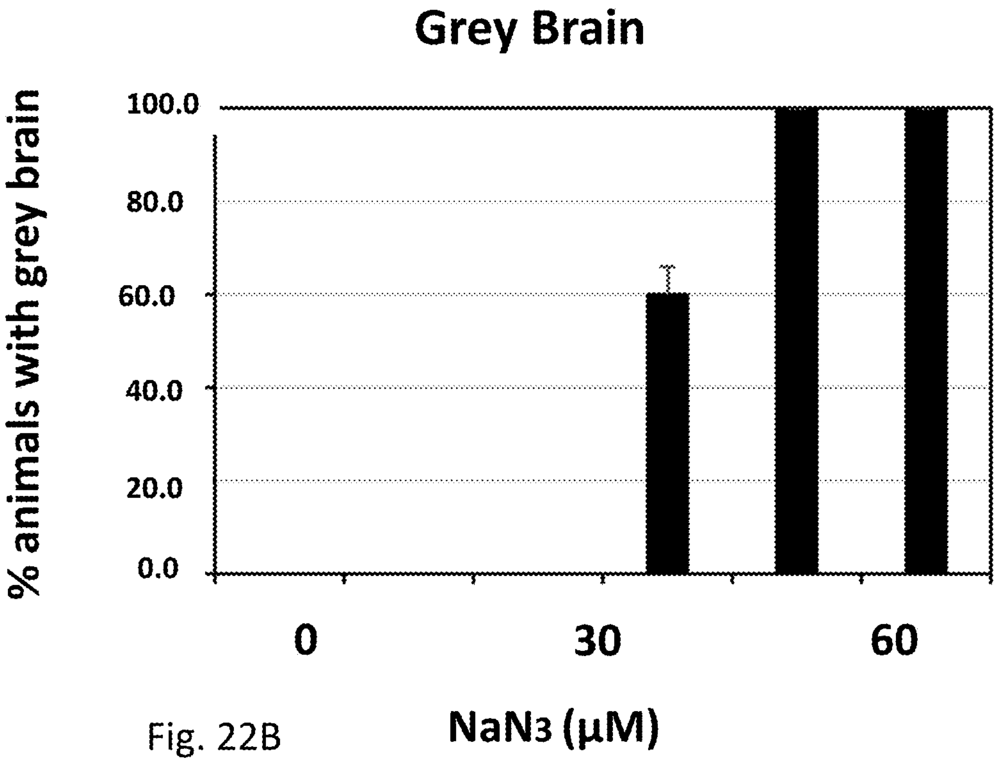
Figure 23C:
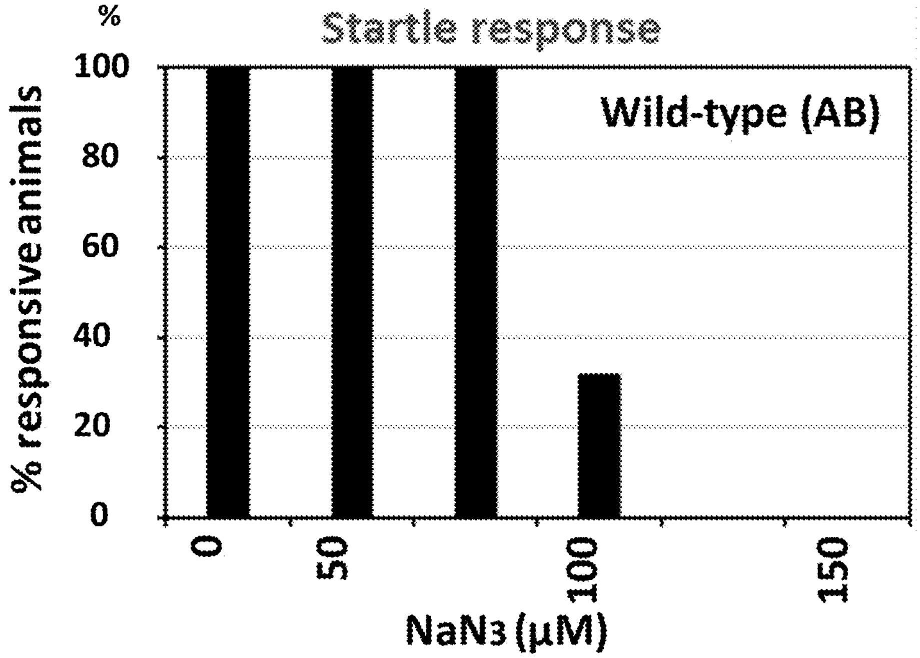
Figure 23D:
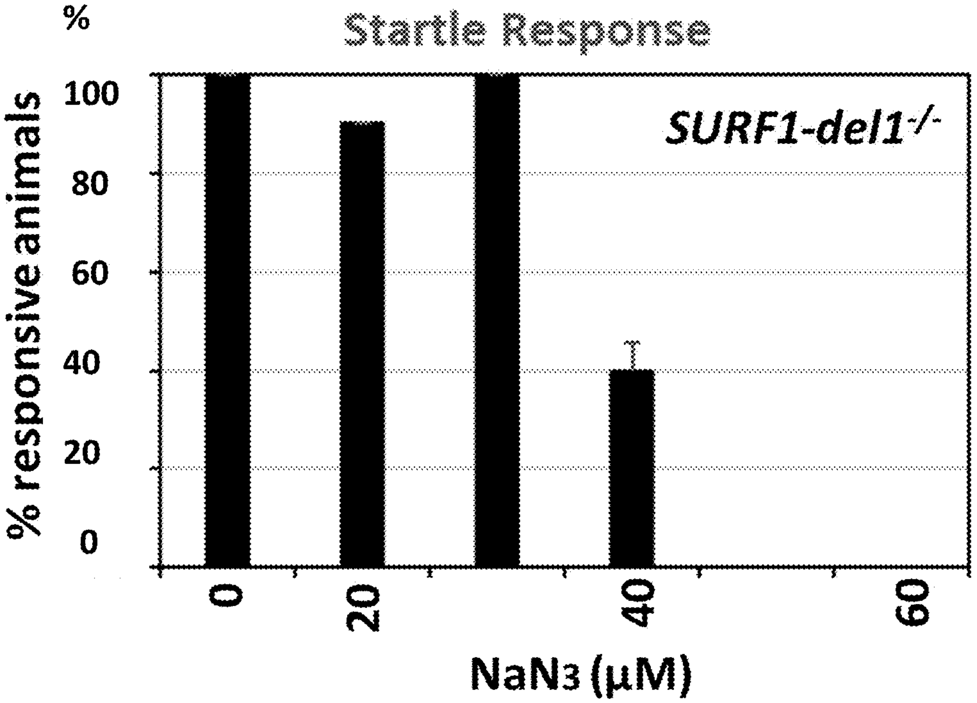

FIG. 21 shows that the brain (yellow triangle) is clear in controls (FIG. 21A, but grey in SURF1del$^{-/-}$ mutants after overnight azide exposure at 7 dpf (FIG. 21B), indicating brain death. FIGS. 22A and 22B shows that wild-type zebrafish develop brain death by 7 dpf after exposure to 100 μM $NaN_3$ from 6 dpf, with complete penetrance of the brain death phenotype at 150 μM $NaN_3$ (FIG. 22A). SURF1-del1$^{-/-}$ zebrafish show azide hypersensitivity, with brain death onset at 40 μM $NaN_3$ and complete penetrance by 50 μM $NaN_3$ (FIG. 22B) from 6-7 dpf. SURF1del1$^{-/-}$ zebrafish are hypersensitive to CIV inhibition with $NaN_3$, developing neuromuscular dysfunction. In FIG. 23, wild-type zebrafish display reduced heartrate and neuromuscular (startle) response at 100 μM azide from 6-7 dpf, further exacerbated at higher doses. SURF1-del1$^{-/-}$ zebrafish show azide hypersensitivity, with bradycardia and impaired neuromuscular function (reduced startle response) starting at 40 μM azide.

SURF1del1$^{-/-}$ zebrafish pre-treatment with N-acetylcysteine (NAC) or cysteamine bitartrate preserves neuromuscular function in 45 μM $NaN_3$. FIGS. 24A-24D show results when SURF1-del1$^{-/-}$ zebrafish were pre-treated from 5 dpf with either NAC or cysteamine bitartrate, exposed to 45 μM $NaN_3$ from 6 dpf, and assessed on 7 dpf. FIGS. 24A and 24B show NAC pre-treatment prevented brain death and neuromuscular dysfunction (preserved startle response.) from $NaN_3$ exposure. FIGS. 24C and 24D show cysteamine bitartrate treatment also prevented brain death (FIG. 24C) and neuromuscular dysfunction (preserve startle response, FIG. 24C) from $NaN_3$ exposure.

Figure 25A:
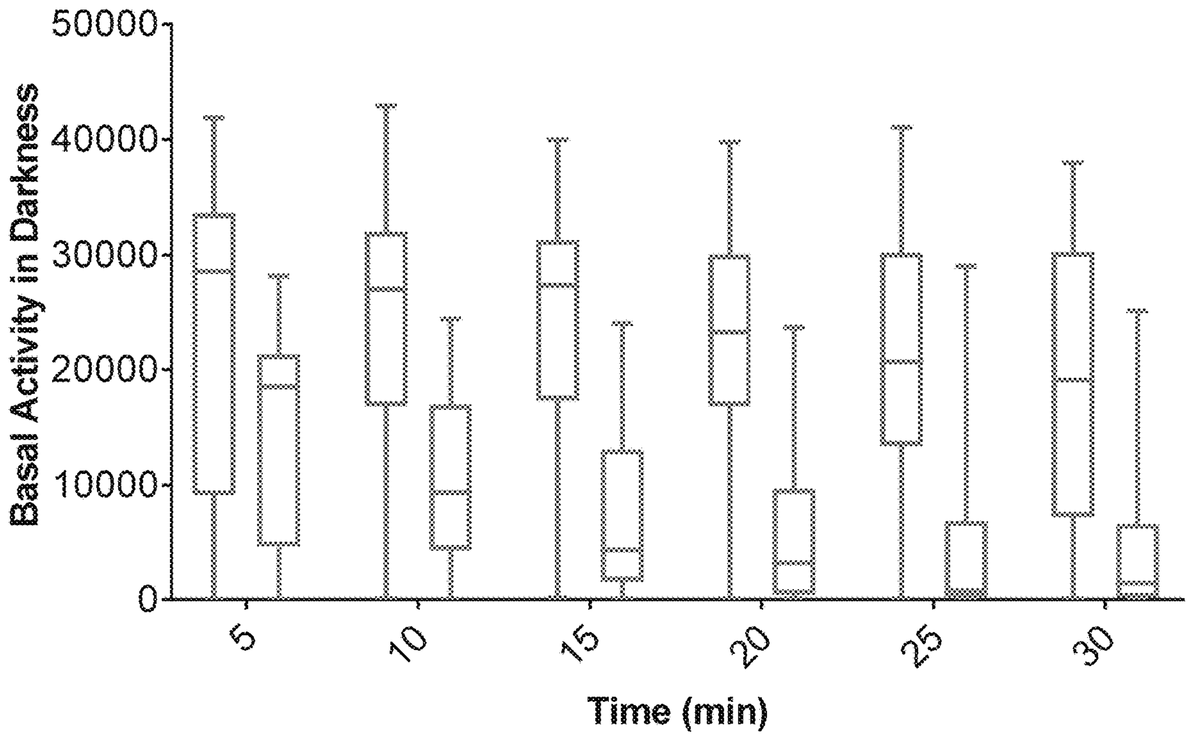
FIGS. 25A and 25B. SURF1del2−/− zebrafish have reduced swimming activity at baseline and with light/dark stress. Behavioral activity of SURF1-del2−/− zebrafish at 7 dpf (Zebrabox, Viewpoint) was quantified in darkness for 30 minutes (left panel.
Figure 25B:
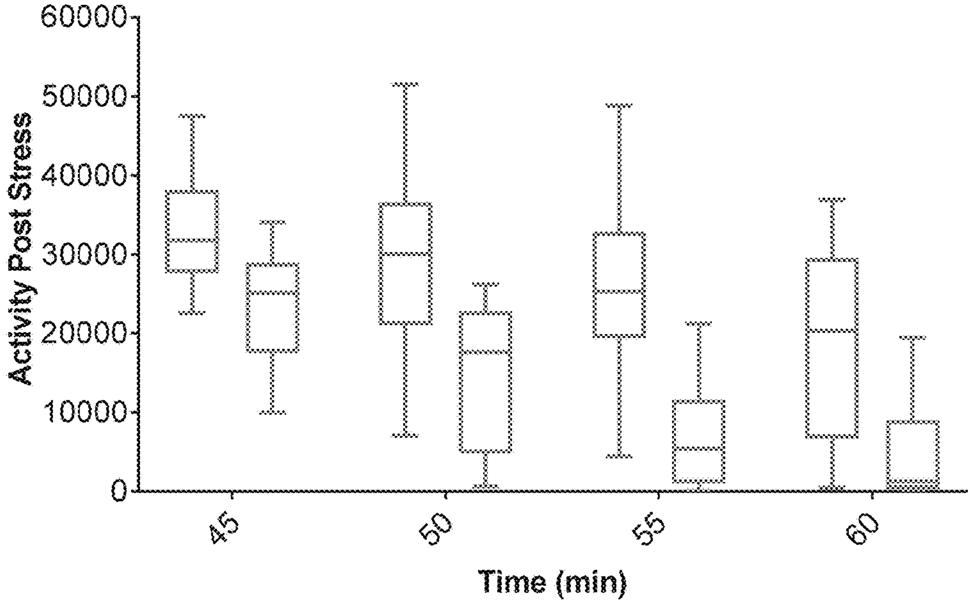
Figure 26:
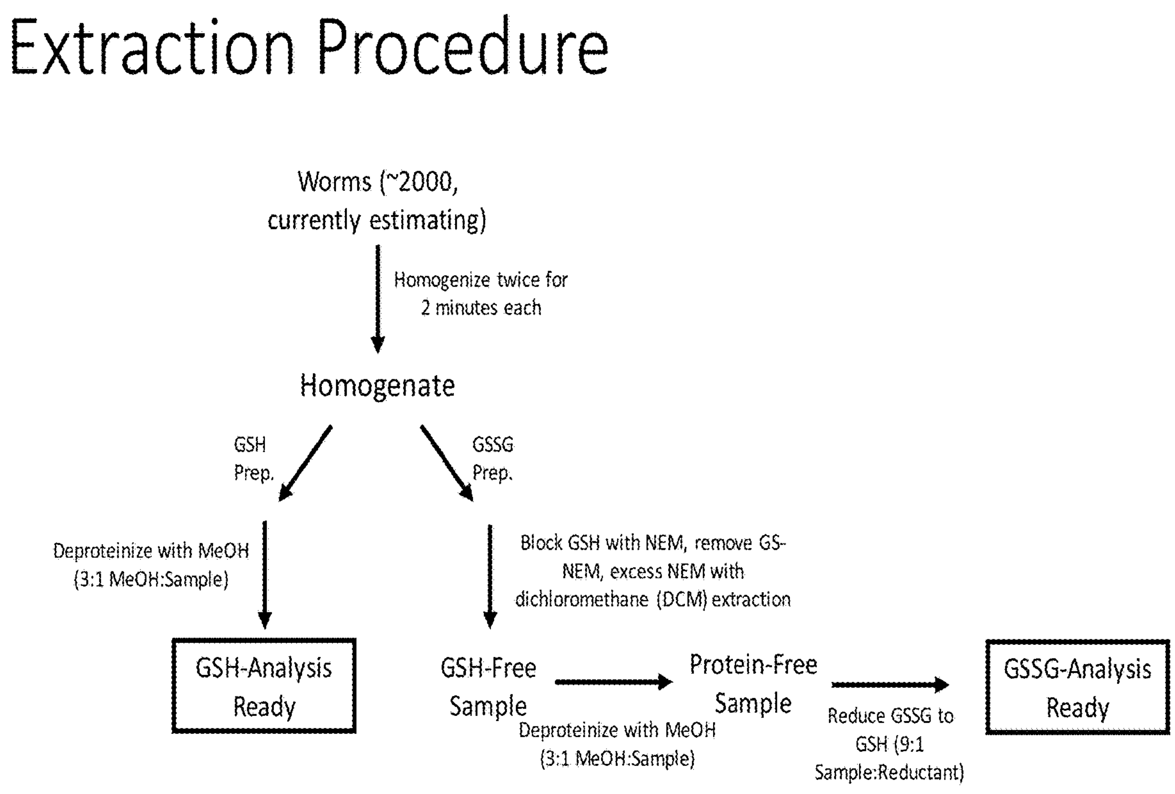
FIG. 26 provides a schematic overview of the GSH extraction procedure.
Figure 27A:
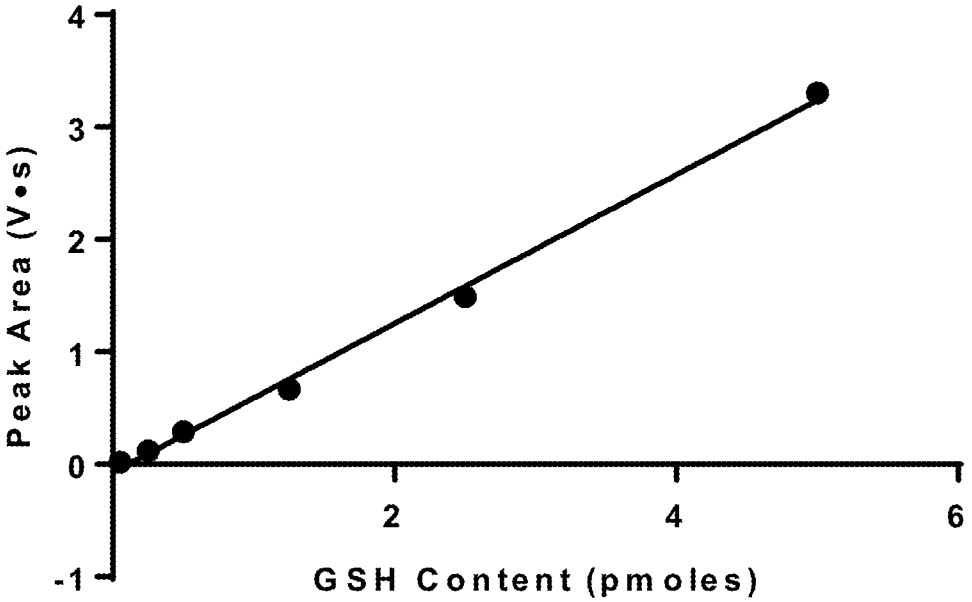
FIGS. 27A-27B. Standard curves for the HPLC-ECD assay (FIG. 27A) and the enzymatic assay (FIG. 27B).
Figure 27B:
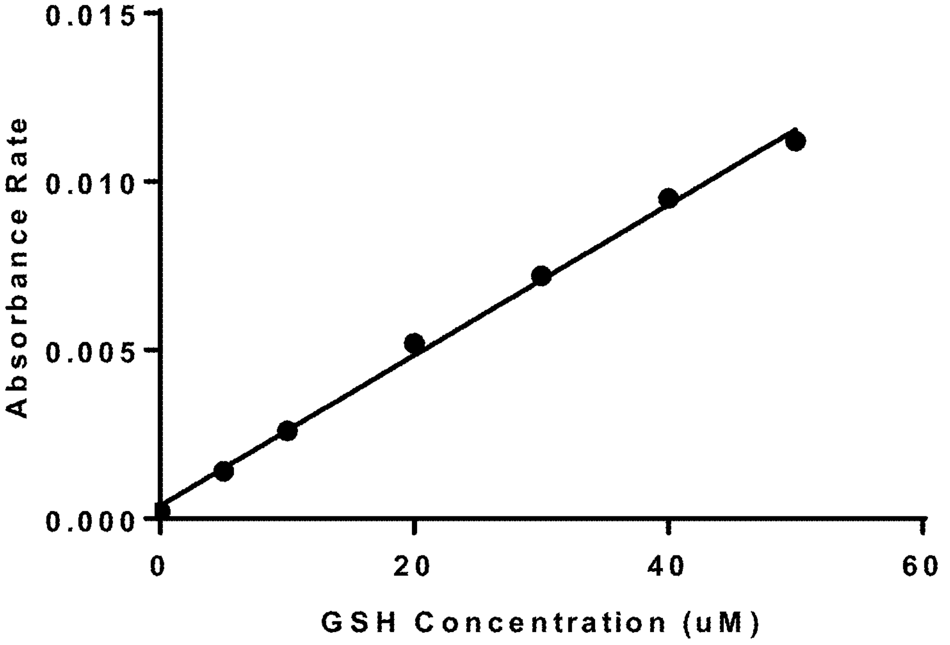
Figure 28:
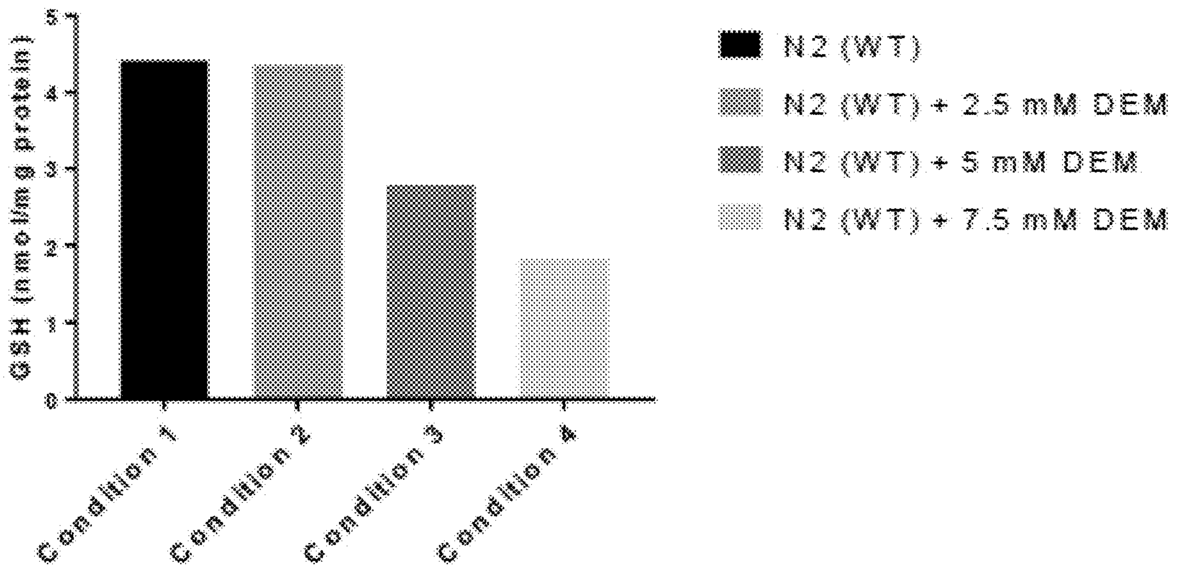
FIG. 28. Effect of the GSH Depleting agent, Diethyl Maleate (DEM). Worms were treated with DEM for 24 hours. GSH levels in N2 treated with DEM were dose-dependently reduced.
Figure 29:
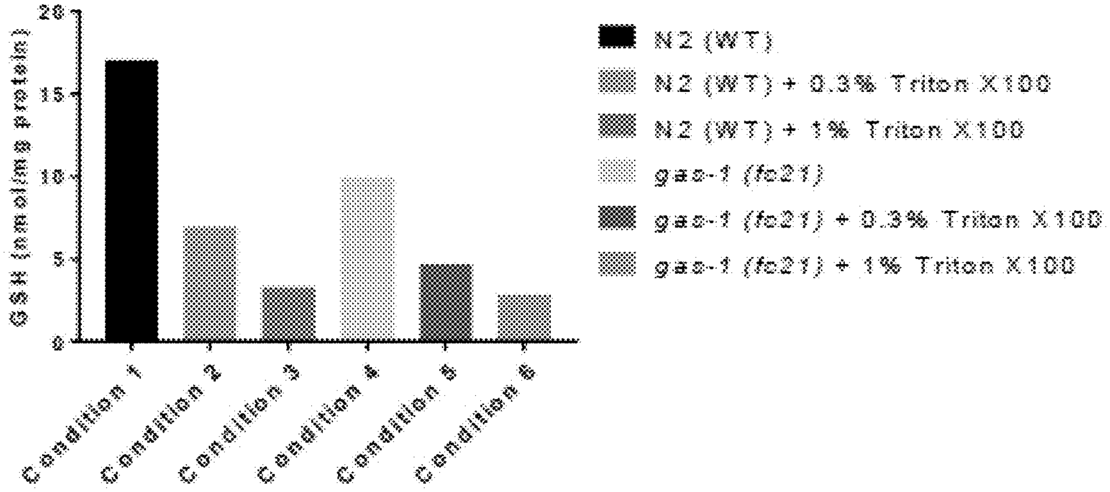
FIG. 29. Detergent Effect on Extraction Efficiency. GSH extraction efficiency with Triton X100 was decreased in dose-dependent fashion.
Figure 30:
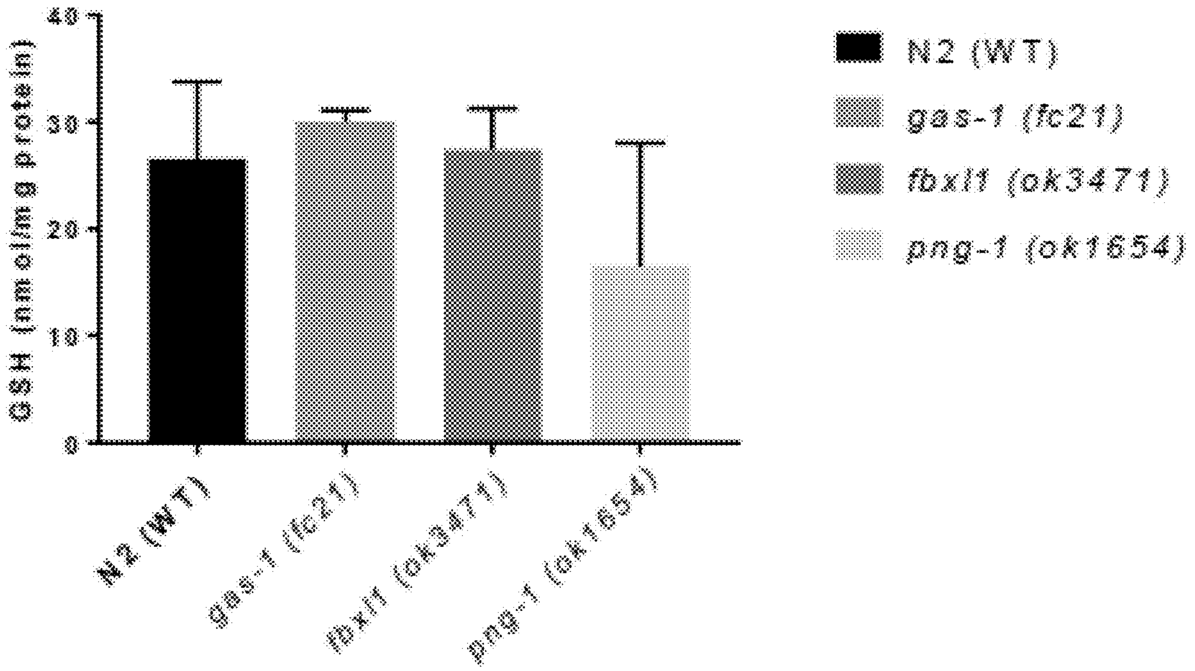
FIG. 30. GSH content in various mitochondrial disease mutant worms. GSH levels were quantified by the HPLC-ECD method. Approximately, 5000 worms were used per extraction and the data shown is from three biological replicates. Error bars indicate SEM FIGS. 31A-31C. Assay Development of GSSG Measurement from *C. elegans* Lysate. We assessed efficacy of N-ethylmaleimide (NEM) treatment to remove free GSH (A, right), the reducing capacity of sodium borohydride (NaBH4) B, left), and the effect of chloroform extraction to remove excess NEM from an MPA-deproteinized sample (B, right). (A) Treatment with the sulfhydryl alkylating agent NEM followed by metaphosphoric acid (MPA) deproteinization completely removes the GSH peak from N2 (WT) worm lysate. (B, left) The strong reducing agent NaBH4 reduces GSSG back to GSH, with the majority of generated GSH (from GSSG) reacted again with NEM in the sample to increase the GSH-NEM peak. (B, right) Chloroform extraction removes the remaining NEM and GSH-NEM from NEM-treated worm samples.
Figure 31A:
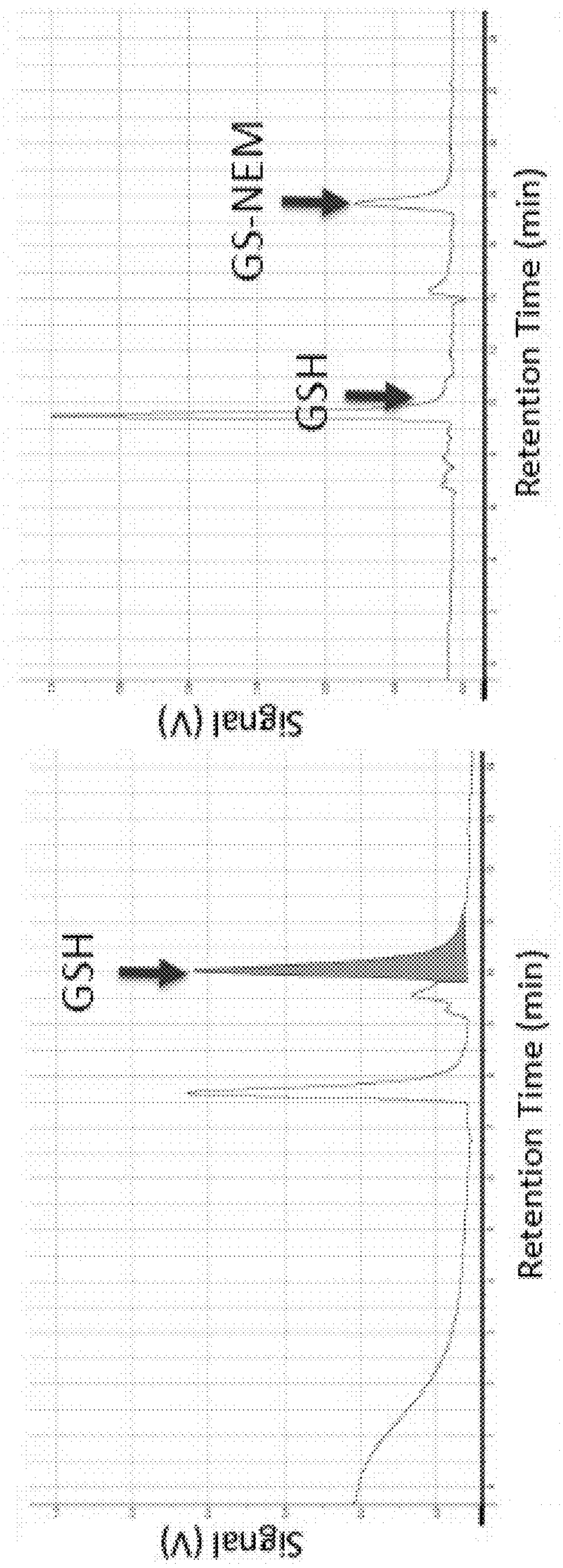
FIG. 31C Assay Development of GSSG Measurement from *C. elegans* Lysate by using phosphine derivatives, Tris(3-hydroxypropyl)phosphine (THPP) or Tris(2-carboxyethyl)phosphine (TCEP). We compared the reducing effect of air stable reducing agents, THPP and TCEP, which allow for the rapid and irreversible reductive cleavage of disulfide bonds in buffered aqueous-organic media. Chloroform extraction step to remove the excess NEM was omitted in this experiment. Both THPP and TCEP efficiently reduced GSSG, and the ratio of GSH to GSSG are within the range of reported values obtained by other methods.
Figure 31B:
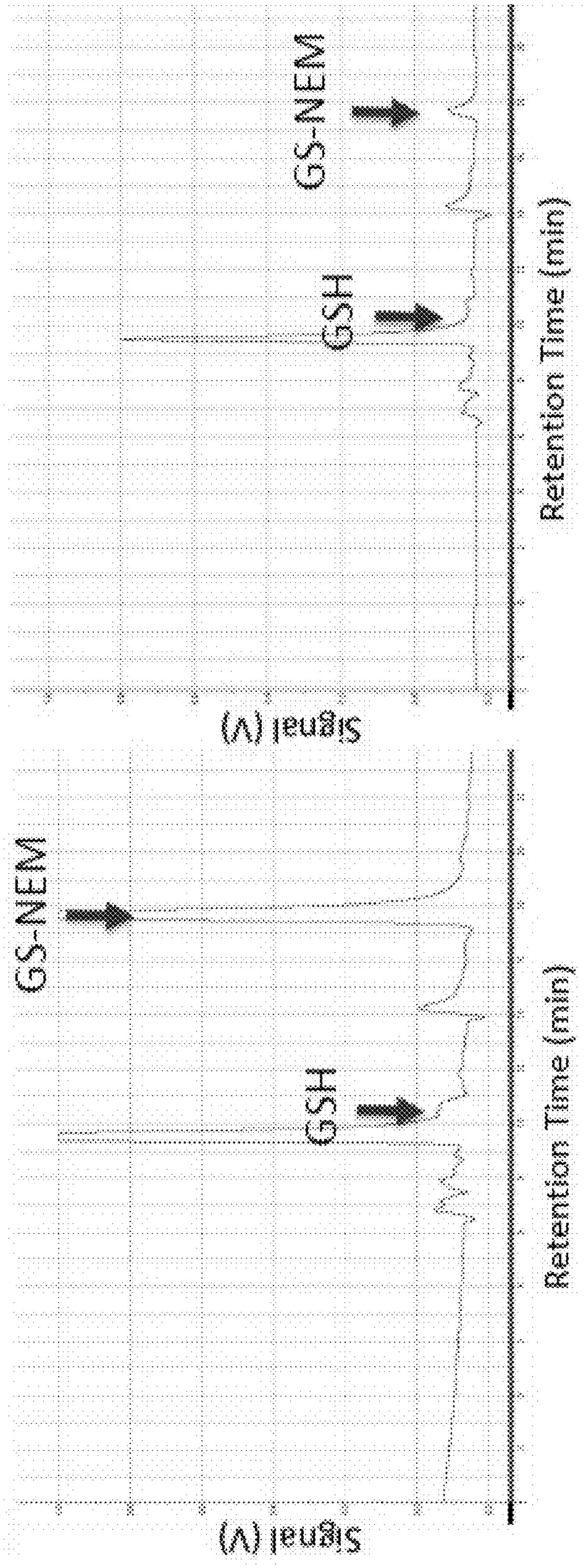
Figure 31C:
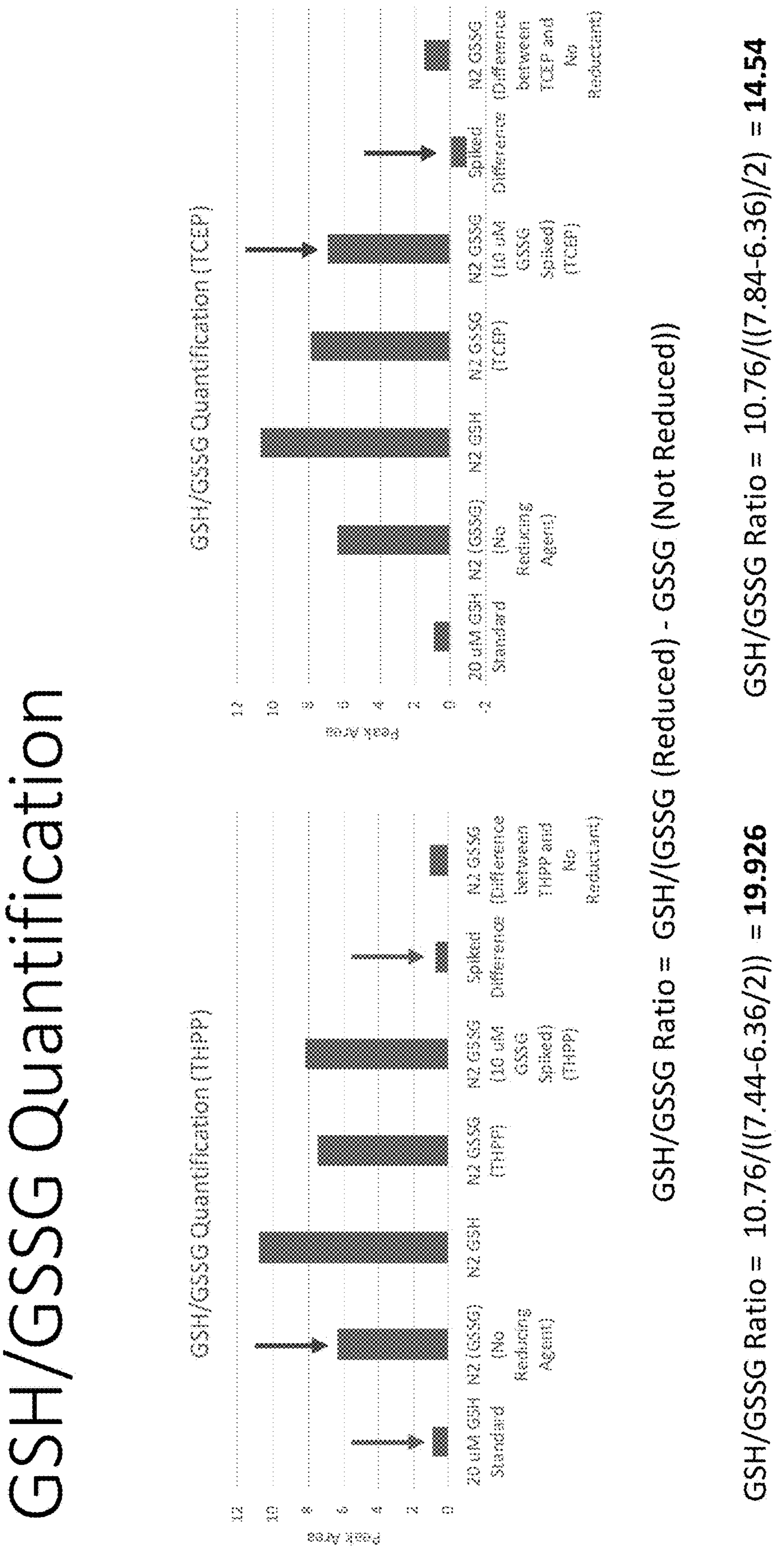

SURF1del2$^{-/-}$ zebrafish have reduced swimming activity at baseline and with light/dark stress. Behavioral activity of SURF1-del2$^{-/-}$ zebrafish at 7 dpf (Zebrabox, Viewpoint) was quantified in darkness for 30 minutes (FIG. 25A), and following 10 minutes of strobe light stress after which animals were allowed to recover in darkness for 20 minutes (FIG. 25B). SURF1-del2$^{-/-}$ zebrafish (red) displayed lower basal and post-stress activity and endurance relative to wild-type (AB) control zebrafish.

Conclusion

We have generated 2 novel SURF1−/− zebrafish CRISPR/Cas9 lines, which recapitulate key aspects of human SURF1 disease, including complex IV deficiency, acute stress sensitivity (stroke, impaired neuromuscular response), and reduced activity and endurance. Antioxidants (NAC or cysteamine bitartrate) provide resiliency in SURF1−/− animals, preventing decompensation from acute low-dose CIV inhibition

EXAMPLE V

Glutathione Quantification Assay for *Caenorhabditis elegans* Models of Mitochondrial Disease Mitochondrial disease is a broad term describing various disorders with impaired mitochondrial ETC function. Reactive oxygen species (ROS) are highly unstable oxygen-containing free radicals, high levels of which may cause significant damage to cellular components. Increased ROS levels are a main hallmark of mitochondrial disease. Cells combat oxidative stress using glutathione, the most abundant antioxidant in eukaryotes. As in the previous examples, *Caenorhabditis elegans* has been utilized to model in vivo effects of mitochondrial disease.

GSH levels are an important parameter to evaluate the physiological effects of mitochondrial disease. In the present example, the development and optimization of an HPLC-ECD assay to sensitively quantify reduced (GSH) and oxidized (GSSG) glutathione levels in *C. elegans* is described. We have optimized each of the following: mobile phase buffer composition, homogenization conditions, deproteinizing conditions and reducing agents. The differences between HPLC-ECD and conventional enzymatic assays are set forth in Table II below.

TABLE II

| HPLC-ECD ASSAY | ENZYMATIC ASSAY |
|---|---|
| High Sensitivity (~50 fM) | Moderate to low sensitivity (~5 μM) |
| Small sample amounts allows for multiple analyses | Large sample amounts required |
| Multiple sample analytes can be studied simultaneously | Measures total glutathione only |

The mobile phase buffer composition determines retention time and separation of GSH on chromatogram. Our preferred buffer for this purpose is 99% 0.1 M sodium phosphate buffer (pH 2.5), 1% MeOH and 75 mg/L sodium octanesulfonate (SOS), 5 mg/L EDTA. Very few homogenization buffers are compatible with NaBH4 reduction. We tested *S. basal*, NaP, KP, HEPES, MOPS, and Tris-HCl. While Tris-HCl was the most effective, we were still unable to obtain 100% recovery of GSH. Notably, homogenization should be performed ~pH 7 as the NEM reaction does not proceed well at low pH. Currently, homogenization in $H_2O$ appears to work best.

We have also optimized the deproteinizing conditions employed. Metaphosphoric acid (MPA) is very acidic and thus it was unsuitable for use with NaBH4; likely also unusable with THPP/TCEP. We also observed that Perchloric acid (PCA) was also too acidic. In preferred approaches, methanol (MeOH) was used as no pH change occurred after deproteinization and it was also usable with THPP/TCEP. Because MeOH was less effective overall in removing protein, a spin column was employed to remove leftover protein/lipids which also trapped GSSG.

A number of reducing agents were tested to identify the most effective agent. Use NaBH4 results in side product formation; recovery of GSH requires ~1 hour incubation at 37° C. and did not work well with biological sample. Tris(2-carboxyethyl)phosphine (TCEP) also results in side product formation, although it is effective at low pH reduces side products formation. Tris(3-hydroxypropyl)phosphine (THPP) provides for high yield of GSH and very low side product formation and thus is preferred.

The custom HPLC-ECD assay described in FIGS. 26 to 31 effectively measures GSH levels, with 100 times higher sensitivity compared to the standard enzymatic assay.

demonstrating linearity over five digits. Detergent decreases the extraction efficiency of GSH from *C. elegans*. NEM effectively sequesters free GSH, with subsequent reduction of GSSG to GSH with $NaBH_4$ to allow for HPLC-ECD specific quantification of GSSG. This assay can also be used to advantage to screen drugs that normalize glutathione levels in mitochondrial disease models.

EXAMPLE VI

"Mitochondrial Cocktail" Combinatorial Compound Screening in *C. elegans* and Zebrafish Models of Mitochondrial Complex I Disease and Identification of Combinations Having Efficacy for the Treatment of Mitochondrial Disorders In order to develop effective combinatorial cocktails for the treatment of mitochondrial disorders we have chosen to target metabolic modifiers, signaling modifiers and antioxidants.

The following materials and methods are provided to facilitate the practice of Example VI.

Relative Quantitation of Mitochondrial Matrix Superoxide Burden, Mitochondrial Membrane Potential, and Mitochondria Content by Fluorescence Microscopy in Young Adult *C. elegans*

Mitochondrial oxidant burden (MitoSOX Red), membrane potential (tetramethylrhodamine ethyl ester, TMRE), and mitochondrial content (MitoTracker Green FM, MTG) were performed at 20° C. using in vivo terminal pharyngeal bulb relative fluorescence microscopic quantitation, as previously described. Briefly, synchronous populations of Day 0 young adults were moved to 35 mm NGM plates spread with OP50 *E. coli*, a desired drug treatment 2.5 mM N-acetylcysteine, Nicotinic acid, glucose and the duplicate or triplicates combination of these drugs or buffer control (S-basal/water for all other drugs) was performed on NGM plates. Simultaneously with the drug treatments, worms were treated with either 10 μM MitoSOX Red (matrix oxidant burden), 100 nM TMRE (mitochondrial membrane potential), or 2 μM MitoTracker Green FM (mitochondria content) for 24 h. The next day, worms were transferred with a pick onto 35 mm agar plates spread with OP50 *E. coli* without dye for 1 h to allow clearing of residual dye from the gut. Worms were then paralyzed in situ with 5 mg/ml levamisole. Photographs were taken in a darkened room at 160× magnification with a Cool Snap cf2 camera (Nikon, Melville, NY). A CY3 fluorescence cube set (MZFLIII, Leica, Bannockburn, IL) was used for MitoSOX and TMRE. A GFP2 filter set (Leica) was used for MitoTracker Green FM. Respective exposure times were 2 s, 320 ms, and 300 ms for each of MitoSOX, TMRE, and MitoTracker Green FM. The resulting images were background subtracted, and the nematode terminal pharyngeal bulb was manually circled to obtain mean intensity of the region by using Fiji Is Just ImageJ. Fluorescence data for each strain were normalized to its same day control to account for day-to-day variation. A minimum of 3 independent experiments of approximately 50 animals per replicate were studied per strain per dye. The significance of the difference in the mean fluorescence intensity between strains under different experimental conditions was assessed by mixed-effect ANOVA, which assesses potential batch effect due to samples being experimentally prepared, processed, and analyzed on different days by including a batch random effect in the model. A statistical significance threshold was set at $P<0.05$. All statistical analyses were performed in SAS 9.3.

Whole Worm Amino Acid Profiling and Stable-Isotopic Intermediary Metabolic Flux Analysis in *C. elegans*

Whole worm free-amino acid profiling and metabolic flux analysis were performed. Briefly, synchronous populations of 1000-1500 worms were grown to adulthood on NGM plates. 10 mM universally labeled $^{13}C$-glucose and appropriate drug in desired concentration were added to plates before first day adult worms were transferred to fresh plates. The same drug treatments at the same concentrations were used as described above in the microarray and RNA-Seq method sections. Following 24 h of incubation with drug, adult worms were washed clear of bacteria 5 times with *S. basal*. Worm number was estimated by counting. Three biological triplicate experiments were performed per condition. Metabolic reactions were stopped by the addition of 4% perchloric acid (PCA) containing 20 nmol internal standard (e-aminocaproic acid, 16.7 μM). Samples were ground using a plastic homogenizer and motorized drill until visual inspection confirmed worm disruption. Precipitated protein was removed, re-dissolved in 1 normal NaOH, and protein concentration was determined by DC Protein Assay (Bio-Rad). 50 μl neutralized samples were separated for HPLC analysis. From the remaining neutralized samples, amino acids and organic acids were extracted using ion exchange resin (Bio-Rad) in AG50 and AG1 columns, respectively, to measure relative enrichment in amino acids and organic acids by mass spectrometry, as previously described. MS analyses were performed in the Metabolomics Core Facility at The Children's Hospital of Philadelphia. Stable isotopic enrichment was calculated in Excel (Microsoft) for each species as previously described [ref], according to the following formula: Atoms Percent Excess, corrected (APE)=(Rsa−Rst)*100/[(Rsa−Rst)+100], where Rsa−Ratio of the sample and Rst−Ratio of the standard. Statistical comparison between groups was performed using random-effects ANOVA (JMP version 10, SAS Institute, Cary NC). 2.6.

Transcriptome Profiling of Drug Treatment Effect by RNAseq Analysis

Sample preparation for gene expression profiling by RNAseq technique was performed. Briefly, wild-type (N2 Bristol) and mitochondrial RC Complex I deficient gas-1 (fc21) animals were maintained at 20° C. by established protocols. Synchronous young adult populations of approximately 1,000-2,000 nematodes were obtained and treated on the first day of egg laying for 24 hours on NGM plates spread with the same drugs as described in the lifespan methods section and buffer control, per established protocols. After drug treatment, total RNA was isolated and prepared for transcriptome profiling.

Briefly, total RNA was isolated using the Trizol method and RNA concentration was measured using the NanoDrop-1000. RNA quality was determined by using Agilent Bioanalyzer in the NapCore Facility at The Children's Hospital of Philadelphia Research Institute, where RIN number between 8 and 10 as required for further sample analysis. Library preparation was performed using the Illumina Truseq Stranded Total RNA Sample Preparation Kit (San Diego, CA), with indexing to enable 8 samples to be run per lane. Samples were submitted to the BGI at CHOP Sequencing Core Facility at The Children's Hospital of Philadelphia Research Institute CHOP for next generation sequencing (RNAseq) analysis on Illumina HiSeq 2000 instruments. Samples were run in High Throughput Mode of 100 base pair paired end reads with 8 samples per lane to generate an estimated 20 million reads per sample. Library quality was assessed by Bio A analysis to check concentration, library size, and contamination, as we well as by gel analysis to assess degradation. Quantitative PCR was then performed to determine optimal sample concentrations using the Applied Biosystems Step One Plus Real Time PCR machine to enable proper sample pooling. Sequencing reads saved in FASTQ files were aligned to obtain gene-level expression data for bioinformatic analysis. Data quality issues, such as total throughput, confounding factors, and outlier samples, were fully evaluated to ensure validity of analysis results. Gene and KEGG Pathway-level analyses were also performed.

Results

Figure 32A:
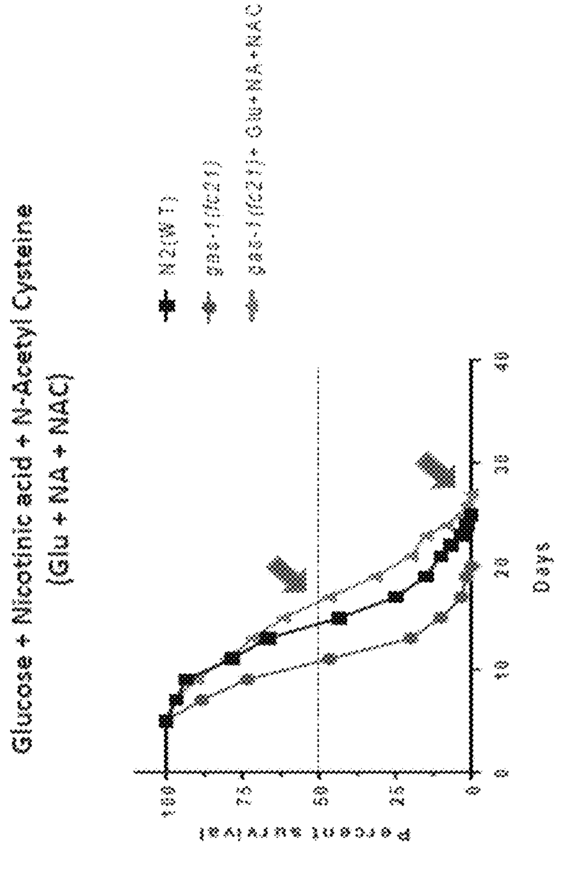
FIGS. 32A-32B. Shows representative lifespan curves for the combinations that showed significant improvements ($p<0.0001$) in lifespan.
Figure 32B:
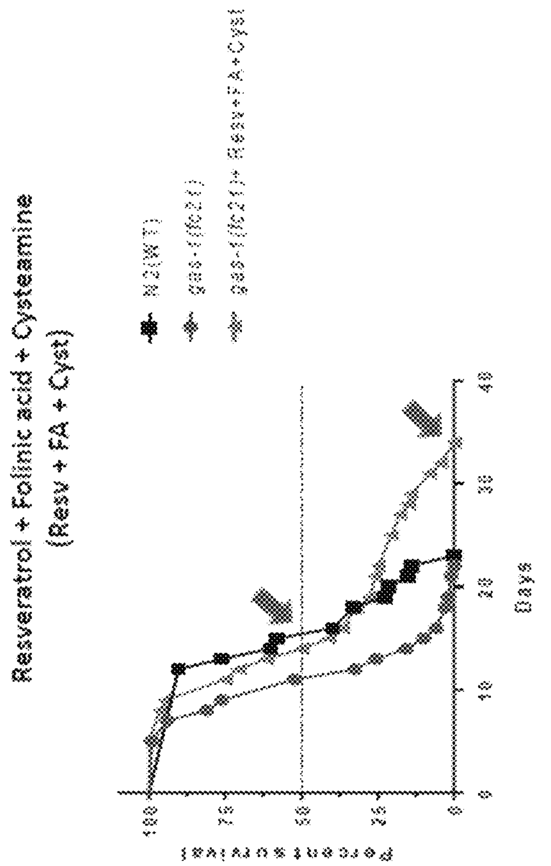
Figure 32C:
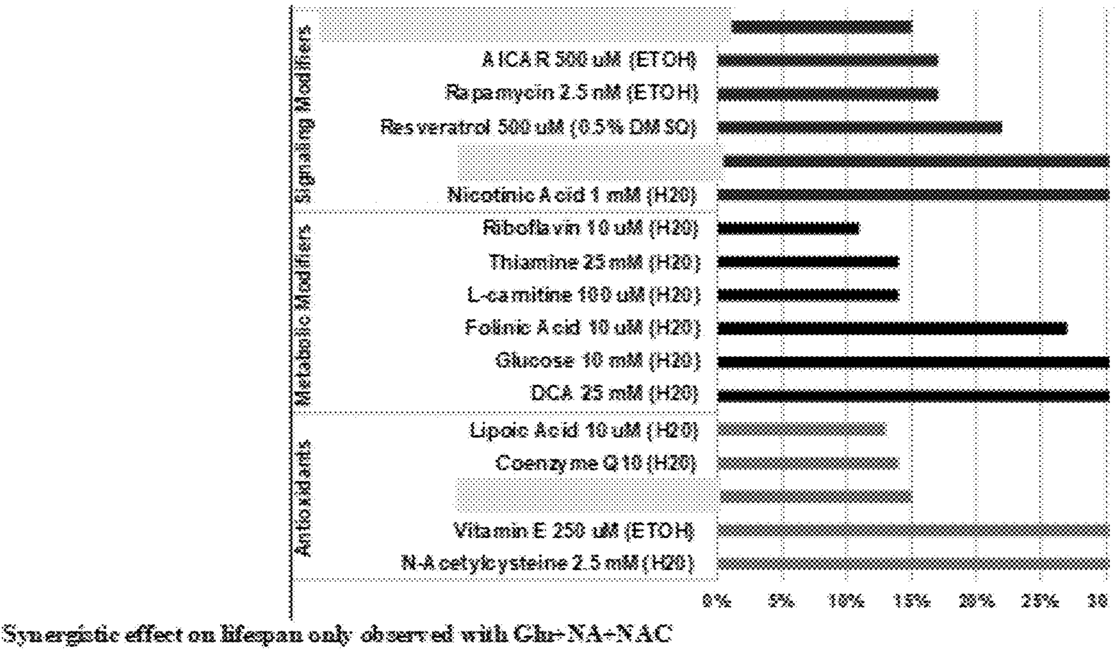
FIG. 32C shows synergistic effects of different agents disclosed herein.

Identification of Mitochondrial Cocktails from Lifespan Analyses that Significantly Improved the Short Lifespan gas-1(fc21) NDUFS2 Mutant Worms The gas-1(fc21) *C. elegans* which has been extensively studied shows various biochemical, physiological and phenotypic alterations as compared to wild type N2 worms. One of the key alterations that is observed in these worms is the significant reduction in lifespan. Previous studies carried out in our lab demonstrated that the lifespan of the gas-1 (fc21) animals could be improved with supplementation with certain pharmacological agents as described in the previous examples. Although, supplementation of individual drugs showed improvements we wanted to assess the effects of these drugs when they are administered as combinations. To this end we tested different combination drug cocktails (See FIG. 32C). Initial lifespan screening led to the identification of two cocktail combinations which showed significant increase (p in the lifespan of short lived gas-1(fc21) (FIG. 32) which included the cocktails Glu+A+NAC (55%; FIG. 32A) and Resv+FA+Cyst (33%; FIG. 32B). Moreover, the Glucose NA NAC cocktail showed a lifespan increase even more than wild type N2 lifespans worm (p=0.011). See FIG. 32C.

Figure 33A:
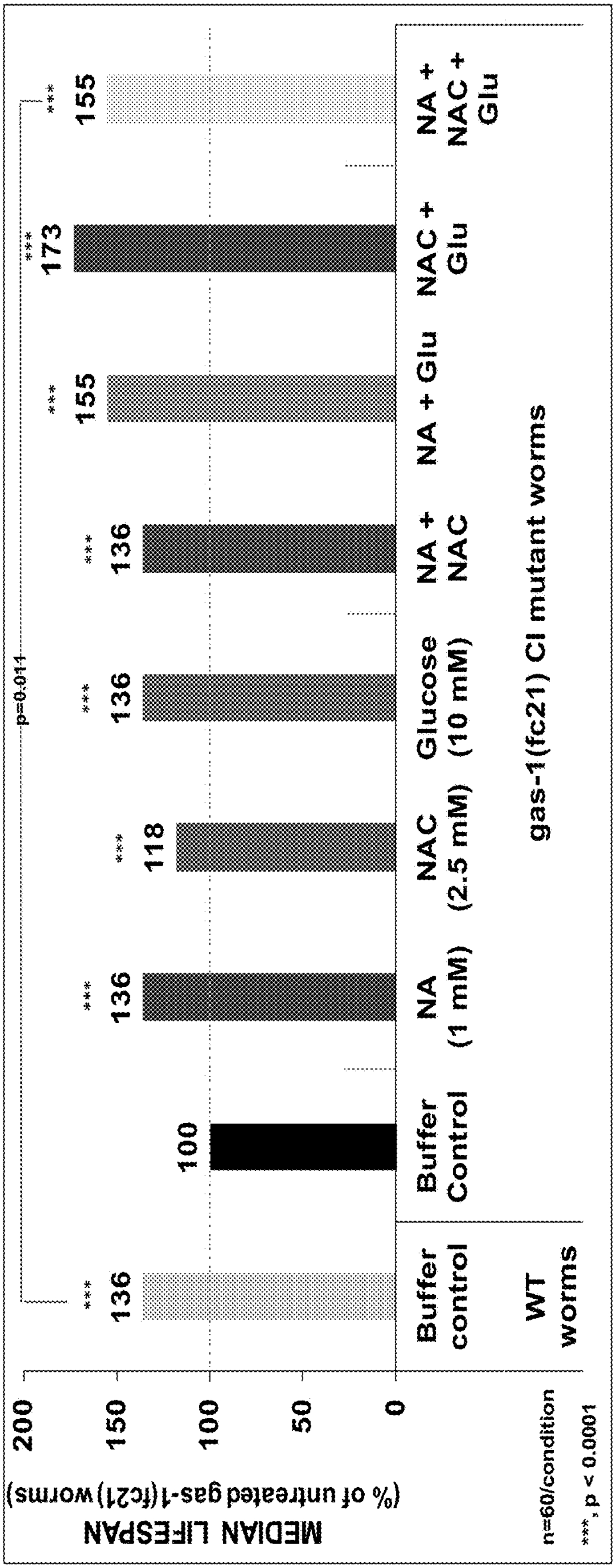
FIGS. 33A-33B. Combined therapy has synergistic rescue effect on CI deficient worm lifespan.
Figure 33B:
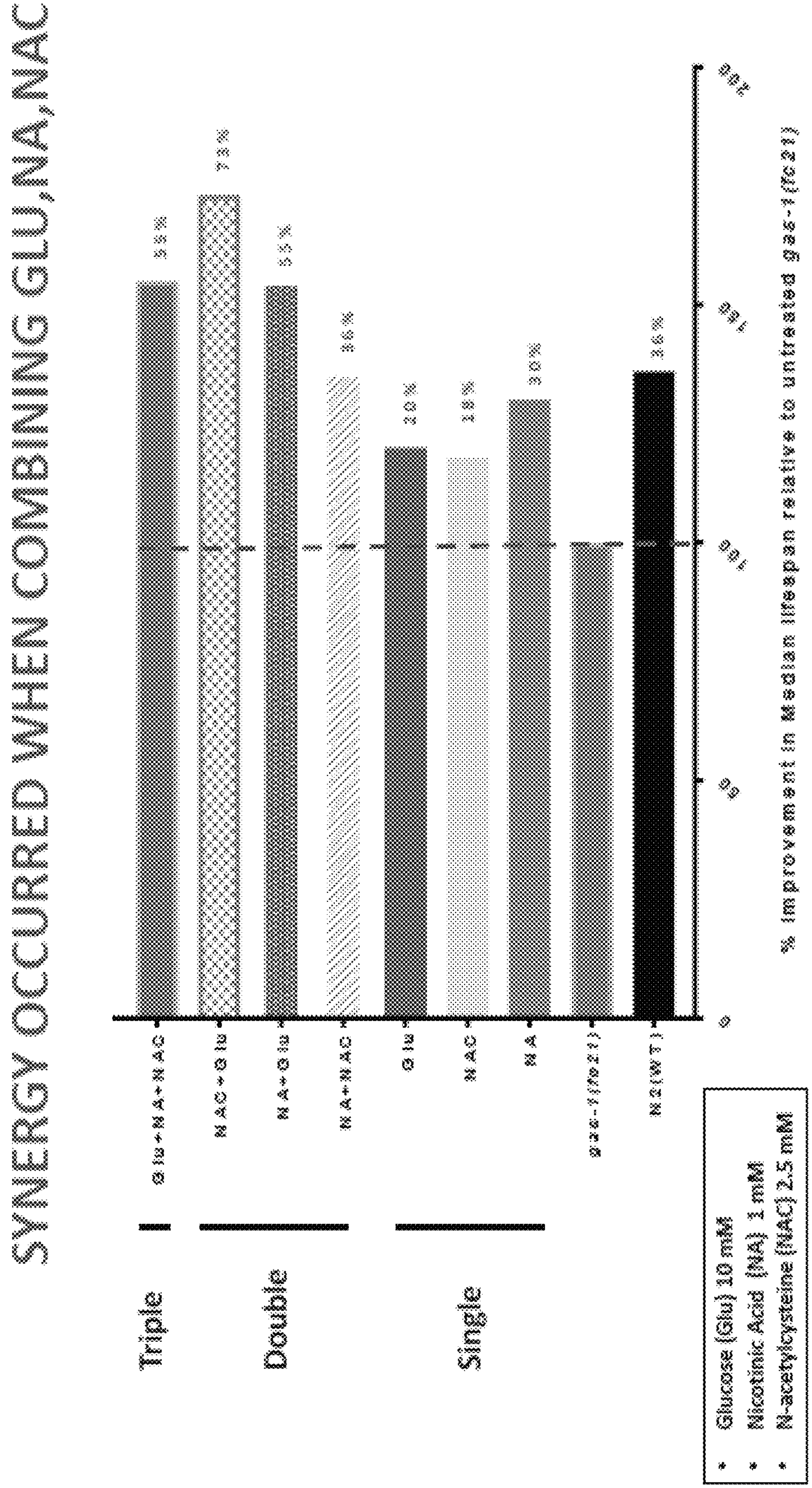

Previous studies carried in our lab has shown that compounds NAC, NA, Glucose and Resveratrol when administered at development (L1) can either partially or fully rescue the short lived lifespan of gas-1(fc21) animals to wild type N2 lifespan levels (FIG. 32A). Hence, we wanted to test if the extension in lifesp observed was due to synergetic effect of the combinations and not due to the action of individual components of the combinations. Hence, we further carried out lifespans with individual compounds and their pairwise duplicate combinations (FIG. 33 and FIG. 33B) or the triplicate combinations that showed improvements. Results of these assays showed that the glu+NA+NAC cocktail produced a synergetic effect observed as compared to the Resv+FA+Cyst where it was observed that the lifespan extension was driven by the action of Resveratrol only. Moreover, we also found that the duplicate combination Glu+NAC and Glu+NA not only showed synergy (FIG. 33B) and improved the lifespan as compared to the individual components (Glu, NA, NAC) but also had a lifespan extension more than wild type N2 worms.

Changes in Mitochondrial Physiology Observed as a Result of Administration of Cocktails Mitochondrial Complex I is the largest and one of the most important components of the RC, alterations in mitochondrial Complex I would lead to major disruptions in mitochondrial physiology. The alterations in mitochondrial physiology have been extensively studied due to Complex I dysfunction. Previous work has shown that gas-1(fc21) animals have a significantly reduced mitochondrial membrane potential and mitochondrial mass and high mitochondrial oxidant burden which can be altered by supplementation of pharmacological agents. Moreover we have already shown that NA significantly reduces the mitochondrial oxidant burden and NAC significantly increases the reduced membrane potential, but Glu increases membrane potential, mitochondrial mass and oxidant burden in gas-1(fc21) worms.

Figure 34:
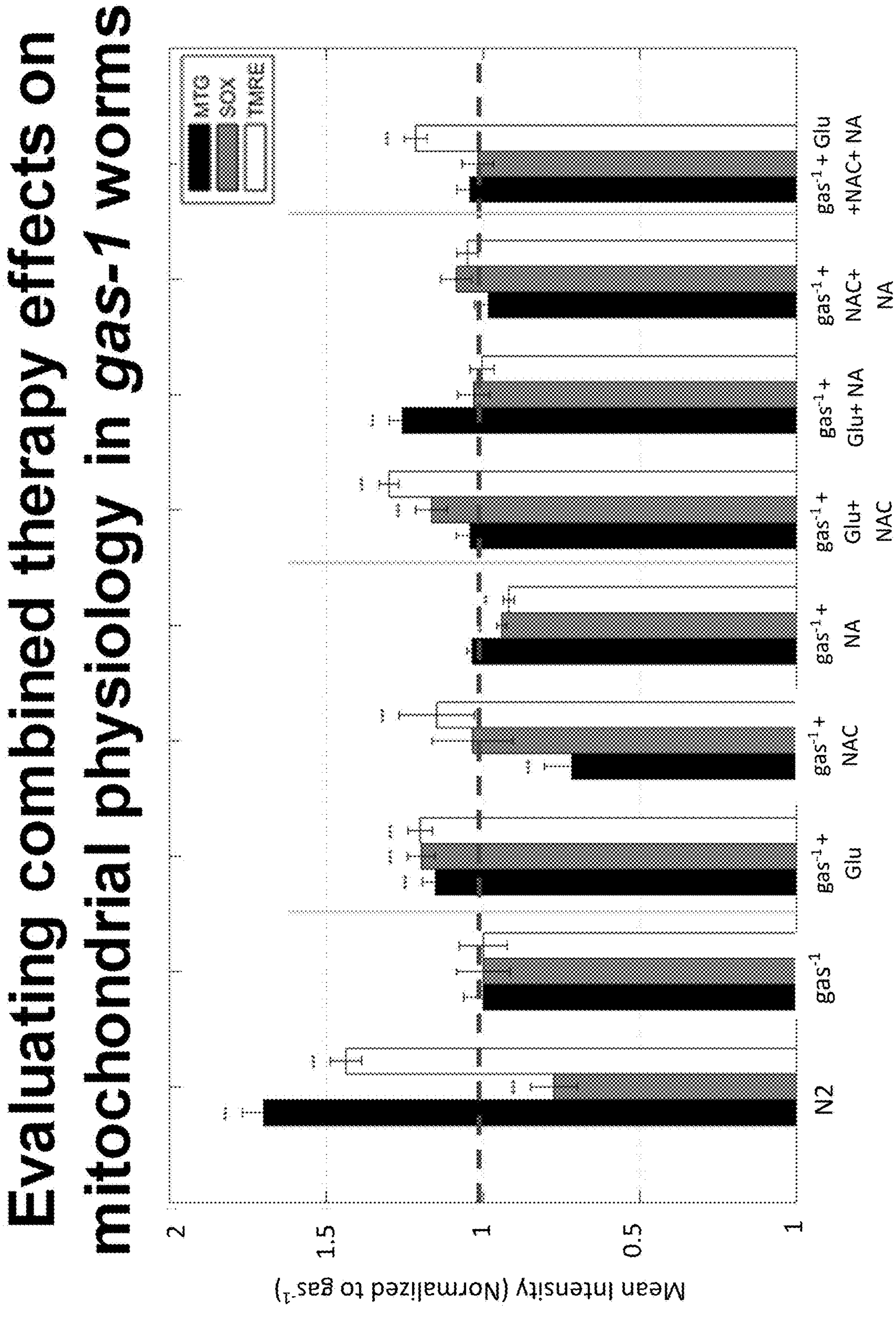
FIG. 34. A graph showing the results of analysis of combined therapy effects on mitochondrial physiology in as-1 worms.

Since synergy was observed along with significant improvements in the lifespan of the short lived gas-1(fc21) worms, we determined the effects of the same cocktails on the mitochondrial physiology. Glu+NA+NAC significantly improved membrane potential (21.5%), but did not rescue their reduced mitochondrial content or improve the mitochondrial oxidant burden 24 hour treatment in young adult. (FIG. 34) Similarly we evaluated the duplicate drugs pairs to evaluate their effect on the mitochondrial physiology. We found that Glu+NAC was the only combination that significantly improved membrane potential (30%) and was even synergistic when compared to the individual drugs the improvements seen by either glucose and NAC. Notably, the mitochondrial oxidant burden was significantly increased (16.5%) which was similar to what was observed with just glucose supplementation (19.7%). Moreover, we found that Glu+NA improved the mitochondrial mass (25%) (Mitotracker green) while insignificant changes were observed with supplementation of NA+NAC. Taken together we didn't observe a similar effect of the combinations on mitochondrial physiology as observed for survival where the gas-1(fc21) mutant's lifespans are completely restored to wildtype N2 levels.

Selective Changes in Metabolic Flux

Previous analysis carried out have indicated that primary models of mitochondrial dysfunction undergo a range of secondary metabolic alterations generating stable end products leading to cellular adaptations due to high level of metabolic requirements, which is similar to what is observed in human subjects. We have consistently shown that gas-1 (fc21) mutants exhibit both a modified TCA cycle and altered pyruvate metabolism and amino acid synthesis capability. Hence, we wanted to test if these combinations showing synergy would have an effect in restoring the altered metabolites in gas-1(fc21) mutants.

Significant Reduction in Alanine Levels Representative of Mitochondrial Complex I Dysfunction HPLC analysis of free amino acid concentrations revealed levels of amino acid Alanine (ALA) which has been reported previously to increase significantly in gas-1(fc21) worms were significantly reduced ($P<0.05$) and in some cases restored to wild type N2 levels with most of the combinations except NAC+NA. Subsequently, we also analyzed the levels of branched chain amino acids (Leucine, Isoleucine and Valine.

Gas chromatography/mass spectrometry (GC/MS) analysis of absolute isotopic enrichment in organic acids of gas-1(fc21) worms. treated with the combinations revealed that there was a reduction in the levels of Lactate, malate and citrate by all the treatments which increase significantly in these mutants as compared to the wild type N2 worms.

Global Pattern of Gene Expression Shows NAC+NA and NAC+Glu had the Best Reversing Effect We have previously determined that global transcriptome changes occur in gas-1(fc21) relative to wild-type N2 Bristol adult worms Many of the most up-regulated pathways likely reflect a coordinated attempt to reverse cellular energy deficiency that results from CI dysfunction, including pathways involved in oxidative phosphorylation itself, as well as fatty acid metabolism, 2-oxocarboxylic acid metabolism, alanine, aspartate, and glutamate metabolism, and pentose and glucuronate interconversions. Interestingly, while the "ribosome" pathway was significantly up-regulated, the "ribosomal biogenesis in eukaryotes" pathway was strongly down-regulated.

We assessed whether there were any changes reflected in the transcriptome profiles of the gas-1(fc21) worms treated with these combinations. The correlation of fold changes between the N2/untreated Gas-1 comparison and each Untreated/Treated comparison was calculated and the correlation coefficients were used to evaluate the effect of treatments to reverse changes caused in gas-1(fc21) mutants. Genes affected by Gas-1 mutation were selected from the N2/Untreated Gas-1 comparison, using cutoffs: fold change>=fch0 and false discovery rate<=fdr0. Respectively, 289 and 433 genes had higher and lower expression in untreated Gas-1 comparing to N2. The fold changes of these genes in response to drug treatments were then summarized. None of the treatments completely or mostly reversed the change in untreated Gas-1 from N2 wild type. Treatment of individual drugs had little impact. Relatively, the combined treatments of NAC+NA and NAC+Glu had the best reversing impact; especially on genes with decreased expression in Gas-1. The 2 combined treatments also caused similar changes as the genes reversed by NAC+NA and NAC+Glu were mostly common (FIG. 32A). The 198 genes with decreased expression in untreated Gas-1, were partially recovered by both NAC+NA and NAC+Glu treatments, suggesting the common pathways that might be utilized by these treatments to bring improvements.

Kegg Pathway Analysis

KEGG is a "computer representation" of the biological system. It integrates building blocks and wiring diagrams of the system—more specifically, genetic building blocks of genes and proteins, chemical building blocks of small molecules and reactions, and wiring diagrams of molecular interaction and reaction networks. This concept is realized in the different databases of KEGG, which are categorized into systems, genomic, chemical, and health information.

Figure 35:
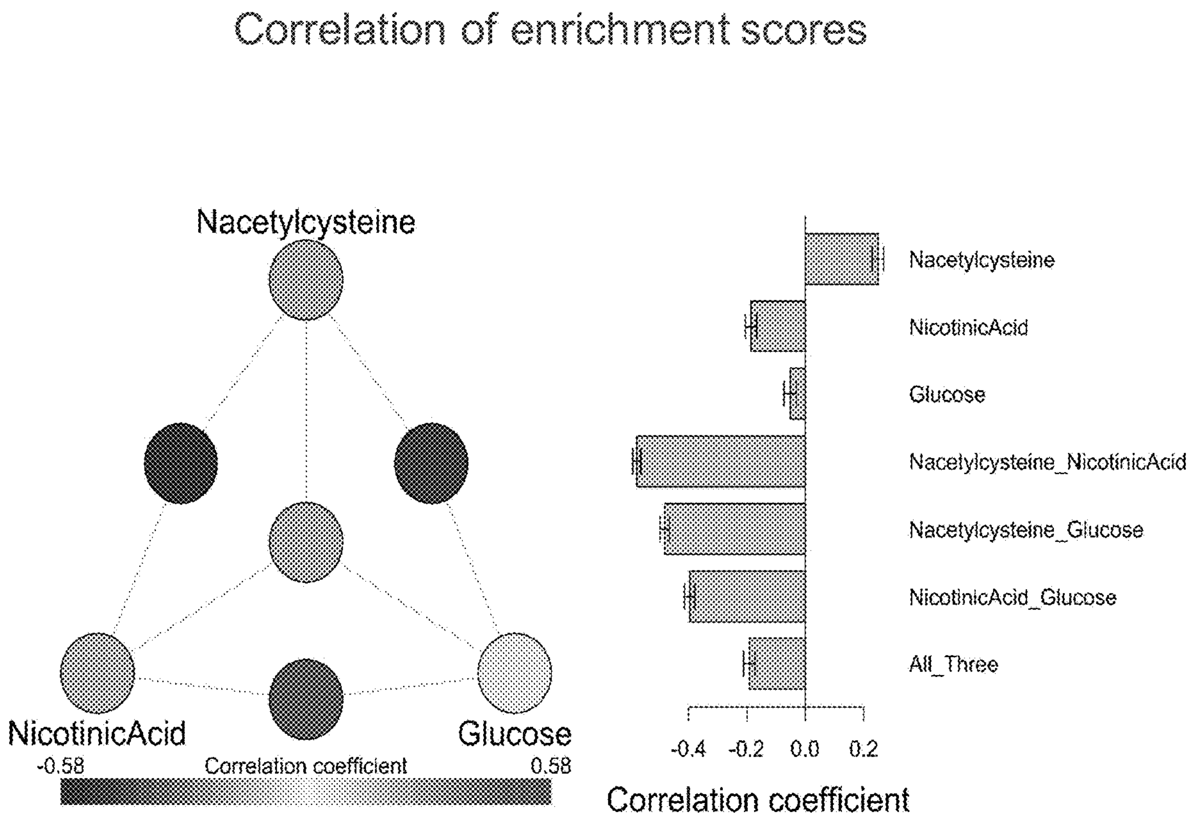
FIG. 35. Correlation of enrichment scores was calculated between N2/gas-1 untreated and all Untreated/Treated comparisons. The left panel shows the color-coded correlation coefficients and the right panel shows the bar plots. Overall, the two-drug combinations had negative correlations, suggesting their reversing effect at gene set level. 198 genes with decreased expression in untreated Gas-1, and partially recovered by both N-acetylcysteine+Nicotinic id and Nacetylcysteine+Glucose treatments.

Different genes were in enriched in a number of KEGG pathways from all 8 comparisons. See FIG. 35.

Zebrafish Assays

We have prepared and characterized diverse mitochondrial diseases using CRISPR/Cas9 knockout lines for inducing gross abnormalities and swimming behavior in a series of stress-response assays. This approach is valid. as human mitochondrial diseases often have stress-responsive metabolic dysfunction and functional phenotypes that are not readily apparent at baseline. We have assessed gross development, survival, organ-level morphology, heart rate, and integrated neurobehaviors of tap and touch response at baseline and in response to stressors of the series of established CRISPR/Cas9 knockout lines we have developed (NDUFS2, NUBPL, FBXL4, C12ORF65, SURF1, DLDH), as well as several targeted mutant lines being generated (NDUFS2 p.R290K; FBXL4 p.G356fs. p.Q597P; SURF1 p.R912W, NUBPL p.G56R; DLDH p.E375K). Animals are then screened in the zebrabox high-throughput behavioral analysis system both at baseline and after exposure to stressors including nutrient stress (over and underfeeding), cold and hot temperature stress, infection mimetics such as LPS, and additional mitochondrial inhibitor stresses (rotenone or azide or KCN). (2) Once a stressor is identified that reliably impairs swimming behavior in each mitochondrial disease mutant larvae model, we will use this stressor-model to test a multi; drug panel, and optimal combinations, as were previously identified in *C. elegans* as described above. Lead treatment effects in each zebrafish model can be validated by assessing mitochondrial physiology in diverse organs by confocal analysis and by fluorescence microscopy quantitation of Mitotracker Green/TMRE co-injected dyes co-injected into the early embryo yolk sac. Biochemical effects will be assessed by spectrophotometric assay of ETC activities, HPLC-ECD analysis of GSH and GSSG oxidative stress, and GC/MS based metabolomics analyses, as appropriate.

Figure 36A:
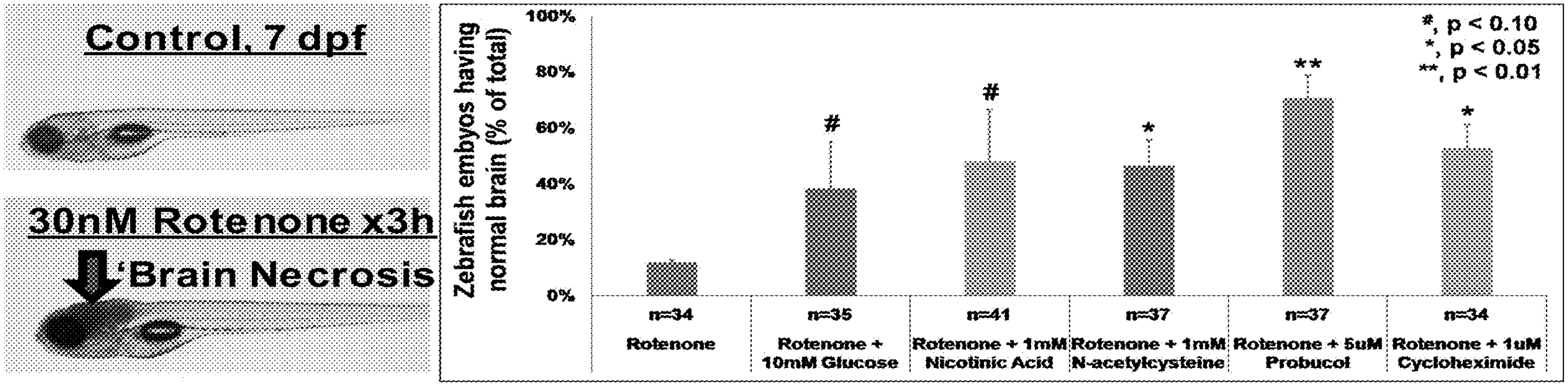
FIGS. 36A-36D. Zebrafish screening of therapeutic effects on individual organs FIG. 36A) protective effects of different combination of agents are shown.
Figure 36B:
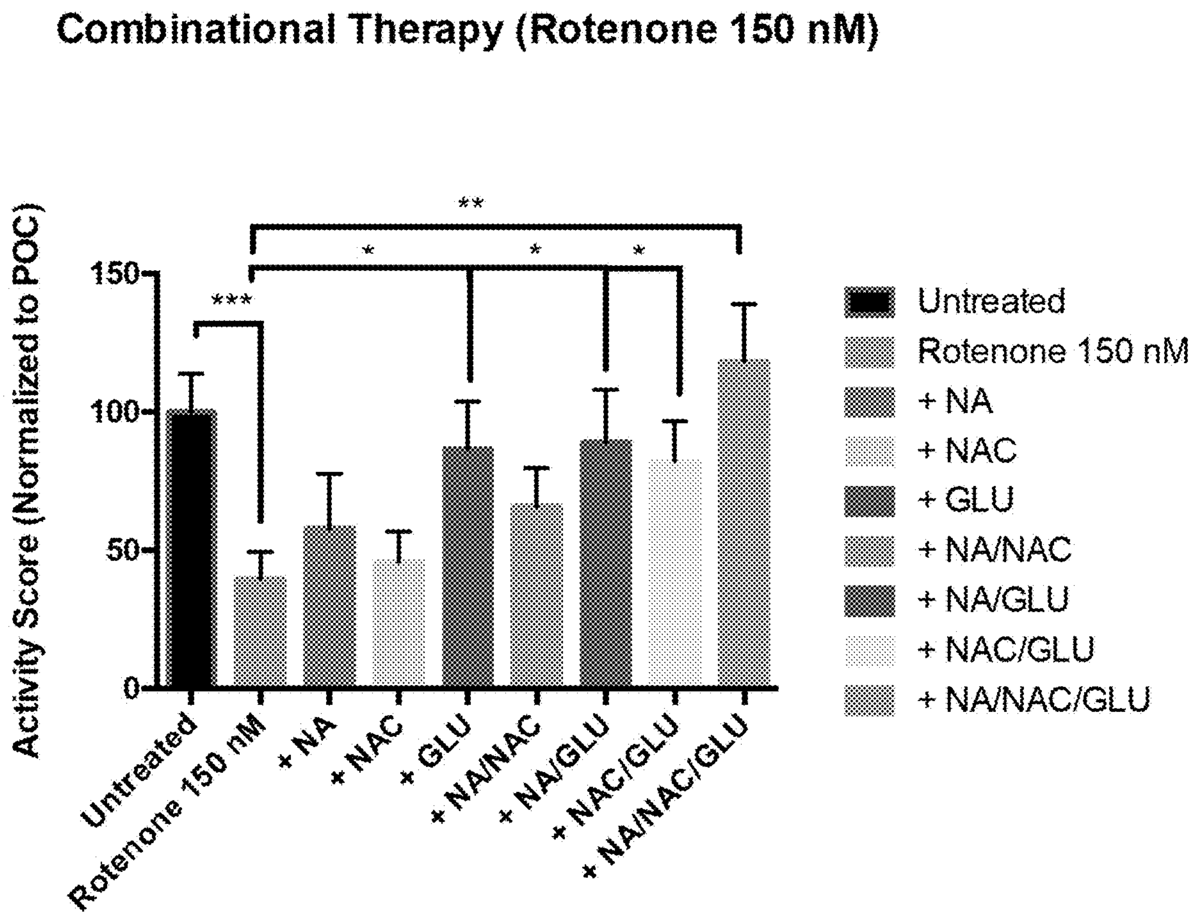
Figure 36C:
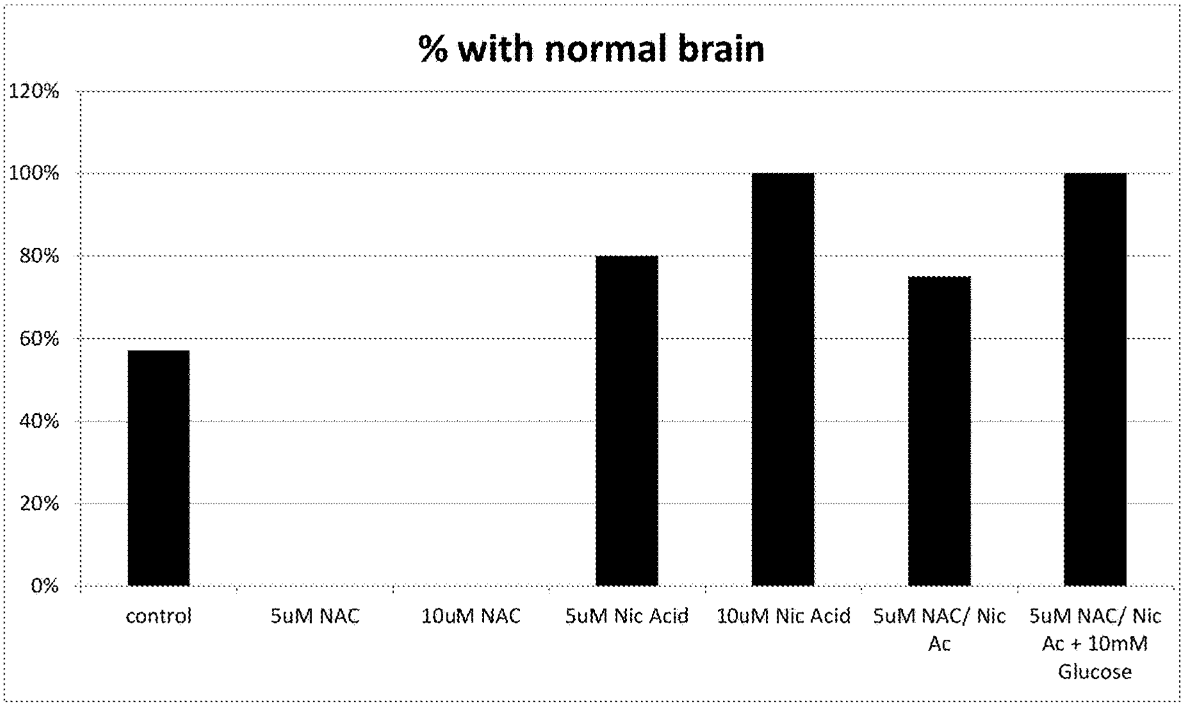
Figure 36D:
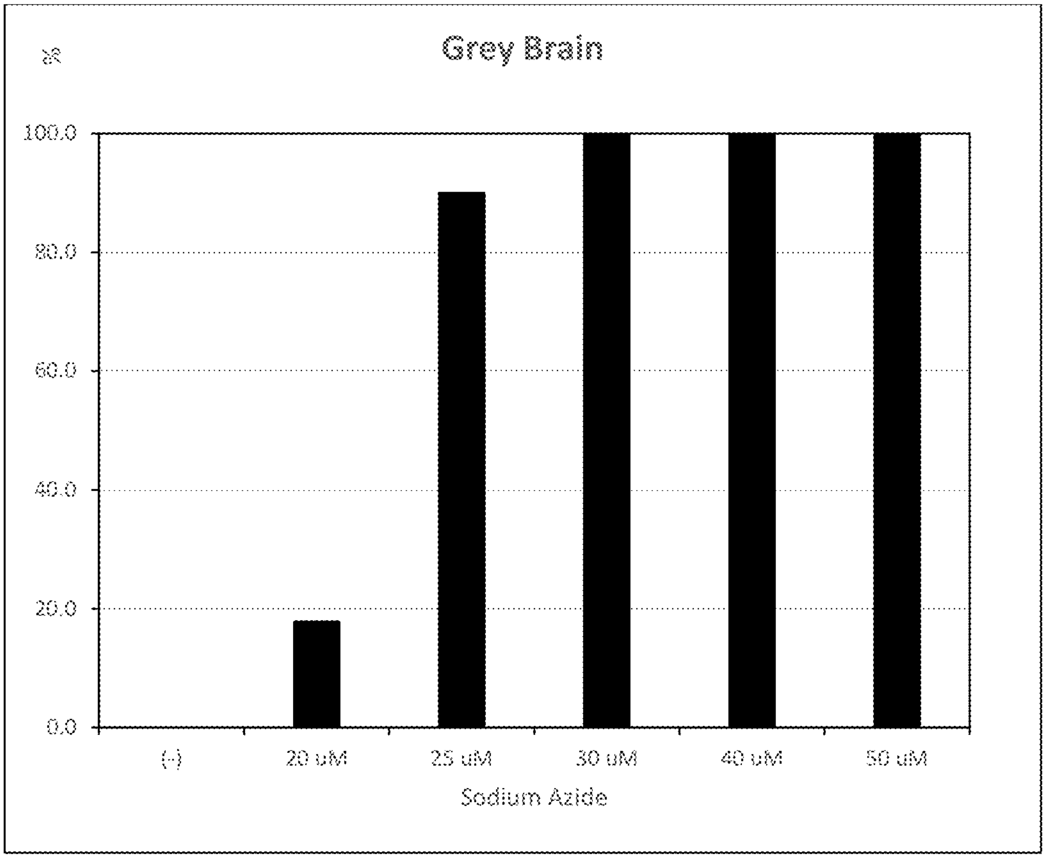
Figure 36E:
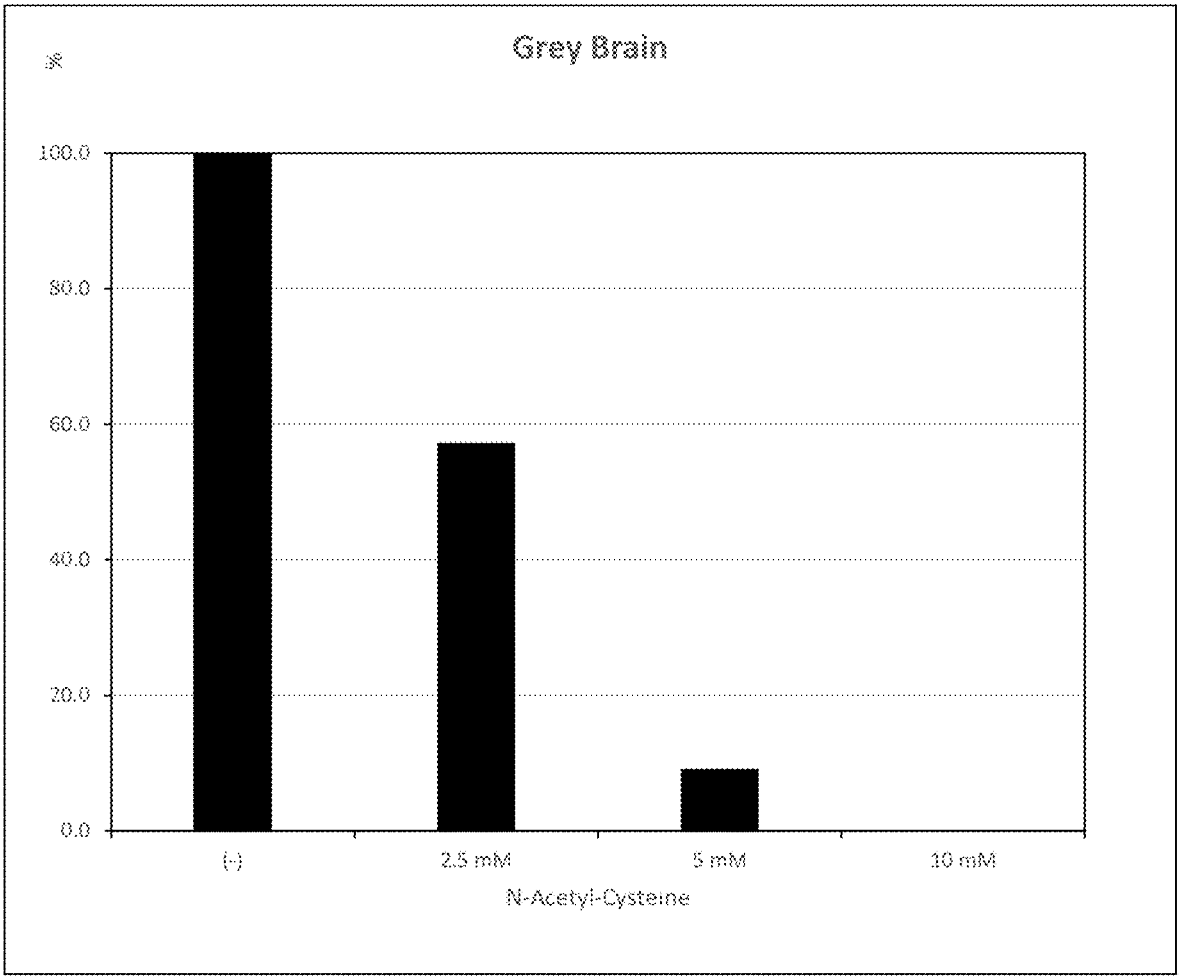

Using the Rotenone model which induces brain necrosis in zebrafish, we tested various drugs alone and in combination and identified protective combination that should have efficacy for the treatment of mitochondrial disorders. While Rotenone is exemplified in this example (FIGS. 36A and 36B), other specific RC stressors that exacerbate phenotypes in cell and animal models of mitochondrial RC disease could be employed. For example, as shown in FIGS. 36D and 36E, surf1 KO zebrafish were treated at 5 dpf with N-Acetyl Cysteine (NAC) at 1, 2, & 5 mM. At 6 dpf, the zebrafish were exposed to 25 mM Sodium Azide ($NaN_3$) or 8 mM Potassium Cyanide (KCN) (data not shown) and multiple phenotypes assessed after 18-24 hours on 7 dpf. The phenotypes assessed can include without limitation, swimming activity or swimming fatigue, organ structural impairment or dysfunction gray brain alterations in mitochondrial physiology (=brain death) (FIG. 36C), heart rate, startle (tap) response (stimulus on plate), and touch response (stimulus on animal).

Figure 37A:
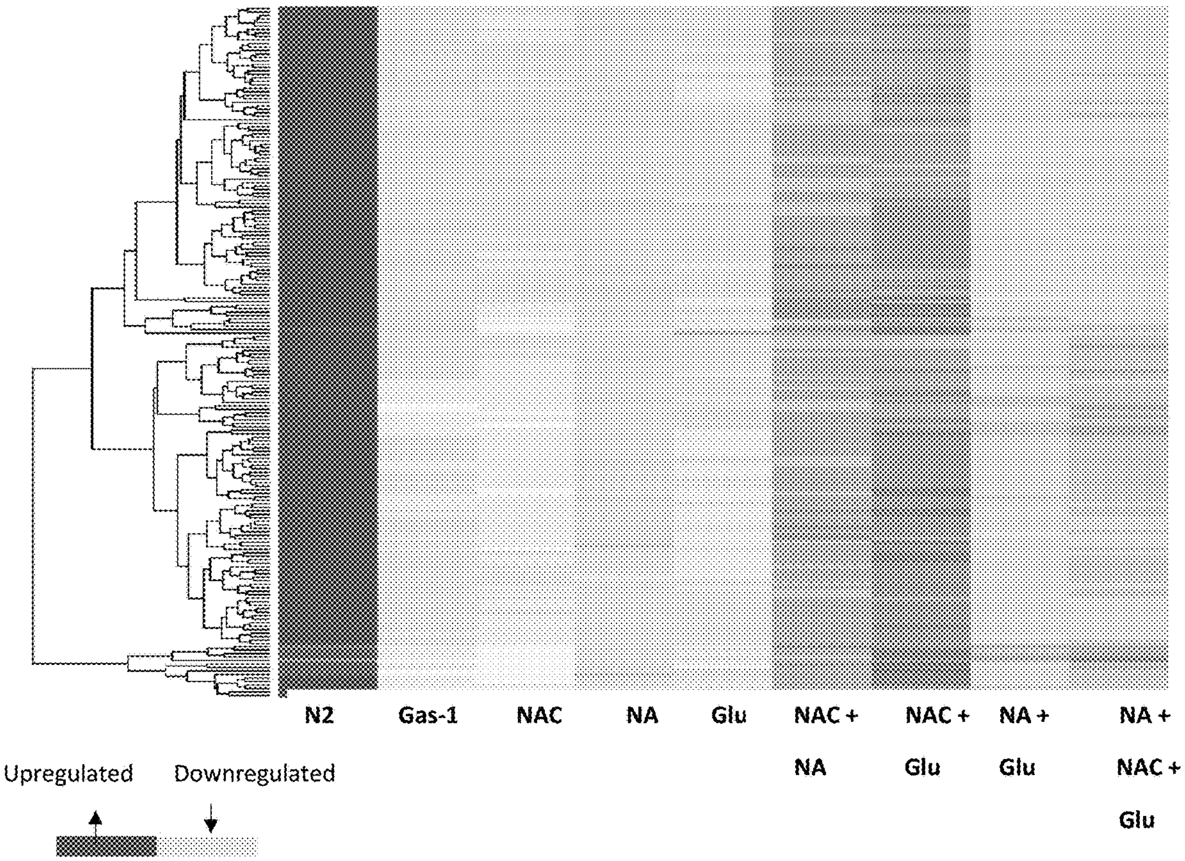
FIGS. 37A-37B. NAC+NA or NAC+Glu partially restored globally decreased gene expression and activity in ndusf2$^{-/-}$ model.
Figure 37B:
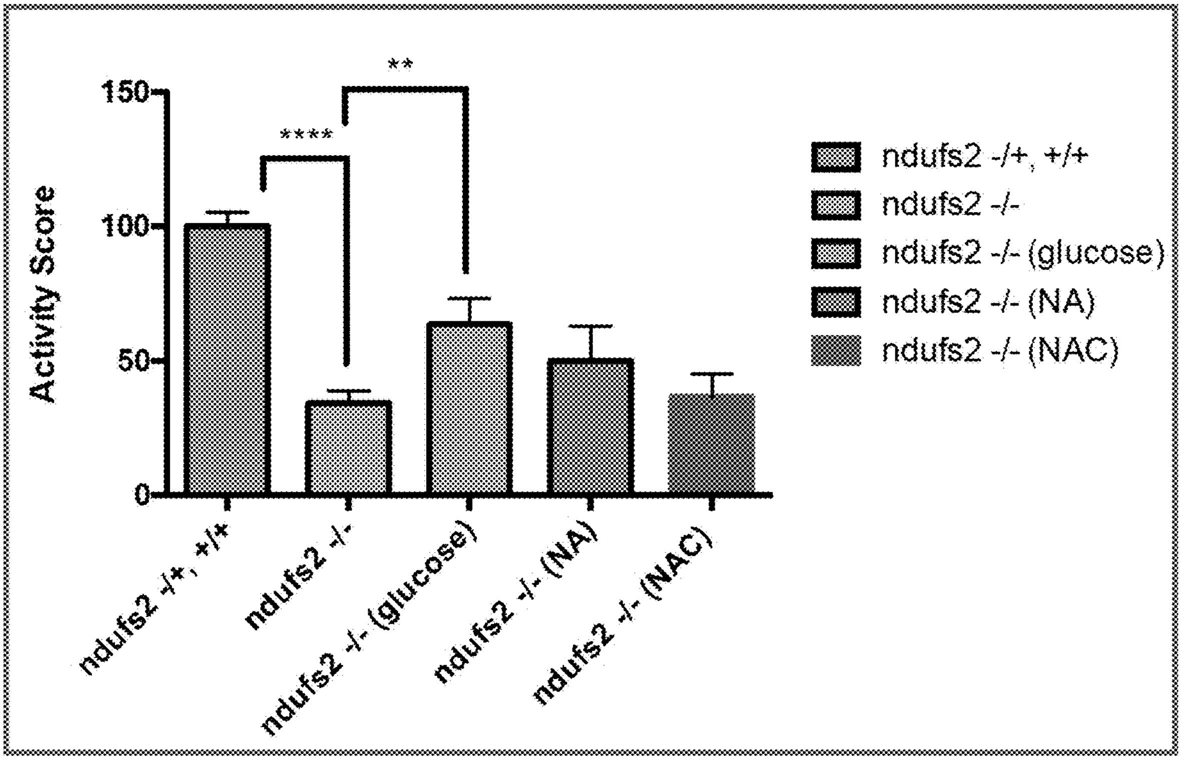

As discussed above, NAC+NA+Glu partially restored globally decreased gene expression. See FIG. 37A. FIG. 37B illustrates that this combination modulates activity in a ndufs2 mutant background.

These models could then be used to advantage to evaluate therapies that prevent stressor-induced decompensation, and/or reverse stress-induced cellular and animal dysfunction. Such stressors include, without limitation, nutrient modulation (galactose only media without glucose), extreme temperature stress, OXPHOS inhibitors (rotenone, azide, cyanide, chloramphenicol at lower doses than would affect wild-type control cells or animals).

Figure 38:
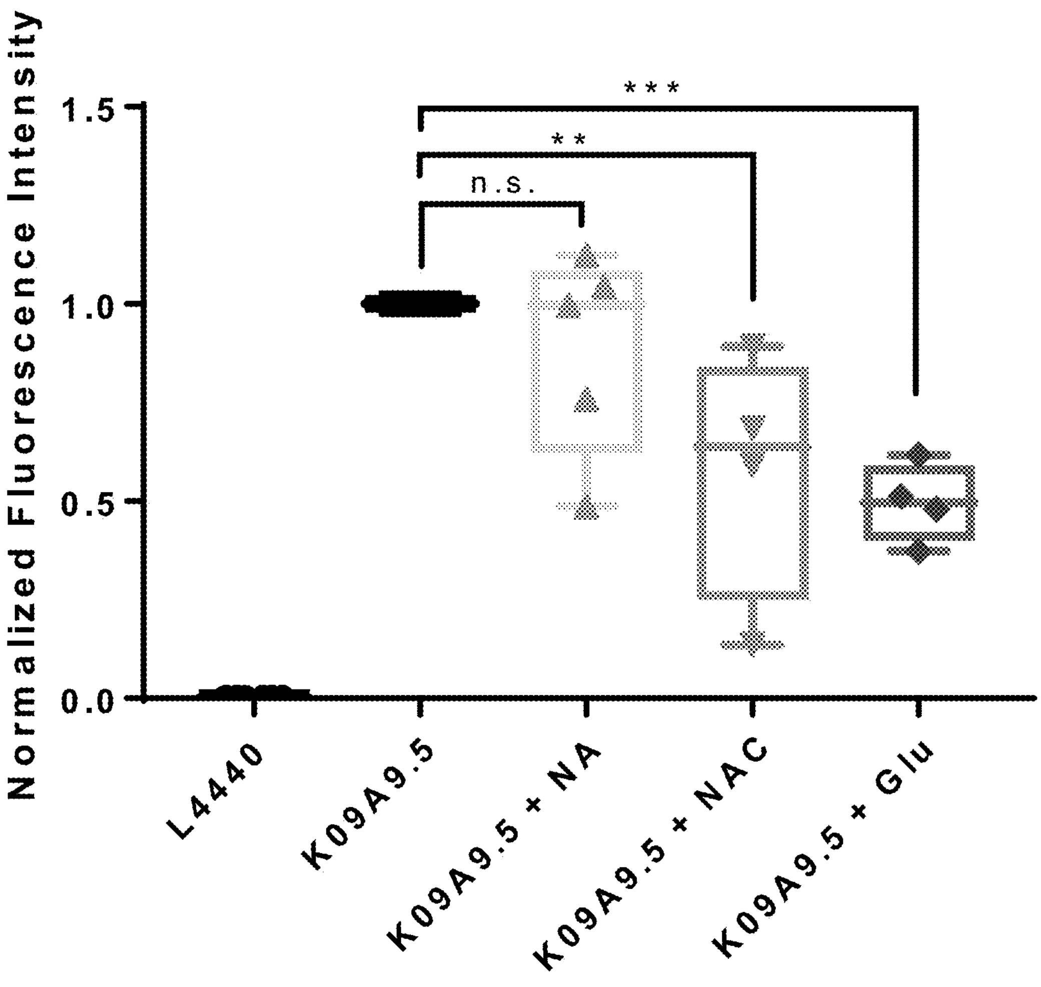
FIG. 38. UPRmt is significantly reduced by glucose (Glu) or N-acetylcysteine (NAC) therapy in K09A9.5 (gas-1) knockdown *C. elegans*. UPRmt is induced by knockdown of K09A9.5 in hsp-6p::gfp reporter worm strain with respect to L4440 empty vector RNAi control. 10 mM Glu or 2.5 mM NAC significantly reduce UPRmt stress response, with no effect seen with 1 mM Nicotinic acid (NA). , $p<0.01$; *, $p<0.001$ FIGS. 39A and 39B provide an overview depicting use of the methods and compositions described herein for pre-clinical screening of beneficial therapeutic agents. The specific mitochondrial disease models (Genes, stressors, etc) as well as specific experimental methods include but are not limited to those demonstrated from this schema.

Also provided herein is a novel screen to efficiently quantify the *C. elegans* mitochondrial unfolded protein response (UPRmt), which is similar to that of mammalian systems. UPRmt in *C. elegans* is assessed using a GFP reporter for hsp-6. Feeding RNA interference-based knockdown of K09A9.5 (gas-1, complex I subunit NDUFS2 orthologue) in the hsp-6p::gfp reporter worm strain strongly induces UPRmt, which is rapidly quantified by Union Biometrica Biosorter based on fluorescence intensity in living worms. Our data demonstrate that treatments of either glucose (10 mM) or N-acetylcysteine (2.5 mM) significantly reduce this mitochondrial stress response (FIG. 38).

High throughput screening of candidate mitochondrial disease therapies, and large drug libraries, is now readily achievable and underway for pre-clinical analysis of toxicity and efficacy of a range of therapies, concentrations, and combinations. Therapeutic leads are prioritized that restore animal survival, activity, and stress to healthy levels in diverse RC disease models. Therapeutic leads have been identified that are effective as positive controls for high-throughput drug screens, thereby facilitating identification of the most potent therapeutic leads that improve overall survival and function to take forward to clinical trials in mitochondrial disease patients with distinct genetic disorders.

Figure 39A:
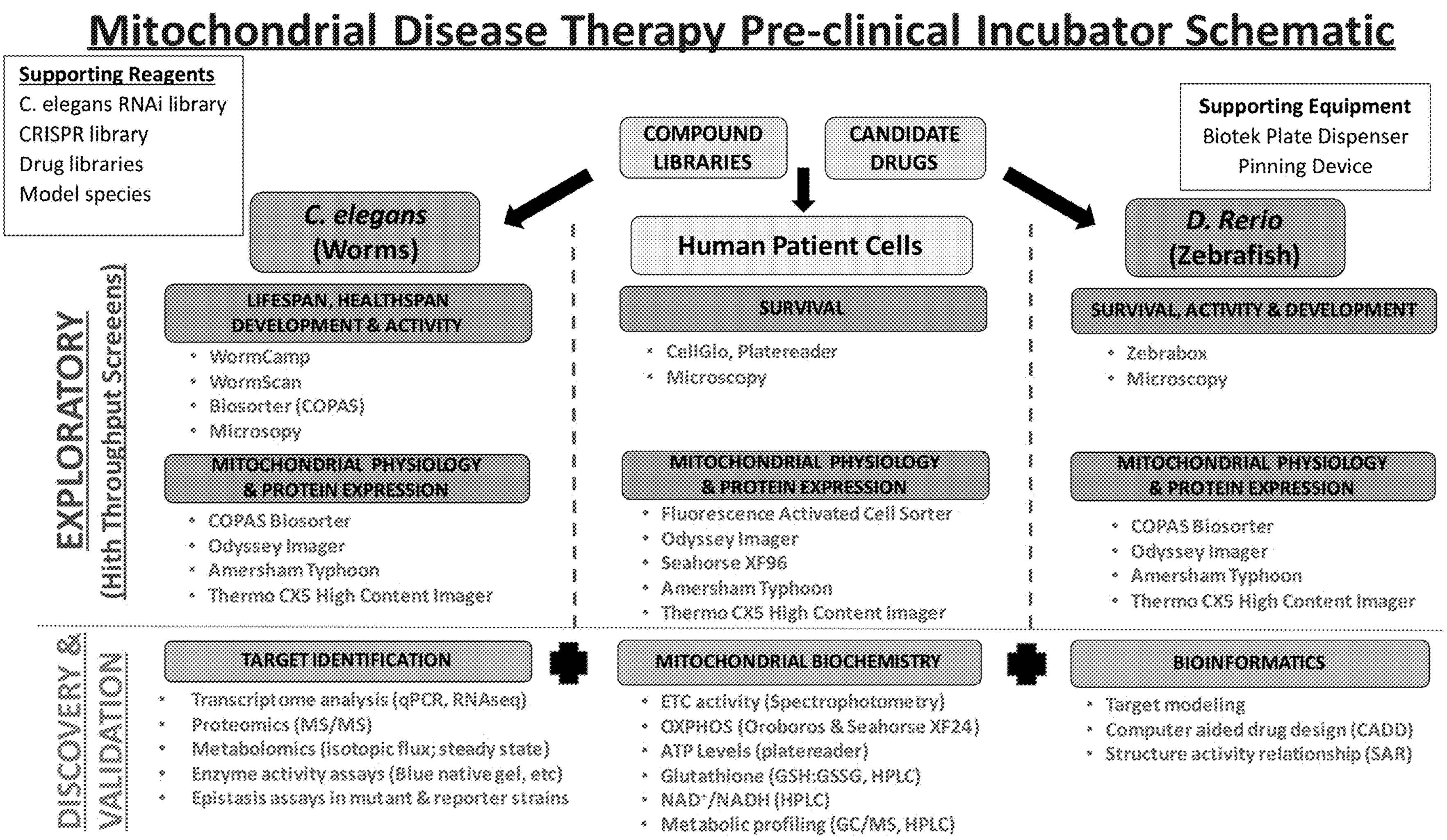
FIG. 39B provides a schematic view of methodology to design and implement customized precise treatment protocols for patients suffering from mitochondrial respiratory chain dysfunction and other disorders.
Figure 39B:
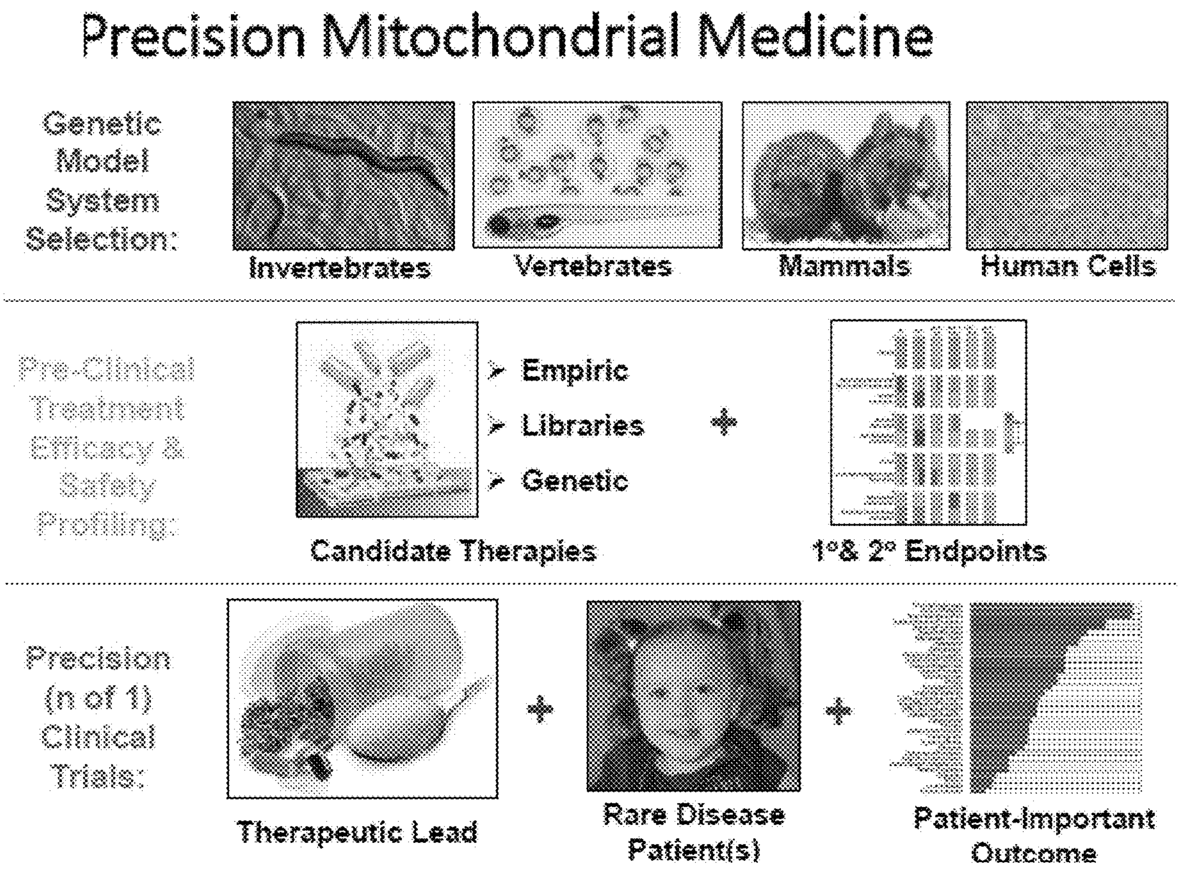

FIGS. 39A and 39B provides an overview depicting how the methods and compositions described herein can be utilized to for pre-clinical screening of beneficial therapeutic agents. The specific mitochondrial disease models (Genes, stressors, etc) as well as specific experimental methods include but are not limited to those demonstrated from this schema. FIG. 39B provides a schematic view of methodology to derive and implement customized precise treatment protocols for patients suffering from mitochondrial respiratory chain dysfunction and other disorders.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition having efficacy for ameliorating one or more symptoms of a mitochondrial disease in a subject in need thereof, wherein the composition consists of a combination of effective amounts of resveratrol, folinic acid and cysteamine, and acts synergistically to reduce said symptoms in said subject.

2. A method for alleviating symptoms associated with mitochondrial disease, comprising administration of the composition of claim 1 to a patient in need thereof.

3. The method of claim 2, wherein said symptoms include one or more of muscle weakness, exercise intolerance, chronic fatigue, gastrointestinal dysmotility, impaired balance, peripheral neuropathy, metabolic strokes, dysautonomia, vision loss, eye muscle and eyelid weakness, hearing loss, glomerular or tubular renal disease, endocrine dysfunction, dyslipidemia, cardiomyopathy, arrhythmia, anemia, failure to thrive, over or underweight, developmental delay, neurodevelopmental regression, cognitive decline and memory impairment, Parkinsonism, dystonia, liver dysfunction or failure, infertility, metabolic instability, stressor-induced acute decompensation, Dihydrolipoamide dehydrogenase (DLD) disease, Mitophagy disorders, Mitochondrial lipid biogenesis disorders, mitochondrial cofactor disorders, and secondary mitochondrial disorders resulting from toxins, drugs, age, prescribed or illicit medications, smoking, alcohol, environmental exposures, obesity, or genetic disorders that secondarily impair mitochondrial function, structure, or activities.

4. The method of claim 2, wherein said mitochondrial disease is selected from the group consisting of Complex I disease, Complex II disease, Complex III disease, Complex IV disease, Complex V disease, Multiple respiratory chain complex disease, adenine nucleotide translocase deficiency, pyruvate dehydrogenase deficiency, mitochondrial depletion disease, multiple mitochondrial DNA deletions disease, mitochondrial DNA maintenance defects, mitochondrial translation defects, mitochondrial nucleotide import disease, Friedreich's ataxia, Leber's Hereditary Optic Neuropathy, Kearns-Sayre Syndrome, Pearson Syndrome, Mitochondrial Myopathy, Mitochondrial Encephalomyopathy with Lactic Acidosis and Stroke-Like Episodes, Myoclonic epilepsy and ragged red fibers, Neurogenic Ataxia and Retinitis Pigmentosa, Mitochondrial Neuro-gastrointestinal encephalomopathy, maternally inherited diabetes and deafness, primary lactic acidosis, Leigh syndrome, Leigh-like syndrome, and multi-system mitochondrial disease.

* * * * *